United States Patent
Johnson et al.

(10) Patent No.: US 12,303,132 B2
(45) Date of Patent: May 20, 2025

(54) OCCLUDER AND ANASTOMOSIS DEVICES

(71) Applicant: W. L. Gore & Associates, Inc., Newark, DE (US)

(72) Inventors: Matthew A. Johnson, Bear, DE (US); Nathan K. Mooney, Elkton, MD (US); Lindsey Rappleyea, Bear, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 85 days.

(21) Appl. No.: 17/883,098

(22) Filed: Aug. 8, 2022

(65) Prior Publication Data

US 2022/0370071 A1    Nov. 24, 2022

Related U.S. Application Data

(60) Division of application No. 14/926,330, filed on Oct. 29, 2015, now Pat. No. 11,439,396, which is a
(Continued)

(51) Int. Cl.
*A61B 17/11* (2006.01)
*A61B 17/00* (2006.01)
*A61B 17/12* (2006.01)

(52) U.S. Cl.
CPC .......... *A61B 17/11* (2013.01); *A61B 17/0057* (2013.01); *A61B 17/12022* (2013.01);
(Continued)

(58) Field of Classification Search
CPC ...... A61B 17/0057; A61B 2017/00575; A61B 2017/00579; A61B 2017/00584;
(Continued)

(56) References Cited

U.S. PATENT DOCUMENTS 3,818,511 A   6/1974   Goldberg et al.
4,119,100 A   10/1978  Rickett
(Continued)

FOREIGN PATENT DOCUMENTS

CN   101374477 A   2/2009
CN   201379668 Y   1/2010
(Continued)

OTHER PUBLICATIONS

International Preliminary Report on Patentability received for PCT Patent Application No. PCT/US2015/028707, mailed on Nov. 17, 2016, 12 pages.
(Continued)

*Primary Examiner* — Todd J Scherbel

(57) ABSTRACT

An implantable medical device for sealing and repairing defects in a body tissue or for creating an anastomosis includes a frame and a covering material. In some embodiments, the frame includes a single continuously wound wire that defines an apposition portion, a defect-occupying portion, and a sealing portion. In some embodiments, the tissue-sealing and anastomosis devices provided herein are well-suited for use in the GI tract including the small bowel and colon. In some embodiments, a two-part frame construct facilitates independent tailoring of apposition forces and radial forces exerted on tissues by the two-part frame.

28 Claims, 25 Drawing Sheets

Related U.S. Application Data continuation-in-part of application No. 14/701,440, filed on Apr. 30, 2015, now Pat. No. 11,712,230.

(60) Provisional application No. 61/987,802, filed on May 2, 2014.

(52) U.S. Cl.
CPC .............. *A61B 2017/00592* (2013.01); *A61B 2017/00597* (2013.01); *A61B 2017/00615* (2013.01); *A61B 2017/00623* (2013.01); *A61B 2017/00818* (2013.01); *A61B 2017/1107* (2013.01); *A61B 17/1114* (2013.01); *A61B 17/12145* (2013.01)

(58) Field of Classification Search
CPC ........... A61B 2017/00592; A61B 2017/00597; A61B 2017/00606; A61B 2017/00615; A61B 2017/00619; A61B 2017/00637; A61B 2017/00867

See application file for complete search history.

(56) References Cited

U.S. PATENT DOCUMENTS

| | | | |
|---|---|---|---|
| 4,338,937 A | 7/1982 | Lerman |
| 4,381,765 A | 5/1983 | Burton |
| 5,224,953 A | 7/1993 | Morgentaler |
| 5,261,898 A | 11/1993 | Polin et al. |
| 5,354,308 A | 10/1994 | Simon et al. |
| 5,562,728 A | 10/1996 | Lazarus et al. |
| 5,741,297 A | 4/1998 | Simon |
| 5,755,778 A | 5/1998 | Kleshinski |
| 5,797,933 A | 8/1998 | Snow et al. |
| 5,830,222 A | 11/1998 | Makower |
| 5,868,783 A | 2/1999 | Tower |
| 5,945,994 A | 8/1999 | Shimizu et al. |
| 5,957,949 A | 9/1999 | Leonhardt et al. |
| 6,007,544 A | 12/1999 | Kim |
| 6,077,291 A | 6/2000 | Das |
| 6,120,534 A | 9/2000 | Ruiz |
| 6,165,209 A | 12/2000 | Patterson et al. |
| 6,168,617 B1 | 1/2001 | Blaeser et al. |
| 6,168,621 B1 | 1/2001 | Vrba |
| 6,171,329 B1 | 1/2001 | Shaw et al. |
| 6,193,734 B1 | 2/2001 | Bolduc et al. |
| 6,214,029 B1 | 4/2001 | Thill et al. |
| 6,217,608 B1 | 4/2001 | Penn et al. |
| 6,290,728 B1 | 9/2001 | Phelps et al. |
| 6,315,708 B1 | 11/2001 | Salmon et al. |
| 6,315,792 B1 | 11/2001 | Armstrong et al. |
| 6,355,052 B1 | 3/2002 | Neuss et al. |
| 6,391,036 B1 | 5/2002 | Berg et al. |
| 6,391,039 B1 | 5/2002 | Nicholas et al. |
| 6,416,543 B1 | 7/2002 | Hilaire et al. |
| 6,419,681 B1 | 7/2002 | Vargas et al. |
| 6,432,127 B1 | 8/2002 | Kim et al. |
| 6,468,303 B1 | 10/2002 | Amplatz et al. |
| 6,485,496 B1 | 11/2002 | Suyker et al. |
| 6,485,507 B1 | 11/2002 | Walak et al. |
| 6,488,702 B1 | 12/2002 | Besselink |
| 6,579,314 B1 | 6/2003 | Lombardi et al. |
| 6,585,758 B1 | 7/2003 | Chouinard et al. |
| 6,616,675 B1 | 9/2003 | Evard et al. |
| 6,629,992 B2 | 10/2003 | Bigus et al. |
| 6,666,883 B1 | 12/2003 | Seguin et al. |
| 6,712,836 B1 | 3/2004 | Berg et al. |
| 6,830,575 B2 | 12/2004 | Stenzel et al. |
| 6,863,684 B2 | 3/2005 | Kim et al. |
| 6,866,674 B2 | 3/2005 | Galdonik et al. |
| 6,911,037 B2 | 6/2005 | Gainor et al. |
| 6,945,994 B2 | 9/2005 | Austin et al. |
| 6,958,037 B2 | 10/2005 | Ewers et al. |
| 7,022,131 B1 | 4/2006 | Derowe et al. |
| 7,025,777 B2 | 4/2006 | Moore |
| 7,029,482 B1 | 4/2006 | Vargas et al. |
| 7,037,344 B2 | 5/2006 | Kagan et al. |
| 7,115,136 B2 | 10/2006 | Park et al. |
| 7,182,771 B1 | 2/2007 | Houser et al. |
| 7,223,274 B2 | 5/2007 | Vargas et al. |
| 7,252,680 B2 | 8/2007 | Freitag |
| 7,303,569 B2 | 12/2007 | Yencho et al. |
| 7,431,729 B2 | 10/2008 | Chanduszko |
| 7,527,644 B2 | 5/2009 | Mangiardi et al. |
| 7,547,321 B2 | 6/2009 | Silvestri et al. |
| 7,585,306 B2 | 9/2009 | Abbott et al. |
| 7,608,086 B2 | 10/2009 | Tanaka et al. |
| 7,632,302 B2 | 12/2009 | Vreeman et al. |
| 7,780,686 B2 | 8/2010 | Park et al. |
| 7,828,814 B2 | 11/2010 | Brenneman et al. |
| 7,892,247 B2 | 2/2011 | Conston et al. |
| 7,901,430 B2 | 3/2011 | Matsuura et al. |
| 8,043,360 B2 | 10/2011 | McNamara et al. |
| 8,109,946 B2 | 2/2012 | Cahill et al. |
| 8,114,125 B2 | 2/2012 | Seibold et al. |
| 8,197,498 B2 | 6/2012 | Coleman et al. |
| 8,257,389 B2 | 9/2012 | Chanduszko et al. |
| 8,262,691 B2 | 9/2012 | McGuckin et al. |
| 8,343,088 B2 | 1/2013 | Bates et al. |
| 8,398,676 B2 | 3/2013 | Roorda et al. |
| 8,409,167 B2 | 4/2013 | Roschak |
| 8,425,539 B2 | 4/2013 | Binmoeller et al. |
| 8,430,934 B2 | 4/2013 | Das |
| 8,435,284 B2 | 5/2013 | Eidenschink et al. |
| 8,454,632 B2 | 6/2013 | Binmoeller et al. |
| 8,579,935 B2 | 11/2013 | Devries et al. |
| 8,641,747 B2 | 2/2014 | Brenneman et al. |
| 8,679,171 B2 | 3/2014 | Deem et al. |
| 8,728,155 B2 | 5/2014 | Montorfano et al. |
| 8,740,940 B2 | 6/2014 | Maahs et al. |
| 8,864,813 B2 | 10/2014 | Barr |
| 8,870,916 B2 | 10/2014 | Ewers et al. |
| 8,992,604 B2 | 3/2015 | Gross et al. |
| 9,597,204 B2 | 3/2017 | Benary et al. |
| 9,668,853 B2 | 6/2017 | Shin |
| 9,782,533 B2 | 10/2017 | Brenneman et al. |
| 9,993,251 B2 | 6/2018 | Todd et al. |
| 10,004,509 B2 | 6/2018 | Todd |
| 10,363,040 B2 | 7/2019 | Sambandam |
| 10,806,458 B2 | 10/2020 | Todd |
| 11,439,396 B2 * | 9/2022 | Johnson ........... A61B 17/12022 |
| 11,712,230 B2 * | 8/2023 | Johnson ........... A61B 17/12099 606/191 |
| 11,724,075 B2 | 8/2023 | Johnson |
| 2001/0021872 A1 | 9/2001 | Bailey et al. |
| 2001/0047180 A1 | 11/2001 | Grudem et al. |
| 2002/0082627 A1 | 6/2002 | Berg et al. |
| 2002/0099431 A1 | 7/2002 | Armstrong et al. |
| 2002/0099437 A1 | 7/2002 | Anson et al. |
| 2002/0161341 A1 | 10/2002 | Stinson et al. |
| 2002/0169475 A1 | 11/2002 | Gainor et al. |
| 2002/0183787 A1 | 12/2002 | Wahr et al. |
| 2003/0028213 A1 | 2/2003 | Thill et al. |
| 2003/0032967 A1 | 2/2003 | Park et al. |
| 2003/0055441 A1 | 3/2003 | Suyker et al. |
| 2003/0069533 A1 | 4/2003 | Kakutani et al. |
| 2003/0093096 A1 | 5/2003 | McGuckin et al. |
| 2003/0109893 A1 | 6/2003 | Vargas et al. |
| 2003/0120292 A1 | 6/2003 | Park et al. |
| 2003/0139819 A1 | 7/2003 | Beer et al. |
| 2003/0144578 A1 | 7/2003 | Kenneth |
| 2003/0191482 A1 | 10/2003 | Suyker et al. |
| 2003/0225421 A1 | 12/2003 | Peavey et al. |
| 2004/0073242 A1 | 4/2004 | Chanduszko |
| 2004/0078053 A1 | 4/2004 | Berg et al. |
| 2004/0092977 A1 | 5/2004 | Vargas et al. |
| 2004/0098105 A1 | 5/2004 | Stinson et al. |
| 2004/0133236 A1 | 7/2004 | Chanduszko |
| 2004/0204755 A1 | 10/2004 | Robin |
| 2004/0211433 A1 | 10/2004 | Albright |
| 2005/0049675 A1 | 3/2005 | Wallace |
| 2005/0055082 A1 | 3/2005 | Ben Muvhar et al. |
| 2005/0070934 A1 | 3/2005 | Tanaka et al. |

(56) References Cited

U.S. PATENT DOCUMENTS

| | | |
|---|---|---|
| 2005/0070935 A1 | 3/2005 | Ortiz |
| 2005/0070957 A1 | 3/2005 | Das |
| 2005/0149071 A1 | 7/2005 | Abbott et al. |
| 2005/0154465 A1 | 7/2005 | Hodges et al. |
| 2005/0228413 A1 | 10/2005 | Binmoeller et al. |
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |
| 2006/0200228 A1 | 9/2006 | Penn et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1 | 7/2007 | Jimenez et al. |
| 2007/0244518 A1 | 10/2007 | Callaghan |
| 2007/0249985 A1 | 10/2007 | Brenneman et al. |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller et al. |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1 | 4/2009 | Navia |
| 2009/0118745 A1 | 5/2009 | Paul, Jr. |
| 2009/0143713 A1 | 6/2009 | Van et al. |
| 2009/0187240 A1 | 7/2009 | Clerc et al. |
| 2009/0228038 A1 | 9/2009 | Amin |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1 | 2/2010 | Navia |
| 2010/0100105 A1 | 4/2010 | Bates et al. |
| 2010/0106171 A1 | 4/2010 | Arepally et al. |
| 2010/0114128 A1 | 5/2010 | Coleman et al. |
| 2010/0114290 A1 | 5/2010 | Rasmussen et al. |
| 2010/0130995 A1 | 5/2010 | Yevzlin et al. |
| 2010/0168835 A1 | 7/2010 | Dorn |
| 2010/0174253 A1 | 7/2010 | Cline et al. |
| 2010/0234878 A1 | 9/2010 | Hruska et al. |
| 2010/0256548 A1 | 10/2010 | McNamara et al. |
| 2010/0268316 A1 | 10/2010 | Brenneman et al. |
| 2010/0305590 A1 | 12/2010 | Holmes et al. |
| 2010/0331953 A1 | 12/2010 | Matsuoka et al. |
| 2011/0040366 A1 | 2/2011 | Goetz et al. |
| 2011/0054381 A1 | 3/2011 | Van et al. |
| 2011/0060398 A1 | 3/2011 | Tupil et al. |
| 2011/0118765 A1 | 5/2011 | Aguirre |
| 2011/0125244 A1 | 5/2011 | Roeder et al. |
| 2011/0137410 A1 | 6/2011 | Hacohen |
| 2011/0213415 A1 | 9/2011 | McGuckin et al. |
| 2011/0218609 A1 | 9/2011 | Chobotov et al. |
| 2011/0257461 A1 | 10/2011 | Lipperman et al. |
| 2011/0257723 A1 | 10/2011 | McNamara |
| 2011/0301689 A1 | 12/2011 | Dorn et al. |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1 | 7/2012 | Campbell et al. |
| 2012/0232505 A1 | 9/2012 | Eskaros et al. |
| 2012/0241503 A1 | 9/2012 | Baxter, III et al. |
| 2013/0012969 A1 | 1/2013 | Shin |
| 2013/0030351 A1 | 1/2013 | Belhe et al. |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1 | 4/2013 | Bruchman et al. |
| 2013/0165967 A1 | 6/2013 | Amin et al. |
| 2013/0197623 A1 | 8/2013 | McHugo |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein et al. |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center et al. |
| 2015/0066077 A1 | 3/2015 | Akpinar |
| 2015/0250630 A1 | 9/2015 | Irwin et al. |
| 2015/0265437 A1 | 9/2015 | Fleury et al. |
| 2015/0313595 A1 | 11/2015 | Houghton et al. |
| 2015/0313598 A1 | 11/2015 | Todd et al. |
| 2015/0313599 A1 | 11/2015 | Johnson et al. |
| 2015/0313738 A1 | 11/2015 | Cully et al. |
| 2016/0045199 A1 | 2/2016 | Mooney |
| 2016/0135813 A1 | 5/2016 | Johnson et al. |
| 2016/0256169 A1 | 9/2016 | Ben-Muvhar et al. |
| 2017/0020498 A1 | 1/2017 | Blom |
| 2017/0105854 A1 | 4/2017 | Treacy et al. |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2019/0298909 A1 | 10/2019 | Cully et al. |
| 2020/0015823 A1 | 1/2020 | Sambandam |
| 2020/0146680 A1 | 5/2020 | Houghton et al. |
| 2021/0085328 A1 | 3/2021 | Todd |
| 2022/0257252 A1 | 8/2022 | Todd et al. |

FOREIGN PATENT DOCUMENTS

| | | |
|---|---|---|
| CN | 101951983 A | 1/2011 |
| CN | 102083391 A | 6/2011 |
| CN | 102395323 A | 3/2012 |
| CN | 102802539 A | 11/2012 |
| CN | 202801864 U | 3/2013 |
| CN | 103200975 A | 7/2013 |
| CN | 103209649 A | 7/2013 |
| CN | 103313681 A | 9/2013 |
| CN | 103598902 A | 2/2014 |
| CN | 103945775 A | 7/2014 |
| CN | 104168839 A | 11/2014 |
| CN | 104244843 A | 12/2014 |
| CN | 104519838 A | 4/2015 |
| CN | 104968284 A | 10/2015 |
| CN | 106413586 A | 2/2017 |
| DE | 10148185 A1 | 4/2003 |
| EP | 0991375 A1 | 4/2000 |
| EP | 1790297 A1 | 5/2007 |
| EP | 1872741 A1 | 1/2008 |
| EP | 1480565 B1 | 12/2008 |
| EP | 2543323 A1 | 1/2013 |
| EP | 3136982 A2 | 3/2017 |
| EP | 3136984 A1 | 3/2017 |
| GB | 2409978 A | 7/2005 |
| JP | 2000-505316 A | 5/2000 |
| JP | 2001-501493 A | 2/2001 |
| JP | 2001-520908 A | 11/2001 |
| JP | 2001-340346 A | 12/2001 |
| JP | 2003-527939 A | 9/2003 |
| JP | 2004-049806 A | 2/2004 |
| JP | 2005-503881 A | 2/2005 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-097620 A | 4/2007 |
| JP | 2007-530128 A | 11/2007 |
| JP | 2009-508641 A | 3/2009 |
| JP | 2009-518149 A | 5/2009 |
| JP | 2010-523209 A | 7/2010 |
| JP | 2010-528821 A | 8/2010 |
| JP | 2010-188189 A | 9/2010 |
| JP | 2011-509758 A | 3/2011 |
| JP | 2011-519709 A | 7/2011 |
| JP | 2012-513783 A | 6/2012 |

(56) References Cited

FOREIGN PATENT DOCUMENTS

| | | |
|---|---|---|
| JP | 2013-013715 A | 1/2013 |
| JP | 2014-503246 A | 2/2014 |
| JP | 2015-500665 A | 1/2015 |
| JP | 2021-192846 A | 12/2021 |
| WO | 97/27898 A1 | 8/1997 |
| WO | 97/32543 A1 | 9/1997 |
| WO | 98/02099 A1 | 1/1998 |
| WO | 98/08462 A2 | 3/1998 |
| WO | 98/16174 A1 | 4/1998 |
| WO | 98/58600 A1 | 12/1998 |
| WO | 01/72367 A1 | 10/2001 |
| WO | 02/83038 A2 | 10/2002 |
| WO | 2003/028522 A2 | 4/2003 |
| WO | 2003/073944 A1 | 9/2003 |
| WO | 2003/103476 A2 | 12/2003 |
| WO | 2004/012603 A2 | 2/2004 |
| WO | 2004/087236 A2 | 10/2004 |
| WO | 2005/089655 A1 | 9/2005 |
| WO | 2006/121855 A2 | 11/2006 |
| WO | 2007/024964 A1 | 3/2007 |
| WO | 2007/053243 A2 | 5/2007 |
| WO | 2007/100970 A2 | 9/2007 |
| WO | 2008/157172 A1 | 12/2008 |
| WO | 2009/082718 A1 | 7/2009 |
| WO | 2009/091899 A2 | 7/2009 |
| WO | 2009/109348 A1 | 9/2009 |
| WO | 2009/140195 A1 | 11/2009 |
| WO | 2009/146369 A1 | 12/2009 |
| WO | 2010/076052 A1 | 7/2010 |
| WO | 2010/129162 A1 | 11/2010 |
| WO | 2012/034108 A1 | 3/2012 |
| WO | 2012/067912 A1 | 5/2012 |
| WO | 2012/071075 A1 | 5/2012 |
| WO | 2013/152891 A2 | 10/2013 |
| WO | 2015/168501 A2 | 11/2015 |
| WO | 2015/168504 A2 | 11/2015 |
| WO | 2015/168506 A1 | 11/2015 |
| WO | 2015/168507 A1 | 11/2015 |
| WO | 2015/168508 A2 | 11/2015 |

OTHER PUBLICATIONS

International Preliminary Report on Patentability received for PCT Patent Application No. PCT/US2016/055255, mailed on May 11, 2018, 7 pages.
International Search Report and Written Opinion from PCT/US2015/028707, mailed Oct. 23, 2015, 19 pages.
International Search Report and Written Opinion received for PCT Patent Application No. PCT/US2016/055255, mailed on Jan. 20, 2017, 8 pages.

* cited by examiner

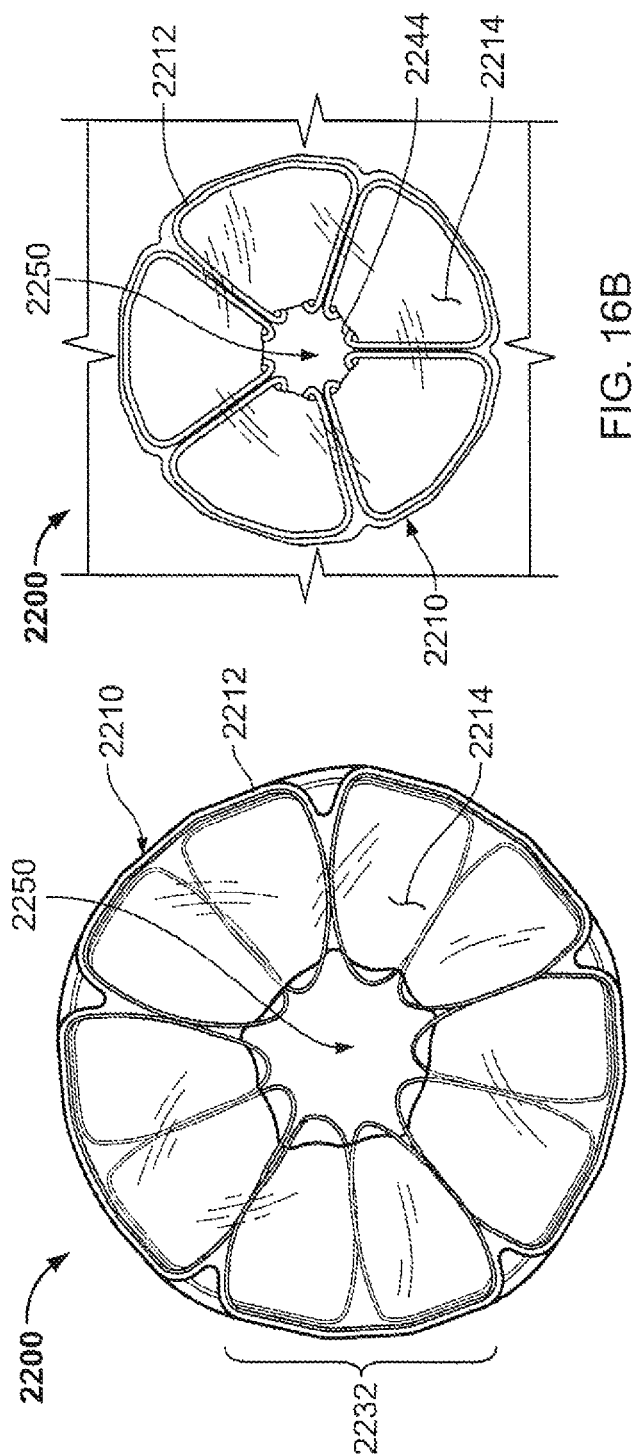
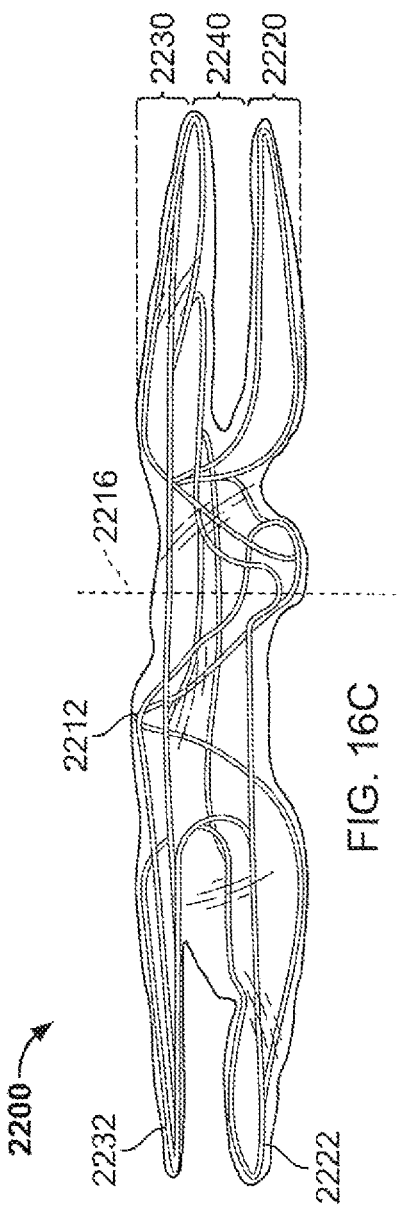

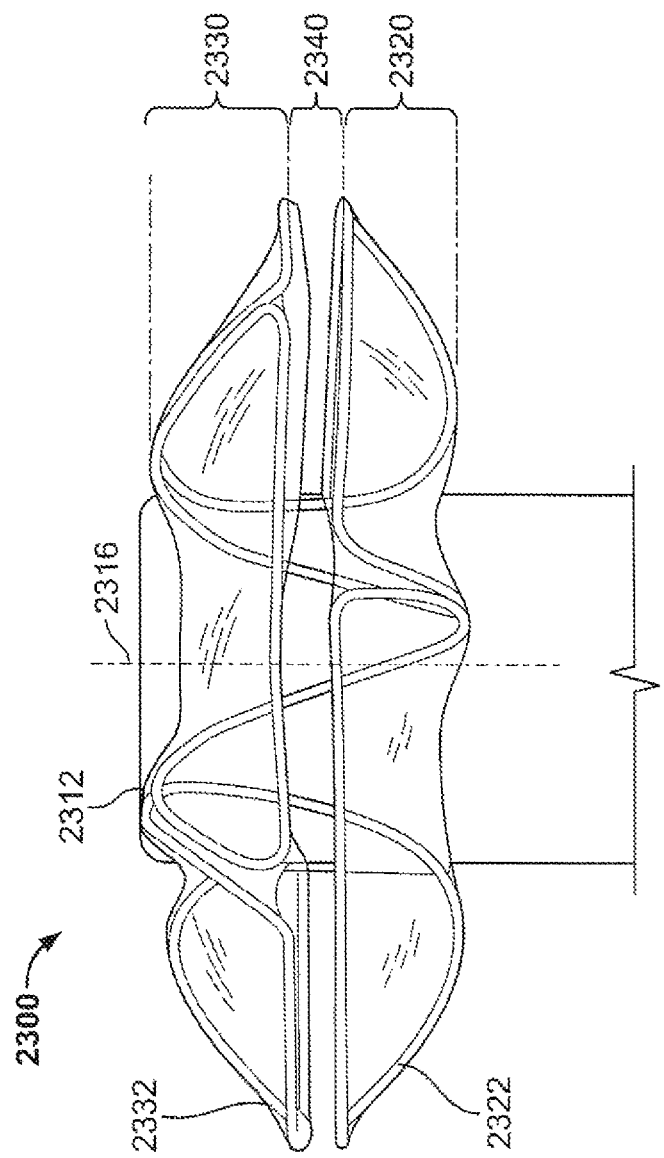

OCCLUDER AND ANASTOMOSIS DEVICES

This application is a divisional of U.S. patent application Ser. No. 14/926,330, filed Oct. 29, 2015, which is a continuation in part of U.S. patent application Ser. No. 14/701,440, filed Apr. 30, 2015, which claims the benefit of U.S. Provisional Application 61/987,802, filed May 2, 2014, all of which are incorporated herein by reference in their entireties for all purposes.

FIELD

This disclosure relates generally to implantable medical devices, and more specifically, to implantable medical devices for connecting tissue layers to create an anastomosis and to implantable devices for occluding inhibiting or preventing material movement through tissue apertures, sealing, and allowing healing of defects in tissues.

BACKGROUND

Lesions of the gastrointestinal (GI) tract can be in the form of polyps that protrude from the mucosal lining with a mushroom-like shape, or flat lesions that are flush on the mucosal lining. The need to remove lesions from the mucosal lining of the GI tract is common and growing worldwide. The likelihood of having colon lesions increases with age. Approximately half of the people over the age of 60 have at least one colon lesion and often more. Some polyps are considered pre-cancerous, which means that while they are not cancer, if left untreated they may develop into cancer. GI tract lesions are typically found during cancer screening tests, such as a colonoscopy or flexible sigmoidoscopy.

Benign and early malignant lesions of the GI tract can usually be removed endoscopically using an electrocautery snare, hot snare, cold snare, or electrocautery knife devices. A saline-assisted polypectomy procedure is often used for the removal of large flat lesions in the GI tract. When lesions become still larger and invasively encompass more than just the mucosal layers of the GI tract, a resection procedure is often performed whereby the full thickness of the wall tissue is removed along with the lesion. This procedure is typically performed using laparoscopic or open surgery techniques rather than endoscopically. However, open surgery may not be an option for some patients, and laparoscopic procedures may not allow visualization within the lumen of the conduit being treated.

Large resections of the colon are not typically performed endoscopically in part because tools and devices to adequately seal the resulting perforation in the colon wall are not available without approximating the defect edges which can result in lumen stricture (e.g., using clips, sutures, and the like). Such tools and devices are challenging to develop in part because of the relatively hostile colon environment that includes peristaltic movements and fecal matter.

An anastomosis is a cross-connection between two tubular tissue structures, such as blood vessels or intestines. For example, when a portion of an intestine is resected, the resulting two ends can be sewn or stapled together (anastomosed), using an intestinal anastomosis procedure. This procedure can restore intestinal continuity after the resection of a bowel portion, or to bypass a portion of unresectable diseased bowel.

Anastomoses can be created in various manners including, but not limited to: end-to-end, end-to-side, and side-to-side anastomoses. Often, suturing is used to create such anastomoses.

SUMMARY

One aspect of the invention relates to a medical device for sealing a defect or structure in tissue. The medical device includes a frame having single elongate member. The elongate member includes (1) a supporting portion configured to conform to a geometry of a first tissue surface and to provide an apposition force against the first tissue surface, (2) an occluding portion configured to conform to a geometry of a second tissue surface and to provide an apposition force against the second tissue surface, and (3) a defect-occupying portion disposed between the supporting portion and the occluding portion. The defect-occupying portion is configured to not provide a substantial apposition force against tissue around an aperture of the defect. The medical device also includes a sealing material attached to at least a portion of the occluding portion. The sealing material is configured to inhibit material flow through the aperture.

A second aspect of the invention relates to a medical device for sealing a defect or structure in tissue. The medical device includes a wire member that includes a single wound wire. The wire includes (a) a sealing member, (2) an apposition member, and (3) a defect-occupying portion disposed between the sealing member and the apposition member. The medical device also includes a covering material disposed on at least a portion of the sealing member.

A third aspect of the invention relates to a medical device system that includes (1) a frame including a single elongate member and (2) a delivery sheath defining a lumen. The elongate member forms (1) a supporting portion that is configured to conform to a geometry of a first tissue surface and to provide an apposition force against the first tissue surface, (2) an occluding portion that is configured to conform to a geometry of a second tissue surface and to provide an apposition force against the second tissue surface, (3) a defect-occupying portion disposed between the supporting portion and the occluding portion, and (4) a membrane attached to at least a portion of the occluding portion. The membrane is configured to inhibit material flow through the aperture. In addition, the medical device is configurable in a low-profile configuration such that the medical device can be contained within the lumen. Further, the medical device is configured to expand from the low-profile configuration when the device is liberated from the lumen.

A fourth aspect of the invention relates to a method of sealing an aperture in a patient's body. The method includes inserting an implantable medical device into the aperture using a transcatheter technique. The device includes a single wound wire and a covering material. The wire forms (1) a sealing member, (2) an apposition member, and (3) a defect-occupying portion disposed between the sealing member and the apposition member. The covering material is disposed on at least a portion of the sealing member and is configured to fully overlay the aperture.

A fifth aspect of the invention relates to an implantable medical device that includes a single elongate member. The single elongate member forms (1) a first flange having a plurality of first arms configured about a central axis and forming a circumferential sealing portion at the outer edges of said first flange, (2) a second flange having a plurality of second arms configured about the central axis, and (3) a connecting region interconnecting the first and second flanges and adapted to bridge a defect in a lumen wall. In some embodiments, the first arms and the second arms have a pre-strained geometry such that an apposition force exists in the presence of the lumen wall and the apposition force does not exist in the absence of said lumen wall.

A sixth aspect of the invention relates to an implantable medical device that includes a single elongate member. The elongate member forms (1) a first flange having a plurality of first arms configured about a central axis and forming a circumferential seal at outer edges of the first flange, (2) a second flange having a plurality of second arms configured about the central axis forming a circumferential sealing portion at outer edges of the second flange, and (3) a connecting region interconnecting the first and second flanges and adapted to cross a defect in a lumen wall. The connecting region fluidly connects the first and second flanges. The first arms and the second arms have a pre-strained geometry such that an apposition force exists in the presence of the lumen wall and the apposition force does not exist in the absence of the lumen wall.

A seventh aspect of the invention relates to an implantable medical device that includes a single elongate member. The single elongate member forms (1) a first flange having a plurality of first arms configured about a central axis and forming a circumferential sealing portion at the outer edges of the first flange, (2) a second flange having a plurality of second arms configured about the central axis, and (3) a connecting region interconnecting the first and second flanges and adapted to cross a defect in a lumen wall. The first arms and the second arms have a pre-strained geometry such that an apposition force exists in the absence of a lumen wall.

An eighth aspect of the invention relates to an implantable medical device that includes an apposition frame member that forms (1) a first flange having a plurality of first apposition petals configured about a central axis and forming a first circumferential sealing portion, (2) a second flange having a plurality of second apposition petals configured about the central axis and forming a second circumferential sealing portion, and (3) a connecting region connecting the first and second flanges. The connecting region defines an aperture along the central axis. The implantable medical device also includes a support frame member that forms a plurality of apices and covering material disposed on at least a portion of each of the apposition frame member and the support frame member. In exemplary embodiments, the support frame is disposed concentrically within the aperture.

A ninth aspect of the invention relates to a tissue-sealing device that includes a frame and a covering material disposed on at least a sealing portion of the frame. The frame includes an apposition portion, a sealing portion, and a defect-occupying portion. In exemplary embodiments, the apposition portion and the sealing portion are configured dissimilarly. The frame defines diamond-shaped petals that form the sealing portion and triangularly-shaped petals that form the apposition portion. The edges of the diamond-shaped petals in the sealing portion are substantially parallel to each other, which creates a line of physical contact and a sealing edge and reduces the presence of leakage channels between the sealing petals. In contrast, the triangularly-shaped petals in the apposition portion are discrete and may tangentially contact each other. The tissue-sealing device may be configured to be implanted in a patient such that the covering material fully overlays and seals a tissue aperture.

A tenth aspect relates to a tissue sealing device that includes a frame and a covering material disposed on at least a portion of a sealing portion of the frame. The frame includes an apposition portion, a sealing portion, and a defect-occupying portion. In exemplary embodiments the apposition portion and the sealing portion are configured dissimilarly. The apposition petals and the sealing petals include a linear portion extending radially from the defect-occupying portion and an essentially diamond-shaped outer portion extending from the linear portion at the free ends of the petals. The sealing petals and the apposition petals are substantially similar, with the exception that the sealing petals have a more rounded outermost edge than the apposition petals. The outermost edges of the sealing petals tangentially touch each other. The abutment of the edges of the sealing petals creates a line of physical contact and a sealing edge and reduces the presence of leakage channels between the sealing petals. The apposition petals in the apposition portion are discrete (not covered with a covering material) and may move relative to each other. The more rounded ends of the sealing petals (opposed to the less rounded ends of the apposition petals) creates a substantially uniform pressure distribution at the exterior circumference, and in the apposition portion, to facilitate loading into a delivery device. The tissue-sealing device may be configured to be implanted in a patient such that the covering material fully overlays and seals a tissue aperture.

DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 16A is a plan view of an exemplary anastomosis device in accordance with some embodiments;

FIG. 16B is a plan view showing the exemplary anastomosis device of FIG. 16A engaged with tissues to create an anastomosis;

FIG. 16C is an elevation view of the exemplary anastomosis device of FIG. 16A;

FIG. 17C is an elevation view of the exemplary anastomosis device of FIG. 17A;

DETAILED DESCRIPTION

Figure 1A:
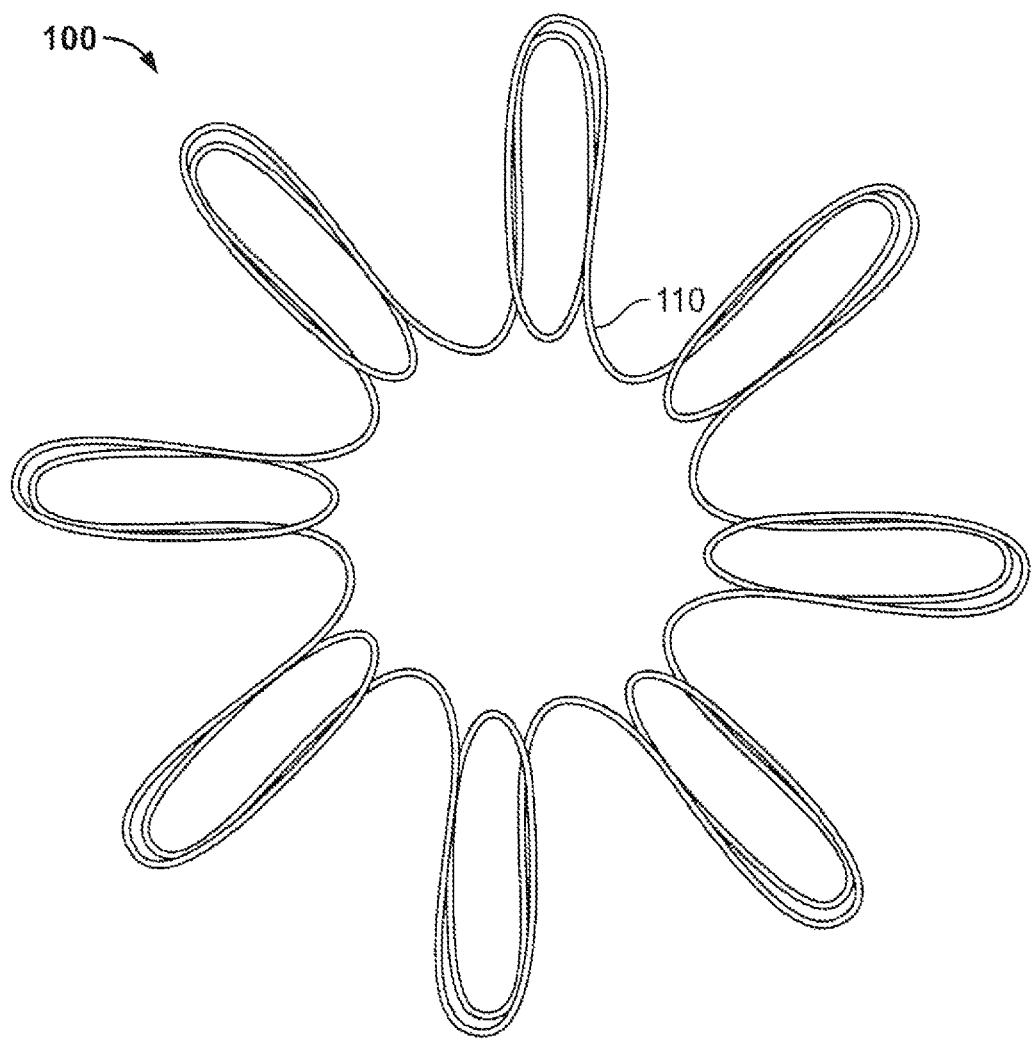
FIG. 1A is a plan view of a wire frame of an exemplary tissue-sealing device in accordance with some embodiments.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the drawing figures should not be construed as limiting.

This disclosure provides implantable medical devices and methods for treating medical conditions using the implantable medical devices. For example, this disclosure provides implantable devices for occluding, sealing, and allowing the healing of tissue defects. Tissues that may be treated include, but are not limited to, those of the GI tract, peritoneum, vascular (arterial or venous) system, cardiac tissues, or the interface between one of these tissues and a synthetic structure such as a patch or vascular graft. Defects for which the implantable medical device may be applied include those that may be natural or artificially created, either intentionally or through some traumatic event or disease process. Defects may include, but are not limited to, perforations, ruptures, wounds, tears, endoleaks, fistulae, and the like.

Additionally, this disclosure provides, inter alia, implantable devices for connecting tissue layers, such as for connecting a gallbladder and a portion of a gastrointestinal tract to create an anastomosis that facilitates material flow therebetween. The devices are endoscopically deployable or deployable via a catheter and can include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein allow treatment to circumvent a conduit or organ blockage by creating a direct passage between tissue structures, such as, for example, the gallbladder and a portion of the gastrointestinal tract. In some embodiments, the devices provided herein are implanted temporarily. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. Such devices can provide an alternative treatment for patients who are not suitable candidates for other types of treatment (e.g., gallbladder removal surgery) and/or to avoid known complications of other types of treatment (e.g., external biliary drainage).

Figure 1B:
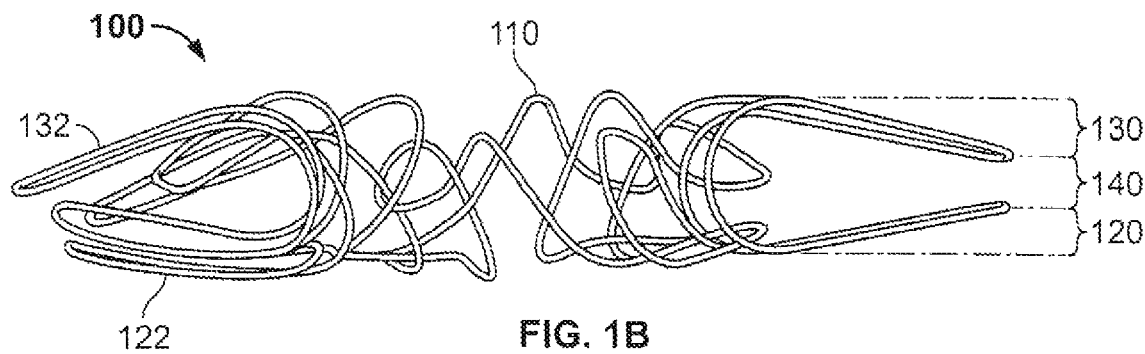
FIG. 1B is an elevation view of the wire frame of FIG. 1A.

In reference to FIGS. 1A and 1B, a frame 100 of an exemplary tissue-sealing device includes an elongate member 110. The elongate member 110 is configured to form an apposition portion 120, a sealing portion 130, and a defect-occupying portion 140. The defect-occupying portion 140 is disposed between the apposition portion 120 and the sealing portion 130. As will be described further, the defect-occupying portion 140 is configured to traverse an opening or aperture in one or more layers of tissue, also referred to herein as a tissue defect. The apposition portion 120 and the sealing portion 130 are configured to be on opposite sides of the layer(s) of tissue. In some embodiments, the elongate member 110 comprises a single continuous wire.

The elongate member 110 can comprise a variety of materials. The elongate member 110 may be elastomeric, metallic, a spring wire, a shape memory alloy wire, a super-elastic alloy wire, or combinations thereof, to name a few general examples. In fact, any type of elongate member 110 that is suitably biocompatible, flexible, and resilient can generally be used for the tissue-sealing devices provided herein. For example, the elongate member 110 can comprise nitinol (NiTi), L605 steel, stainless steel, polymeric materials, or any other appropriate biocompatible material, including combinations of materials. In some embodiments, bioresorbable or bioabsorbable materials may be used, including, for example, a bioresorbable or bioabsorbable polymer. In some such embodiments, the elongate member 110, or portions thereof, may eventually dissolve. In other embodiments, the elongate member 110 is fully or partially coated to stimulate a biological reaction, such as, but not limited to, endothelial cell attachment, endothelial cell migration, endothelial cell proliferation, and resistance to or promotion of thrombosis.

It should be understood that suitable materials for the elongate member 110 include a variety of metallic shape memory materials and super-elastic alloys. Shape memory refers to the ability of a material to revert or substantially revert to an originally memorized shape after plastic deformation by heating above a critical temperature. Super-elasticity refers to the ability of a material to deform under strain to a very large degree, without having this deformation become permanent. For example, the super-elastic materials included in the frames of some tissue-sealing device embodiments provided herein are able to withstand a significant amount of bending and flexing and then return to the frame's original form (or approximately thereto) without deformation. In some embodiments, suitable shape memory and super-elastic materials include various stainless steels which have been physically, chemically, and otherwise treated to produce high springiness, metal alloys such as cobalt chrome alloys (e.g., ELGILOY™), platinum/tungsten alloys, and the NiTi alloys.

The super-elastic properties of NiTi make it a suitable material for the elongate member 110 of some embodiments of the tissue-sealing devices provided herein. NiTi elongate members 110 can be shape-set into a desired shape such that the NiTi elongate member 110 will tend to self-expand from a low-profile delivery configuration into the desired shape when deployed from a delivery sheath to a target site within a body.

In some embodiments, the elongate member 110 can be treated in various ways to increase the radiopacity of the elongate member 110 for enhanced radiographic visualization. In some embodiments, the elongate member 110 is at least partially a drawn-filled type of NiTi containing a different material at the core, such as a material with enhanced radiopacity. In some embodiments, the elongate member 110 has a radiopaque cladding or plating on at least portions of the elongate member 110. In some embodiments, one or more radiopaque markers are attached to the elongate member 110 (and/or to a covering material that is attached to the elongate member 110).

In some embodiments, the diameter or thickness of the elongate member 110 is within a range of about 0.1 mm to about 1.50 mm, but in some embodiments an elongate member 110 having smaller or larger diameters can be used. In some embodiments, the diameter of thickness of the elongate member 110 is within a range of about 0.2 mm to about 0.5 mm. Notwithstanding, it is to be appreciated that the elongate member 110, and the elongate members of other tissue-sealing devices provided herein, can have any suitable size or diameter.

In some embodiments, the elongate member 110 has a consistent diameter along the length of the elongate member 110. In some embodiments, one or more portions of the elongate member 110 are diametrically tapered or otherwise inconsistent in diameter. In some embodiments, the elongate member 110 may be formed using a center-less grinding technique, such that the diameter of the wire varies along the length of the elongate member 110. The elongate member 110 may have a round cross-sectional shape or may have a cross-sectional shape that is not round, such as a rectangle or other polygon. Examples of other cross-sectional shapes that the elongate member 110 may have include a square, oval, rectangle, triangle, D-shape, trapezoid, or irregular cross-sectional shape formed by a braided or stranded construct. In some embodiments, the elongate member 110 may comprise a flat wire. In some embodiments, a combination of such various types of elongate member 110 are used in a tissue-sealing device. While in some embodiments the elongate member 110 of the device has a uniform cross-sectional shape and size, in some embodiments, some portions of the elongate member 110 have a different cross-sectional shape and/or size than other portions of the elongate member 110.

The elongate member 110 of the tissue-sealing devices provided herein may exhibit, for example, beneficial fatigue resistance and elastic properties. In some embodiments, the elongate member 110 allows the tissue-sealing devices to be elastically crushed, folded, and/or collapsed into a low-profile delivery configuration for containment within a lumen for transcatheter or endoscopic/thoracoscopic delivery, and to self-expand to an operative size and configuration once positioned at a desired target site within a body and deployed from the lumen. Further, in some embodiments the elongate member 110 of the frame 100 (and the elongate members of the other frames described herein) can be over-distended without incurring damage to the frame 100. For example, in some embodiments the elongate member 110 is capable of being deformed, such as when an oversized device is placed through the frame 100, and the elongate member 110 will return (or substantially return) to its pre-deformed configuration without sustaining permanent deformation such as wrinkling or folding.

In some embodiments, the elongate member 110 may include one or more fixation elements (e.g., anchors, barbs, protrusions, atraumatic members, and/or penetrating members, and combinations thereof). In exemplary embodiments, such fixation elements advantageously reduce or inhibit in situ migration of the tissue-sealing devices after deployment to a target site within a body.

Still referring to FIGS. 1A and 1B, in some embodiments the apposition portion 120 (also referred to herein as the supporting portion or apposition member) includes multiple features that are configured to contact a surface of a tissue around a defect in the tissue, and to provide an apposition force to the tissue surface. For example, in the embodiment depicted in FIGS. 1A and 1B, the one or more features of the apposition portion 120 include elongate wire loops 122 (also referred to herein as "fingers" or "petals"). While in this embodiment, the apposition portion 120 includes eight wire loops 122, more or fewer than eight wire loops 122 may be included. For example, in some embodiments one, two, three, four, five, six, seven, nine, ten, eleven, twelve, or more than twelve wire loops 122 may be included in the apposition portion 120.

In FIGS. 1A and 1B, the wire loops 122 of the apposition portion 120 are depicted as being generally ovular in shape; however, it should be understood that an ovular shape is not required. For example, in some embodiments the wire loops 122 can be circular, triangular, linear, rectangular, diamond-shaped, and the like, or combinations thereof. For example, in some embodiments the wire loops 122 can have a first linear portion that projects radially from the defect-occupying portion 140 and that is contiguous with a second diamond-shaped portion at the free end of the wire loops 122. Other combinations and are envisioned and are considered to be within the purview of the invention. While in the depicted embodiment the shape and size of all of the individual wire loops 122 is generally uniform, such uniformity is not a requirement. For example, one or more of the wire loops 122 may be shaped or sized differently from one or more other wire loops 122 of the same tissue-sealing device.

In some embodiments, the wire loops 122 are configured to independently bear loads associated with tissue surface contact. That is, individual ones of the wire loops 122 can be independently deflected in accordance with the topography of the tissue surface without imparting a substantial force to any other ones of the wire loops 122. This feature can allow each of the wire loops 122 to provide an appositional force even though the tissue surface topography is not planar. Hence, in some embodiments the apposition portion 120 is configured to be highly conformable to irregular tissue surfaces (refer, e.g., to FIG. 13C). In some embodiments, portions of individual wire loops 122 may overlap with adjacent wire loops 122. In some such embodiments, some movements of the wire loops 122 may induce forces on adjacent wire loops 122.

The elongate member 110 also forms the sealing portion 130 (also referred to herein as the "occluding portion," "central portion," or "sealing member"). As will be described further below, a generally fluid impermeable covering material may be disposed on the sealing portion 130. In some embodiments, the sealing portion 130 includes one or more features that are configured to contact a surface of a tissue around a defect in the tissue, and to provide an apposition force to the tissue surface. For example, in the embodiment shown in FIGS. 1A and 1B, the one or more features of the sealing portion 130 include elongate wire loops. Although eight wire loops 132 are shown, it is to be appreciated that more or fewer that eight wire loops 132 may be included. For example, in some embodiments one, two, three, four, five, six, seven, nine, ten, eleven, twelve, or more than twelve wire loops 132 may be included in the apposition portion 130. Additionally, the number of wire loops 122 of the apposition portion 120 may be unequal to the number of wire loops 132 of the sealing portion 130. Further, the shape of the wire loops 122 of the apposition portion 120 may be different than the shape of the wire loops 132 of the sealing portion 130.

Although the embodiment depicted in FIGS. 1A and 1B depicts the wire loops 132 of the sealing portion 130 are having a generally ovular shape, it should be understood that the ovular shape is not required. For example, in some embodiments, the wire loops 132 can be circular, triangular, linear, rectangular, diamond-shaped, and the like, and combinations thereof. For example, in some embodiments the wire loops 132 can have a first linear portion that projects radially from the defect-occupying portion 140, and a second diamond-shaped portion at the free end of the wire loops 132. Other combinations and shapes are also envisioned and are considered to be within the purview of the invention. In addition, in the embodiment depicted in FIGS. 1A and 1B the shape and size of each of the wire loops 132 generally uniform. However, it should be understood that such uniformity is not a requirement. For example, in some embodiments one or more of the wire loops 132 are shaped or sized differently from one or more other wire loops 132.

In some embodiments, the wire loops 132 are configured to independently bear loads associated with tissue surface contact. That is, individual ones of the wire loops 132 can be independently deflected in accordance with the topography of the tissue surface without imparting a substantial force to any other ones of the wire loops 132. This feature can allow each of the wire loops 132 to provide an appositional force even though the tissue surface topography is non-planar. Hence, in some embodiments the sealing portion 130 is configured to be highly conformable to irregular tissue surfaces (refer, e.g., to FIG. 13D). In some embodiments, portions of individual wire loops 132 may overlap with adjacent wire loops 132. In some such embodiments, some movements of the wire loops 132 may induce forces on adjacent wire loops 132.

In some embodiments, at least portions of the wire loops 132 are configured to overlap with each other. That is, at least portions of individual ones of the wire loops 132 can overlap with at least portions of the other wire loops 132 that are adjacent thereto. In some embodiments, such overlap may enhance the sealing capabilities of the sealing portion 130.

While in the depicted embodiment of FIGS. 1A and 1B, the apposition portion 120 and the sealing portion 130 each define a generally circular circumference around their peripheries, a circular shape is not required in all embodiments. For example, in some embodiments the periphery of either of the apposition portion 120 or the sealing portion 130 (or both) can define other shapes such as, but not limited to, an ellipse, rectangular, triangular, and other geometric or regular or irregular shapes.

Figure 10A:
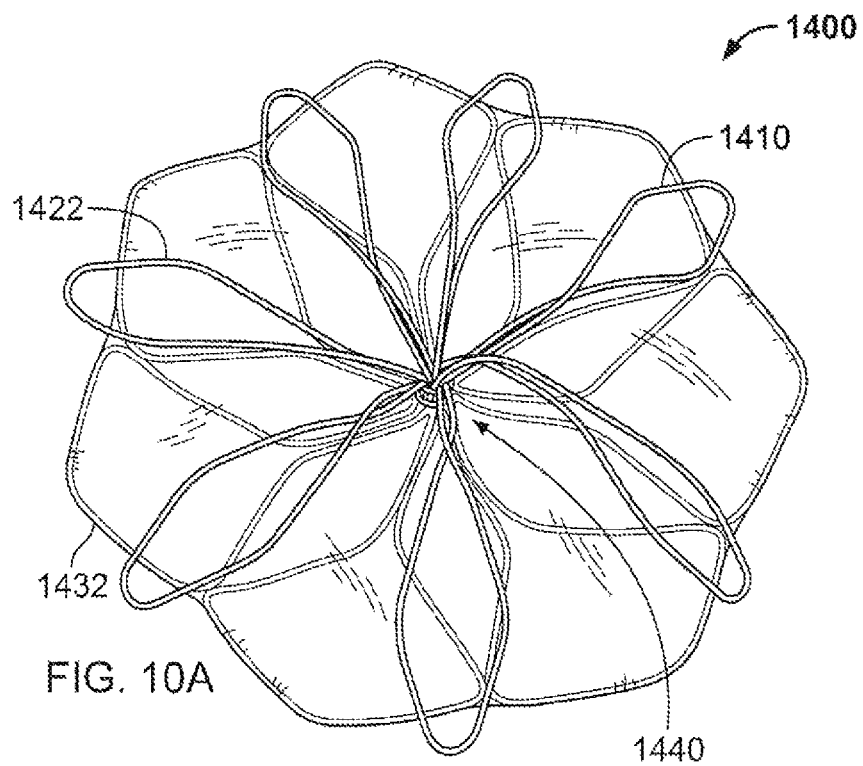
FIG. 10A is a plan view of another exemplary sealing device in accordance with some embodiments.
Figure 10B:
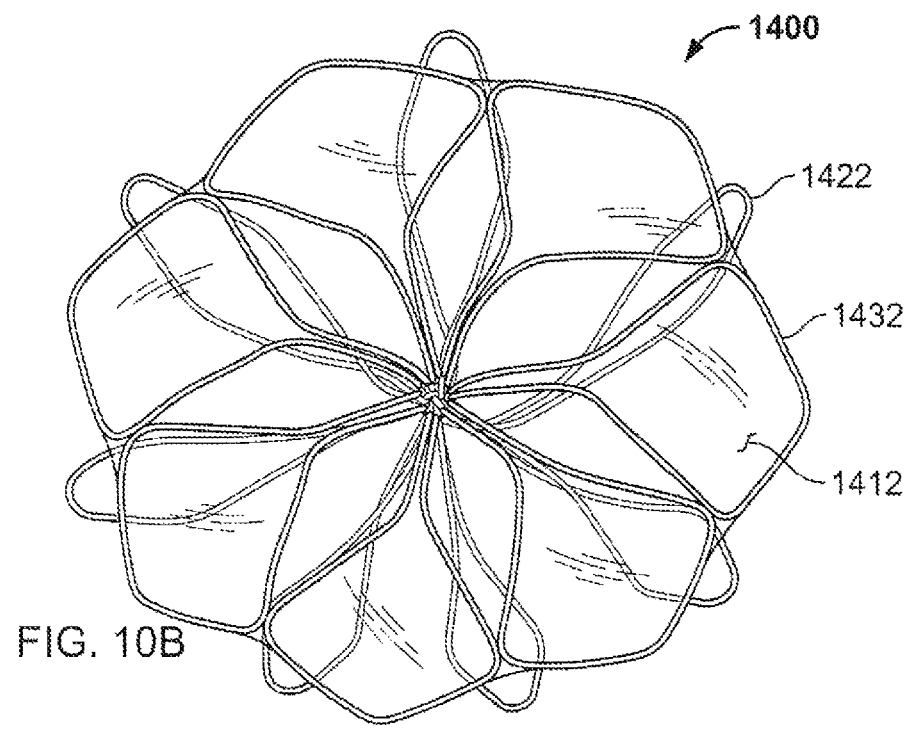
FIG. 10B is another plan view of the sealing device of FIG. 10A.
Figure 11A:
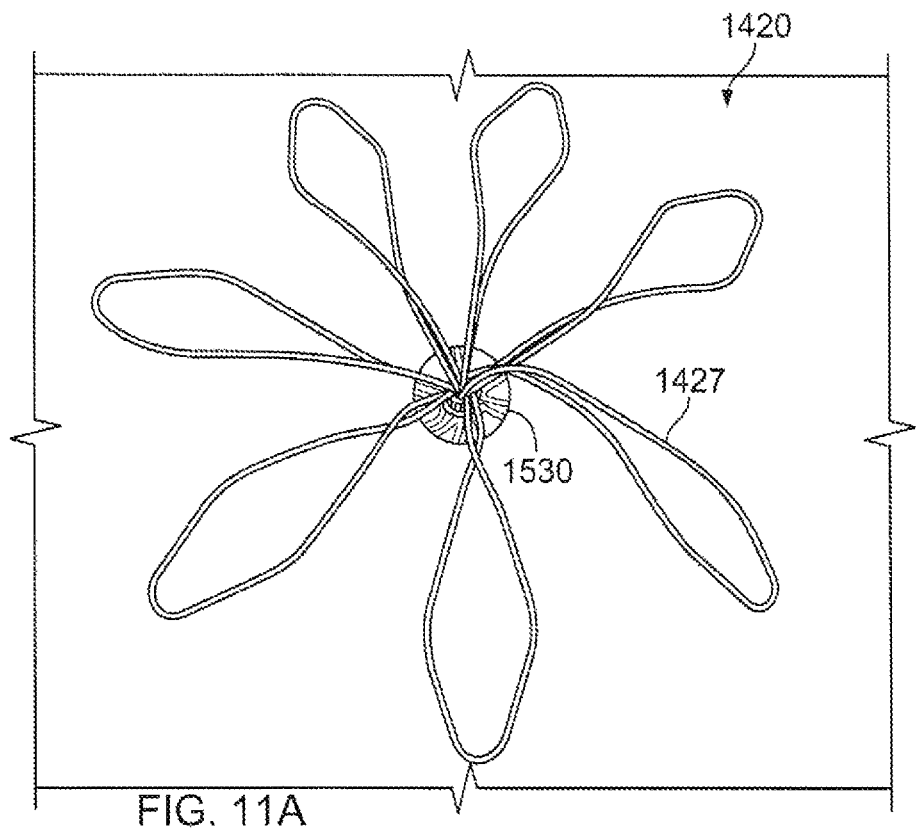
FIG. 11A is a plan view of the sealing device of FIG. 10A engaged in an exemplary tissue defect.
Figure 11B:
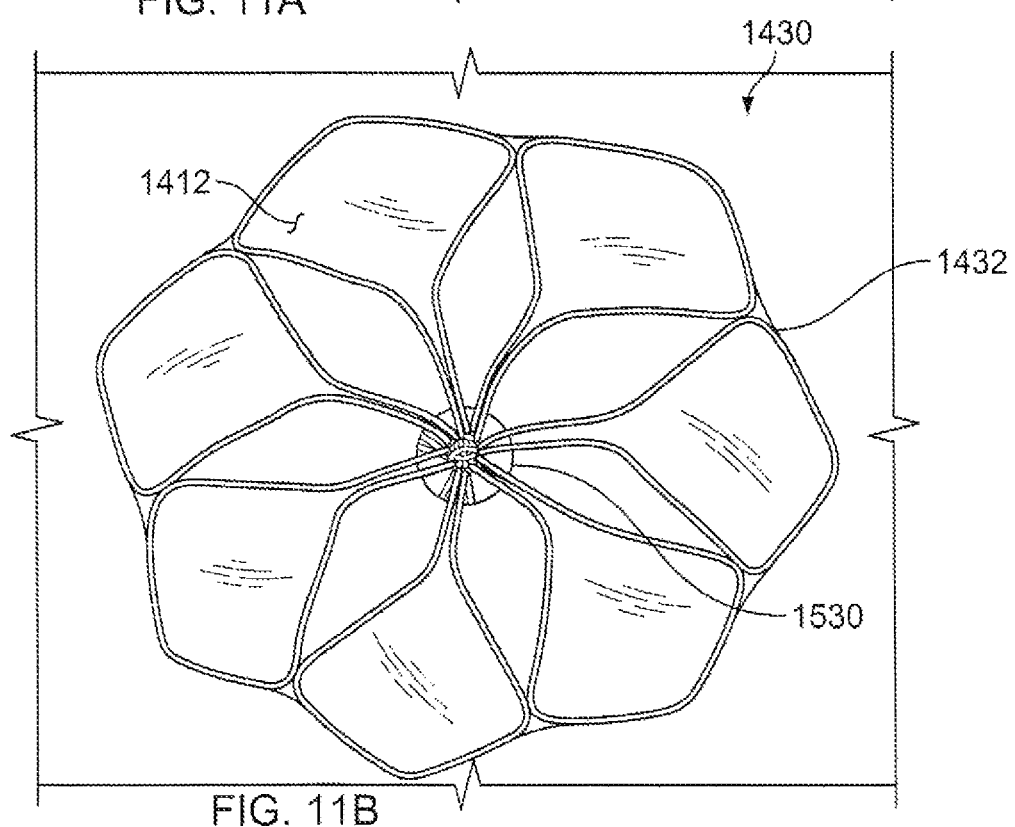
FIG. 11B is another plan view of the sealing device of FIG. 10A engaged in an exemplary tissue defect.

In some embodiments, the wire loops 122 of the apposition portion 120 and corresponding wire loops 132 of the sealing portion 130 are not parallel. For example, in some embodiments the distance between the free ends of the wire loops 122 and 132 is less than the distance between the wire loops 122 and 132 near the defect-occupying portion 140 (e.g., as shown in FIG. 1B). Such a configuration provides an increased level of apposition force at the outer radius of the frame 100 as compared to the apposition force nearer to the defect-occupying portion 140. In some embodiments, the increased level of apposition force at the outer radius of the frame 100 can, in turn, facilitate conformance by the frame 100 to a significantly non-planar and irregular tissue surface. In some embodiments, to increase the level of apposition force provided by the frame 100. Further, the distance between the free ends of the wire loops 122 and 132 can be reduced to essentially zero. In some embodiments, to increase the apposition force provided by the frame 100 still further, the wire loops 122 and 132 can cross over each other (e.g., refer to FIG. 10).

As described above, in some embodiments the elongate member 110 (and the elongate members of some embodiments of the other devices described herein) is a single continuous element. Accordingly, the elongate member 110 includes two free ends or termini. In some embodiments, the two free ends of the elongate member 110 can be conjoined such that the elongate member 110 forms a closed wind pattern (i.e., a continuous loop). The free ends of the elongate member 110 can be joined together using a variety of techniques including, but not limited to bonding, welding (e.g., laser welding), gluing, using a sleeve coupling, and the like, and combinations thereof. In some embodiments, a butt joint is used to join the free ends of the elongate member 110. In some embodiments, other types of joints can be used to join the free ends of the elongate member 110, including but not limited to, an overlap joint, a twist joint, a crimp joint, and the like, and combinations thereof. The free ends can be conjoined prior to or after heat-setting (in those embodiments that use a heat-setting process). In some embodiments, the free ends are not conjoined.

Referring now to FIGS. 1A-1B and 2A-2B, a covering material 210 (also referred to herein as a sealing material or a membrane) can be disposed on or around and/or attached to at least a portion of the sealing portion 130. In addition, the covering material 210 is attached to the sealing portion 130 of the frame 100 to create the tissue-sealing device 200. The tissue-sealing device 200 is shown sealing a large tissue aperture 230 in FIG. 2A, and the same tissue-sealing device 200 is shown sealing a smaller tissue aperture 270 in FIG. 2B. Such tissue defects 230 and 270 can result from a number of causes, such as a resection to remove a lesion, a burst aneurysm, a trauma-induced hole or tear, a fistula, diseases such as appendicitis or diverticulitis, Crohn's disease, and ulcers, to provide a few non-limiting examples.

Figure 2A:
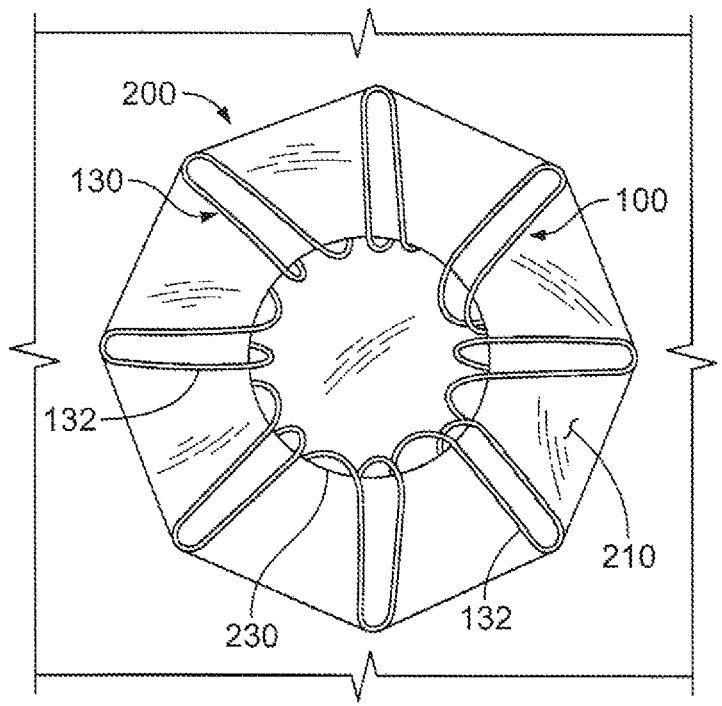
FIG. 2A is a plan view depicting the wire frame of FIG. 1A having thereon a covering material and engaged in an exemplary tissue defect.
Figure 2B:
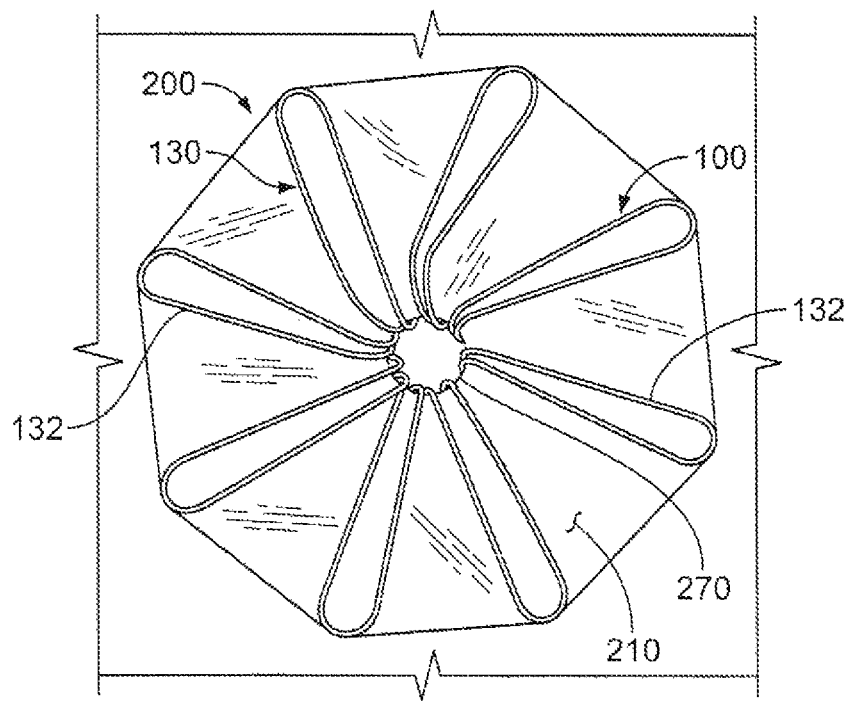
FIG. 2B is a plan view showing the wire frame of FIG. 1A having thereon a covering material and engaged in another exemplary tissue defect.

FIGS. 2A and 2B illustrate how the design of the tissue-sealing device 200 advantageously lends itself to sealing a wide variety of differently-sized and shaped apertures 230 and 270. This is accomplished, at least in part, because the defect-occupying portion 140 is configured to exert a low level of radial force to the perimeter tissue of the tissue apertures 230 and 270. Additionally, the appositional force that provides sealing and migration resistance is substantially delivered by the apposition portion 120 and the sealing portion 130, rather than the defect-occupying portion 140. In some embodiments the appositional forces provided by the apposition portion 120 and the sealing portion 130 are substantially independent of the in situ device shape or diameter, thus providing reliable sealing across a wide variety of anatomies, and for dynamic anatomies (e.g., such as the GI tract).

The tissue-sealing device 200 may be configured to be implanted in a patient such that the covering material 210 fully overlays and seals the tissue apertures 230 and 270. For example, the covering material 210 may be disposed on the sealing portion 130, but not on the apposition portion 120, nor the defect-occupying portion 140. However, in some embodiments the covering material 210 may be disposed on all or portions of the apposition portion 120 and/or the defect-occupying portion 140 in addition to the sealing portion 130.

In one exemplary embodiment, tissue-sealing device 200 is used to occlude/seal a defect in the wall of a body lumen such as an intestine or blood vessel. In such a case, tissue-sealing device 200 is deployed so that the sealing portion 130 with the covering material 210 is positioned on the inside of the body lumen. In that orientation, materials that are contained within the body lumen are occluded, i.e., prevented from leaking from the body lumen. In addition, in that orientation, the tissue-sealing device 200 provides separation of intralumenal materials from the defect. The separation can, in some scenarios, allow healing of the defect, because contact of the biomaterials to the defect may tend to inhibit or prevent the healing process of the tissue surrounding the defect. For example, fecal matter within a colon would tend to inhibit the healing process of a perforation in the colon wall. In such circumstances, the tissue-sealing device 200 can be temporarily implanted in the colon such that the covering material 210 overlays the perforation of the colon wall. In result, the perforation will be sealed by the tissue-sealing device 200 such that fecal matter will not escape from the colon to contaminate other portions of the body, and the tissue surrounding the perforation will be isolated from fecal matter so that the tissue's healing process will not be inhibited. After the perforation has healed and/or closed, the tissue-sealing device 200, or portions thereof, can be removed from the patient. Alternatively, tissue-sealing device 200, or portions thereof, may be naturally expelled by the body. In some embodiments, the tissue-sealing device 200 may be implanted permanently.

In addition, in some embodiments, portions of the tissue-sealing device 200 are retrievable while other portions will remain at the defect site. For example, in some embodiments portions of the covering material 210 can provide a scaffold for tissue ingrowth or endothelialization to allow healing of the defect. Then, those portions of the covering material 210 can be made to separate from the tissue-sealing device 200 and stay at the defect site when the other parts of the tissue-sealing device 200 are retrieved from the patient's body. In some embodiments, the tissue-sealing device 200, or portions thereof, are bioabsorbable such that the structure of the tissue-sealing device 200 will deteriorate in time. For example, in some such embodiments portions of the elongate member 110 may deteriorate by bioabsorption, after which other portions of the tissue-sealing device 200 may be naturally expelled from the GI tract, or otherwise retrieved. In some cases, the elongate member 110 may need to be severed in one or more locations prior to removal from the body. That may be the case, for example, when tissue growth has engulfed portions of the elongate member 110.

In some embodiments, the covering material 210 is made of a membranous material that inhibits or reduces passage of blood, and other bodily fluids and substances. In some embodiments, the covering material 210 has a material composition and configuration that inhibits or prevents endothelialization and tissue ingrowth to the covering material 210. Such a feature may be advantageous, for example, for scenarios in which the tissue-sealing device 200 is intended to be implanted temporarily in a patient and then retrieved from the patient.

In some embodiments, the covering material 210, or portions thereof, has a microporous structure that promotes endothelialization and/or provides a tissue ingrowth scaffold for durable sealing and/or supplemental anchoring strength of the sealing device. Such a feature may be advantageous, for example, for scenarios in which the tissue-sealing device 200 is intended to be implanted in the patient for a long term or permanently.

In some embodiments, the covering material 210 comprises a fluoropolymer, such as an expanded polytetrafluoroethylene (ePTFE) polymer. In some embodiments, the covering material 210 comprises a polyester, a silicone, a urethane, other biocompatible polymer(s), Dacron, bioabsorbable systems, copolymers, or combinations thereof.

In some embodiments, the covering material 210, or portions thereof, used in the tissue-sealing device 200 and other tissue-sealing device embodiments is modified by one or more chemical or physical processes that enhance one or more properties of the materials. For example, in some embodiments, a hydrophilic coating may be applied to the covering material 210 to improve the wettability and echo translucency of the material 210. In some embodiments the covering material 210, or portions thereof, may be modified with chemical moieties that promote one or more of endothelial cell attachment, endothelial cell migration, endothelial cell proliferation, and resistance to or promotion of thrombosis. In some embodiments the covering material 210, or portions thereof, may be modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance is a corticosteroid, a human growth factor, an anti-mitotic agent, an antithrombotic agent, a stem cell material, or dexamethasone sodium phosphate, to name some examples. In some embodiments, a pharmacological agent is delivered separately from the covering material 210 to the target site to promote healing of the tissue defect.

Coatings and treatments may be applied to the covering material 210 before or after the covering material 210 is joined or disposed on the frame 100 of the tissue-sealing device 200. Additionally, one or both sides of the covering material 210, or portions thereof, may be coated. In some embodiments, certain coatings and/or treatments are applied to the material(s) located on some portions of the tissue-sealing device 200, and other coatings and/or treatments are applied to the material(s) located on other portions of the tissue-sealing device 200. In some embodiments, a combination of multiple coatings and/or treatments are applied to the covering material 210, or portions thereof. In some embodiments, certain portions of the tissue-sealing device 200 are left uncoated and/or untreated.

In some embodiments, a first portion of the covering material 210 is formed of a first material and a second portion of the covering material 210 is formed of a second material. In some embodiments, the covering material 210 is comprised of multiple layers of materials, which may be the same or different materials. In some embodiments, portions of the covering material 210 have one or more radiopaque markers attached thereto to enhance in vivo radiographic visualization of the tissue-sealing device 200.

In some embodiments, at least a portion of the covering material 210 is attached to the elongate member 110 of the sealing portion 130. The attachment can be accomplished by a variety of techniques, such as by stitching the covering material 210 to the sealing portion 130, by adhering the covering material 210 to the sealing portion 130, by laminating multiple layers of the covering material 210 to encompass the sealing portion 130, by using clips or barbs, or by other such techniques or combinations thereof. In some embodiments, the elongate member 110 of the sealing portion 130, or portions thereof, may be coated with a bonding agent, for example fluorinated ethylene propylene (FEP) or other suitable adhesive for bonding the covering material 210 to the sealing portion 130. The adhesive may be applied through contact coating, powder coating, dip coating, spray coating, or any other appropriate means. The sealing portion 130 thereby provides a supportive structural framework for the covering material 210 that may be otherwise relatively flaccid.

The design of the tissue-sealing device 200 facilitates a durable ongoing seal of a defect in a body lumen wall, notwithstanding the fact that some anatomical environments in which the tissue-sealing device 200 may be used are dynamic, such as the dynamic peristaltic motion environment of the GI tract. The tissue-sealing device 200 includes design features that facilitate the seal even in such dynamic environments. For example, the tissue-sealing device 200 is highly flexible and therefore highly conformable to irregular tissue topography. Furthermore, the apposition forces provided by the apposition portion 120 and the sealing portion 130 are substantially independent of the in situ device shape and/or diameter. In some embodiments, one or more auxiliary tissue anchorage features (e.g., anchors, barbs, protrusions, atraumatic members, and/or penetrating members, and combinations thereof) are included on the elongate member 110. Such anchorage features can provide increased fixation and to resistance to migration of the tissue-sealing device 200 within the body.

As will be described further below, the configuration of the tissue-sealing device 200 (and other tissue-sealing device embodiments and anastomosis device embodiments provided herein), as well as the flexibility and elasticity of the elongate member 110, make the tissue-sealing device 200 capable of transcatheter deployment. That is, in some embodiments the tissue-sealing device 200 can be elastically collapsed to a low-profile configuration for temporary containment within a lumen of a delivery catheter or sheath. To deploy the tissue-sealing device 200, the sheath containing the tissue-sealing device 200 in the low-profile configuration is inserted into the body of a patient and directed to a target site—typically using radiographic visualization (e.g., fluoroscopy), or using endoscopic optics for direct visualization. At the target site, the tissue-sealing device 200 is caused to emerge and become liberated from the sheath (e.g., using a pusher catheter), after which the tissue-sealing device 200 self-expands, or is caused to expand, to an enlarged configuration. For example, FIGS. 1A and 1B show the frame 100 of the tissue-sealing device 200 in the enlarged configuration that the frame 100 will naturally tend to seek in the absence of external constraining forces, such as those forces from a delivery sheath.

It should be understood that when the tissue-sealing device 200 (and the other devices described herein) is deployed in a patient's body, there will typically be constraining forces applied to the tissue-sealing device 200, such as from the tissue and tissue aperture in which the tissue-sealing device 200 resides. Because of those constraining forces, the shape of the tissue-sealing device 200 within the body may tend to be different than the shapes shown in the figures of the instant disclosure. Said another way, when the tissue-sealing device 200 is deployed within the body, the tissue-sealing device 200 will try to expand to its natural fully enlarged configuration, but the tissue-sealing device 200 may be constrained by the contours of the anatomy at the target site. In such circumstances, the shape of the tissue-sealing device 200 will tend to conform to the contours of the anatomy.

After the original deployment of the tissue-sealing device 200 at the target site, the contours of the anatomy may change over time. For example, if the tissue-sealing device 200 is deployed within the GI tract, the peristaltic wave motion of the intestines may change the contours of the anatomy at the target site. In that circumstance, the flexibility and elasticity of the tissue-sealing device 200 can allow the elongate member 110 to adapt in shape to thereby facilitate resilient ongoing contact between the covering material 210 and the tissue surrounding the tissue defect.

Figure 3A:
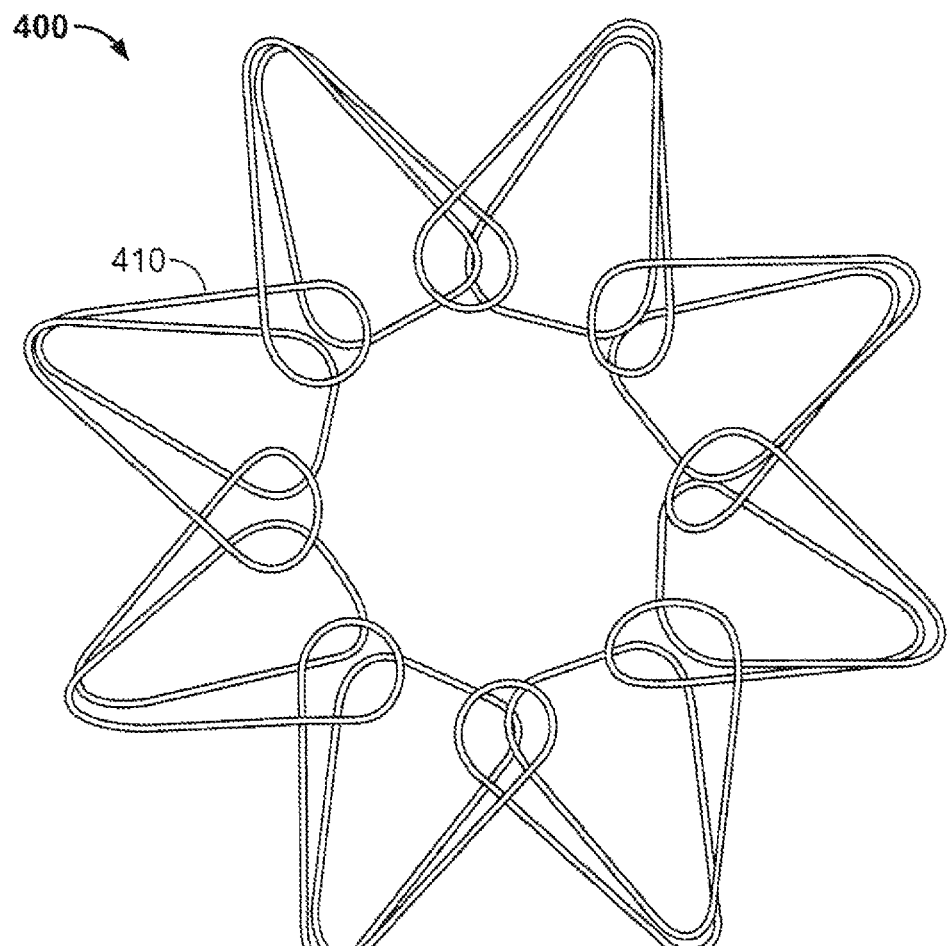
FIG. 3A is a plan view of a wire frame of another exemplary tissue-sealing device in accordance with some embodiments.
Figure 3B:
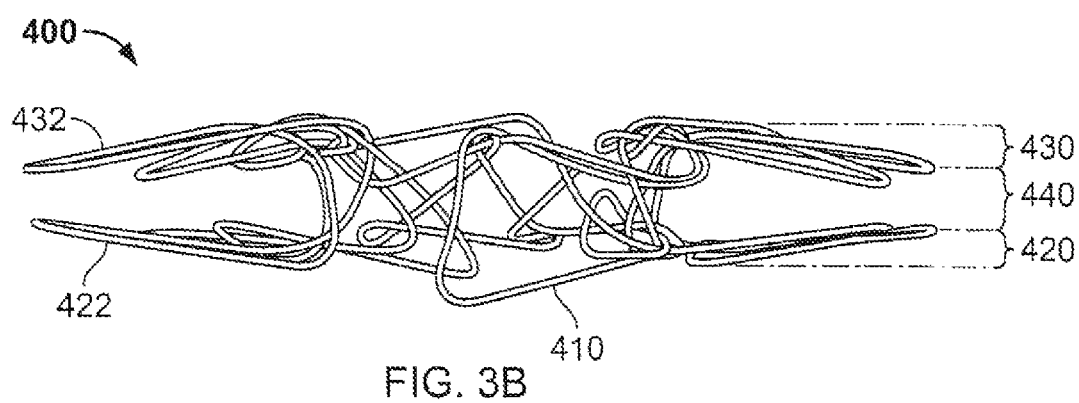
FIG. 3B is an elevation view of the wire frame of FIG. 3A.

With reference to FIGS. 3A and 3B, a frame 400 of another exemplary tissue-sealing device includes an elongate member 410. The elongate member 410 forms an apposition portion 420, a sealing portion 430, and a defect-occupying portion 440. The defect-occupying portion 440 is disposed between the apposition portion 420 and the sealing portion 430. The defect-occupying portion 440 is configured to traverse an opening or aperture in one or more layers of tissue. The apposition portion 420 and the sealing portion 430 are configured to be on opposite sides of the layer(s) of tissue. In some embodiments, the elongate member 410 comprises a single continuous wire that was formed to define the frame 400. The elongate member 410 defines apposition petals 422 that comprise the apposition portion 420, and sealing petals 432 that comprise the sealing portion 430. In the depicted embodiment, the apposition petals 422 and the sealing petals 432 are shaped essentially as triangles. In some embodiments, a variety of different shapes and/or combinations of different shapes can be used for the petals 422 and 432.

The frame 400 can share many of the same features and characteristics as described above in reference to frame 100. However, one difference (in addition to the shape of the petals 422 and 432 as previously described) is that the wind pattern of the elongate member 410 results in a partial overlap of adjacent petals 422 and 432. To be clear, the elongate member 410 is formed so that an individual apposition petal 422 partially overlaps with its adjacent apposition petals 422 on both sides of the individual apposition petal 422. Similarly, the elongate member 410 is formed so that an individual sealing petal 432 partially overlaps with the adjacent sealing petals 432 on both sides of the individual sealing petal 432. Such overlap of the adjacent sealing petals 432 can provide enhanced sealing performance in some embodiments.

It should be understood from the description herein that, while the apposition portion 420 and the sealing portion 430 of the frame 400 are equivalently sized and shaped in the depicted embodiment, such similarities are not required. For example, in one non-limiting example, a frame of a tissue-sealing device can include an apposition portion comprised of the wire loops 122 of the frame 100 (referring to FIGS. 1A and 1B) and a sealing portion comprised of the sealing petals 432 of the frame 400. All combinations of shapes, sizes, patterns, components, features, etc. of one tissue-sealing device embodiment can be combined with all other shapes, sizes, patterns, components, features, etc. of all other tissue-sealing device embodiments described herein to create numerous iterations of hybrid tissue-sealing devices in addition to the individual embodiments described herein.

Figure 4:
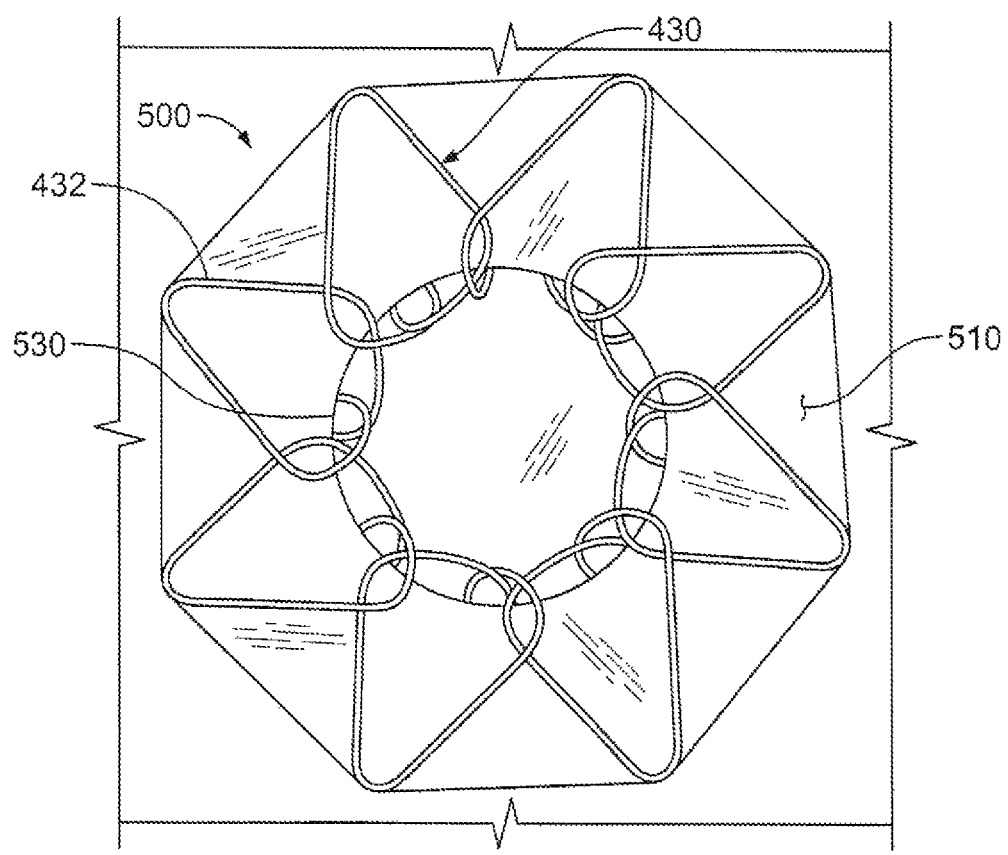
FIG. 4 is a plan view showing the wire frame of FIG. 3A having thereon covering material and engaged in an exemplary tissue defect.

With reference to FIG. 4, a covering material 510 can be disposed on or around and/or attached to at least a portion of the elongate member 410 that includes the sealing portion 430. The covering material 510 may be attached to sealing petals 432 of the sealing portion 430 to create an exemplary tissue-sealing device 500. The tissue-sealing device 500 is shown in FIG. 4 as sealing a tissue aperture 530.

The covering material 510 can be a material as described above in reference to covering material 210. The covering material 510 can be attached to the elongate member 410 as described above in reference to the attachment of covering material 210 to elongate member 110.

While the exemplary tissue aperture 530 is depicted as generally circular, it should be understood that the design of the tissue-sealing device 500 (and other tissue-sealing device embodiments described herein) advantageously lends itself to sealing a wide variety of differently-sized and shaped apertures 530. That is accomplished in part because the defect-occupying portion 440 is configured to exert a low level of radial force to the tissue aperture 530. Additionally, the appositional force for sealing and migration resistance is substantially delivered by the apposition portion 420 and the sealing portion 430, rather than the defect-occupying portion 440. In fact, in some embodiments the appositional forces delivered by the apposition portion 420 and the sealing portion 430 are substantially independent of the in situ device shape or diameter, thus providing reliable sealing across a wide variety of anatomies, and for dynamic anatomies (e.g., such as the GI tract).

The tissue-sealing device 500 is configured to be implanted in a patient such that the covering material 510 fully overlays and seals the tissue aperture 530. In the embodiment depicted in FIG. 4, the covering material 510 is disposed on the sealing portion 430, but not on the apposition portion 420, nor the defect-occupying portion 440. However, in some embodiments the covering material 510 may be disposed on all or portions of the apposition portion 420 and/or the defect-occupying portion 440 in addition to the sealing portion 430.

With reference to FIGS. 3A, 3B, in some embodiments, the elongate member 410 can be wound into the aforementioned shape to create frame 400 using a winding mandrel. In some embodiments, after winding the elongate member 410 on the mandrel, the assembly can be heated to induce a memory shape in the elongate member 410 corresponding to the shape of the frame 400 as-wound on the mandrel. Also, the two free ends of the elongate member 410 can be conjoined as described above.

Figure 6:
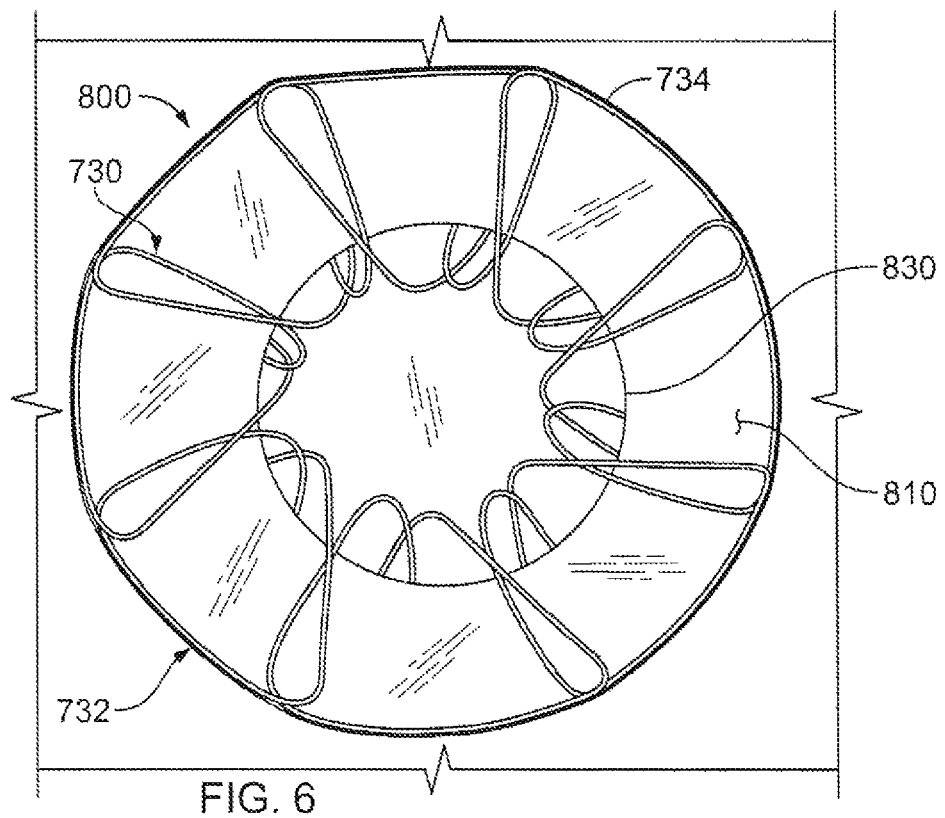
FIG. 6 is a plan view showing the wire frame of FIG. 5 having thereon a covering material and engaged in an exemplary tissue defect.

With reference to FIG. 6, another exemplary tissue-sealing device 800 including a frame 700 and a covering material 810 is illustrated. The covering material 810 is disposed on at least on a sealing portion 730 of the frame 700. The tissue-sealing device 800 is shown sealing an exemplary tissue aperture 830.

The elongate member 710 forms the frame 700 that includes an apposition portion 720, a sealing portion 730, and a defect-occupying portion 740. In the embodiment depicted in FIGS. 5 and 6, the apposition portion 720 and the sealing portion 730 are mirror images of each other. However, such mirror imagery is not required. Thus, in some embodiments, the apposition portion 720 and the sealing portion 730 are configured dissimilarly. The defect-occupying portion 740 is disposed between the apposition portion 720 and the sealing portion 730. Additionally, the defect-occupying portion 740 is configured to traverse the defect or aperture 830 in one or more layers of tissue. The apposition portion 720 and the sealing portion 730 are configured to be on opposite sides of the layer(s) of tissue.

In some embodiments, the elongate member 710 includes a single continuous wire that has been bent to form the frame 700. The elongate member 710 defines apposition petals 722 that form the apposition portion 720, and sealing petals 732 that form the sealing portion 730. In the embodiment shown in FIGS. 5 and 6, the apposition petals 722 and the sealing petals 732 are shaped essentially as trapezoids. In other embodiments, different shapes and combinations of different shapes can be used for the petals 722 and 732.

The frame 700 can share many of the same features and characteristics as described above in reference to frames 100 and 400. However, one difference (in addition to the shape of the petals 722 and 732) is that the wind pattern of the elongate member 710 results in a peripheral frame 724. To be clear, the elongate member 710 is wound so that combined portions of the elongate member 710 define an apposition portion peripheral frame 724. Similarly, the elongate member 710 is wound so that combined portions of the elongate member 710 define a sealing portion peripheral frame 734. Having a sealing portion peripheral frame 734 can provide enhanced sealing performance in some embodiments.

It should be understood from the description herein that, although the apposition portion 720 and the sealing portion 730 of the frame 700 may be equivalently sized and shaped, such similarities are not required. For instance, in one non-limiting example, a frame of a tissue-sealing device may include an apposition portion including the wire loops 122 of the frame 100 (referring to FIGS. 1A and 1B), a sealing portion comprised of the sealing petals 732, and the sealing portion peripheral frame 734 of the frame 700. It is to be appreciated that all combinations of shapes, sizes, patterns, components, features, etc. of one tissue-sealing device embodiment can be combined with any other shapes, sizes, patterns, components, features, etc. of all other tissue-sealing device embodiments to create numerous iterations of hybrid tissue-sealing devices in addition to the individual embodiments described herein.

The covering material 810 may be a material as described above in reference to covering material 210. The covering material 810 can be attached to or disposed on the elongate member 710 as described above in reference to the attachment of covering material 210 to elongate member 110.

While the exemplary tissue aperture 830 is depicted as generally circular, it should be understood that the design of the tissue-sealing device 800 (and other embodiments described herein) advantageously lends itself to sealing a wide variety of differently-sized and shaped apertures 830. This is accomplished in part because the defect-occupying portion 740 is configured to exert a low level of radial force to the tissue aperture 830. Additionally, the appositional force for sealing and migration resistance is substantially provided by the apposition portion 720 and the sealing portion 730, rather than the defect-occupying portion 740. In fact, in some embodiments, the appositional forces provided by the apposition portion 720 and the sealing portion 730 are substantially independent of the in situ device shape or diameter, thus providing reliable sealing across a wide variety of anatomies, and for dynamic anatomies (e.g., such as the GI tract).

The tissue-sealing device 800 is configured to be implanted in a patient such that the covering material 810 fully overlays and seals the tissue aperture 830. In the depicted embodiment, the covering material 810 is disposed on the sealing portion 730, but not on the apposition portion 720, nor the defect-occupying portion 740. However, in some embodiments the covering material 810 can be disposed on all or portions of the apposition portion 720 and/or the defect-occupying portion 740 in addition to the sealing portion 730.

Figure 5:
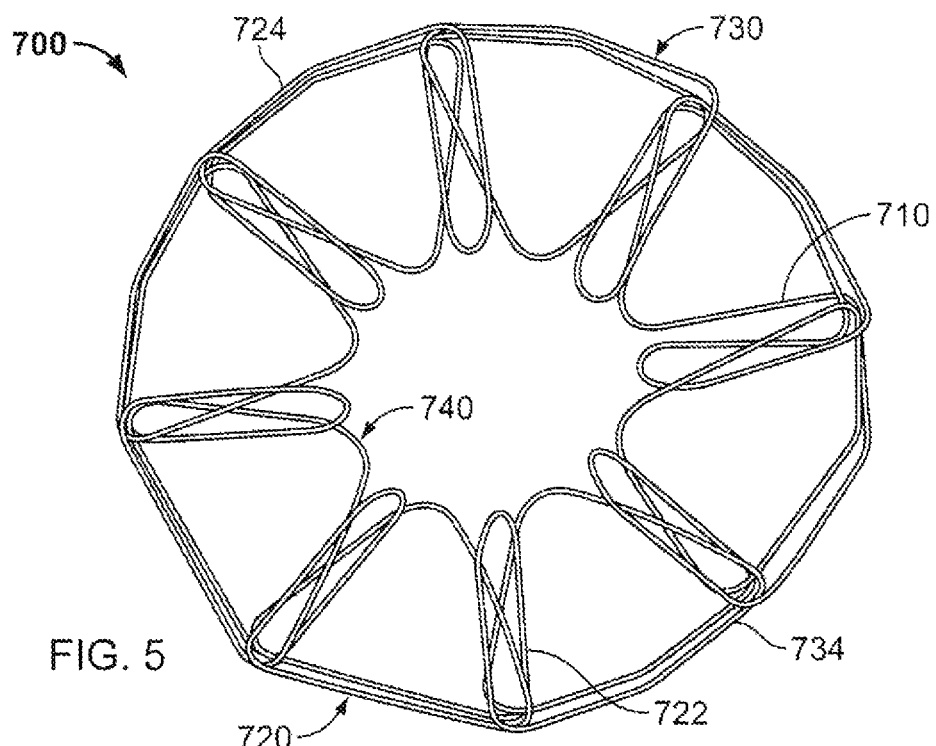
FIG. 5 is a plan view of a wire frame of another exemplary tissue-sealing device in accordance with some embodiments.

With reference to FIGS. 5 and 6, in some embodiments the elongate member 710 may be wound into the aforementioned shape to create frame 700 using a winding mandrel. After winding the elongate member 710 on the mandrel, the assembly can be heated to induce a memory shape in the elongate member 710 corresponding to the shape of the frame 700 as-wound on the mandrel. Also, the two free ends of the elongate member 710 can be conjoined as described above.

Figure 7:
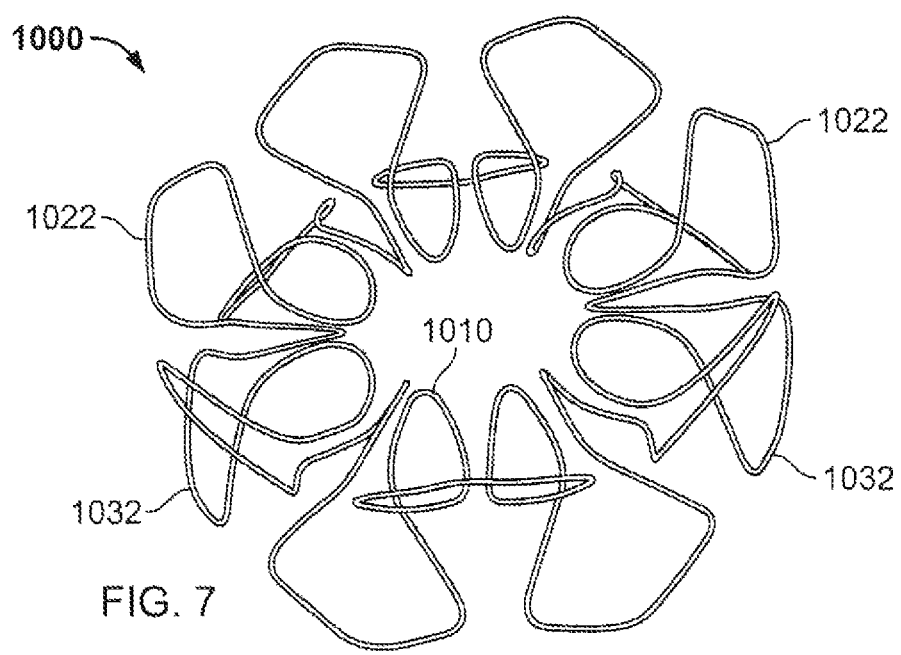
FIG. 7 is a perspective view of a wire frame of another exemplary tissue-sealing device in accordance with some embodiments.
Figure 8A:
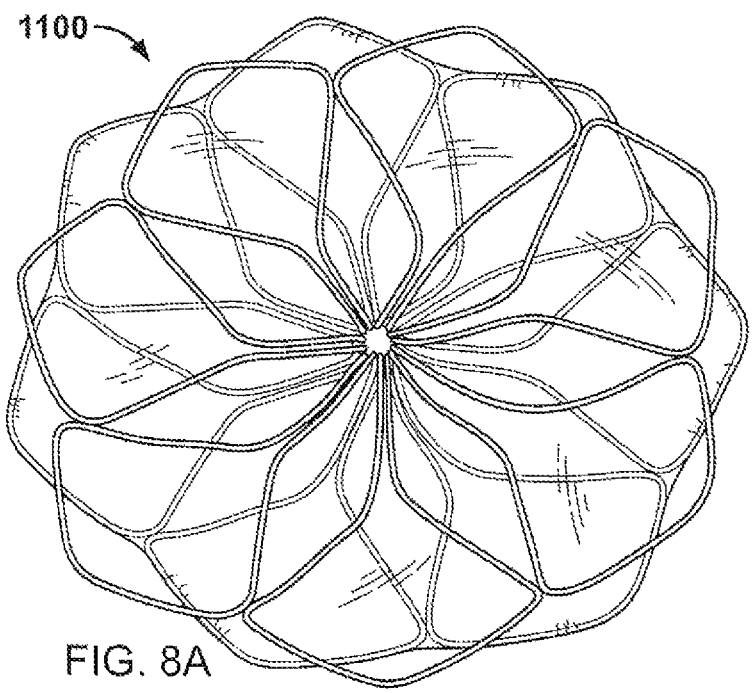
FIG. 8A is a perspective view of an exemplary sealing device made of the wire frame of FIG. 7 having a covering material disposed on an occluding portion of the wire frame.
Figure 8B:
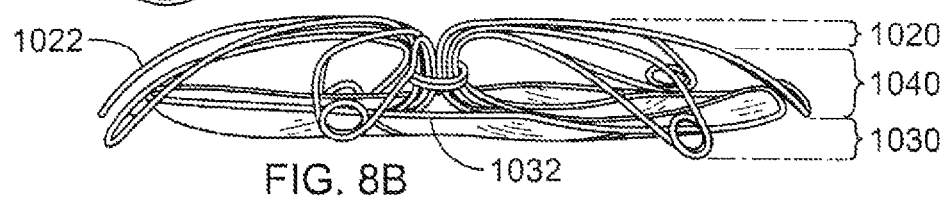
FIG. 8B is an elevation view of the sealing device of FIG. 8A.
Figure 8C:
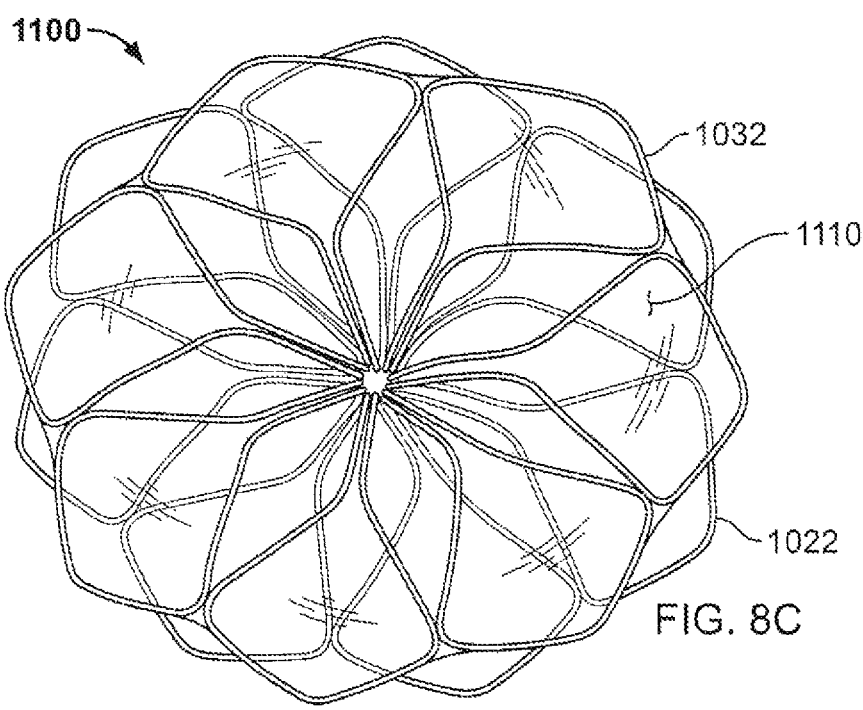
FIG. 8C is another perspective view of the sealing device of FIG. 8A.

With reference to FIGS. 7, 8A-8C, and 9A-9D another exemplary tissue-sealing device 1100 includes a frame 1000 and a covering material 1110. The covering material 1110 is disposed at least on a sealing portion 1030 of the frame 1000. The tissue-sealing device 1100 is shown sealing an exemplary tissue aperture 1230. FIG. 7 is an illustration of the frame 1000 prior to attachment of the covering material 1110 thereto The elongate member 1010 forms the frame 1000 that includes an apposition portion 1020, a sealing portion 1030, and a defect-occupying portion 1040. In the depicted embodiment, the elongate member 1010 is formed so that the apposition portion 1020 and the sealing portion 1030 are mirror images of each other, however such mirror imagery is not required. Thus, in some embodiments, the apposition portion 1020 and the sealing portion 1030 are configured dissimilarly. The defect-occupying portion 1040 is disposed between the apposition portion 1020 and the sealing portion 1030. Additionally, the defect-occupying portion 1040 is configured to traverse the defect or aperture 1230 in one or more layers of tissue. The apposition portion 1020 and the sealing portion 1030 are configured to be on opposite sides of the layer(s) of tissue.

In some embodiments, the elongate member 1010 comprises a single continuous wire that was formed in the shape of the frame 1000. The elongate member 1010 defines one or more apposition petals 1022 that form the apposition portion 1020, and one or more sealing petals 1032 that form the sealing portion 1030. In the depicted embodiment, the apposition petals 1022 and the sealing petals 1032 include a linear portion extending radially from the defect-occupying portion 1040 and an essentially diamond-shaped outer portion extending from the linear portion at the free ends of the petals 1022 and 1032. In some embodiments, different shapes, and/or combinations of different shapes, can be used for the petals 1022 and 1032.

The frame 1000 can share many of the same features and characteristics as described above in reference to frames 100, 400, and 700. However, one difference (in addition to the shape of the petals 1022 and 1032 as previously described) is that the apposition portion 1020 and the sealing portion 1030 are configured to be able to apply an increased level of appositional forces to the surfaces of the tissue surrounding the aperture 1230. That is because (as best seen in FIG. 10) the apposition petals 1022 and the sealing petals 1032 of the frame 1000 are configured to overlap each other in their natural, unstressed states. In other words, the apposition petals 1022 and the sealing petals 1032 are formed to have concave shapes in opposite directions of each other such that the free ends of the apposition petals 1022 are located in the area of the sealing portion 1030 and the free ends of the sealing petals 1032 are located in the area of the apposition portion 1020. This crisscrossing (or overlapping) of the apposition petals 1022 and the sealing petals 1032 may result in an exertion of an increased level of appositional forces applied to the surfaces of the tissue surrounding aperture 1230 by the apposition petals 1022 and the sealing petals 1032. Accordingly, in some embodiments the tissue-sealing device 1100 may tend to exhibit enhanced conformability, sealing, and migration resistance.

When covering material 1110 is attached to sealing portion 1030, the sealing portion 1030 (which was formed with a concaved shape as described above) may become partially or fully flattened. In other words, as exemplified in FIG. 9B, the sealing portion 1030 may become generally planar after the application of the covering material 1110 to the sealing petals 1032. However, in some embodiments, the sealing portion 1030 may remain concave (e.g., refer to FIG. 9D) after the application of the covering material 1110 to the sealing petals 1032.

It should be understood from the description herein that, while the apposition portion 1020 and the sealing portion 1030 of the frame 1000 are equivalently sized and shaped in the depicted embodiment, such similarities are not required. For instance, in one non-limiting example, a frame of a tissue-sealing device can include an apposition portion including the wire loops 122 of the frame 100 (referring to FIGS. 1A and 1B) and a sealing portion including of the sealing petals 1032 of the frame 1000.

The covering material 1110 can be a material as described above in reference to covering material 210. The covering material 1110 can be attached to the elongate member 1010 as described above in reference to the attachment of covering material 210 to elongate member 110.

While the exemplary tissue aperture 1230 is depicted as generally circular, it should be understood that the design of the tissue-sealing device 1100 (and other embodiments described herein) advantageously lends itself to sealing a wide variety of differently-sized and shaped apertures 1230. This is accomplished in part because the defect-occupying portion 1040 is configured to exert a low level of radial force to the tissue aperture 1230. Additionally, the appositional force for sealing and migration resistance is substantially provided by the apposition portion 1020 and the sealing portion 1030, rather than the defect-occupying portion 1040. In fact, in some embodiments the appositional forces provided by the apposition portion 1020 and the sealing portion 1030 are substantially independent of the in situ device shape or diameter, thus providing reliable sealing across a wide variety of anatomies, and for dynamic anatomies (e.g., such as the GI tract).

The tissue-sealing device 1100 may be configured to be implanted in a patient such that the covering material 1110 fully overlays and seals the tissue aperture 1230. In the embodiments depicted in FIGS. 8A and 8C, the covering material 1110 is disposed on the sealing portion 1030, but not on the apposition portion 1020, nor the defect-occupying portion 1040. However, in some embodiments the covering material 1110 may be disposed on all or portions of the apposition portion 1020 and/or the defect-occupying portion 1040 in addition to the sealing portion 1030.

Figure 9A:
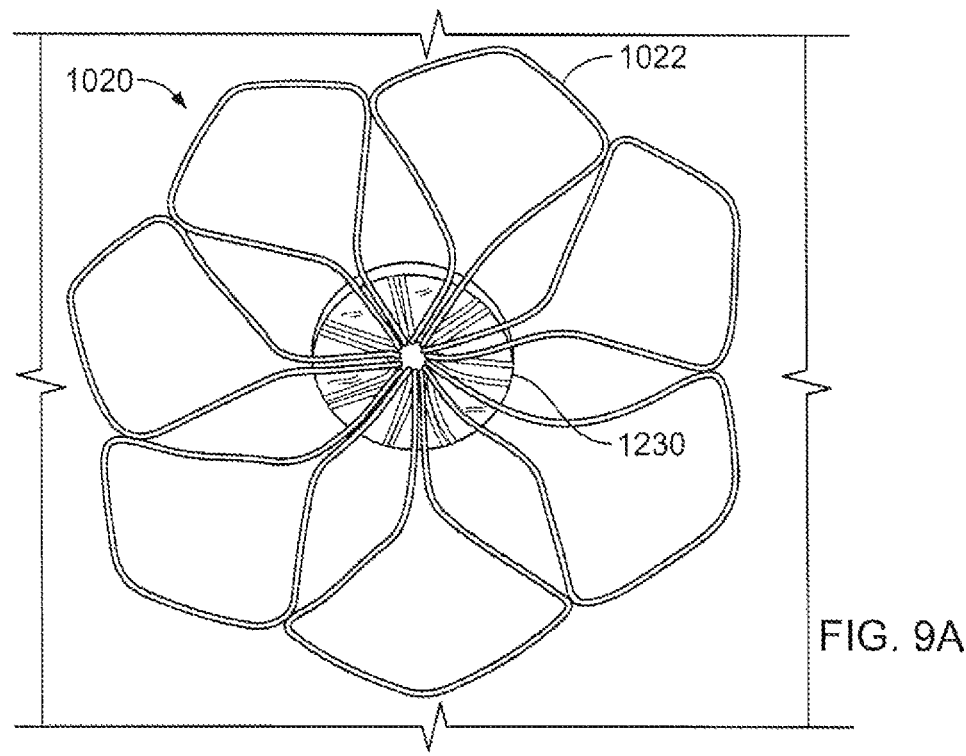
FIG. 9A is a plan view of the sealing device of FIG. 8A engaged in an exemplary tissue defect.
Figure 9B:
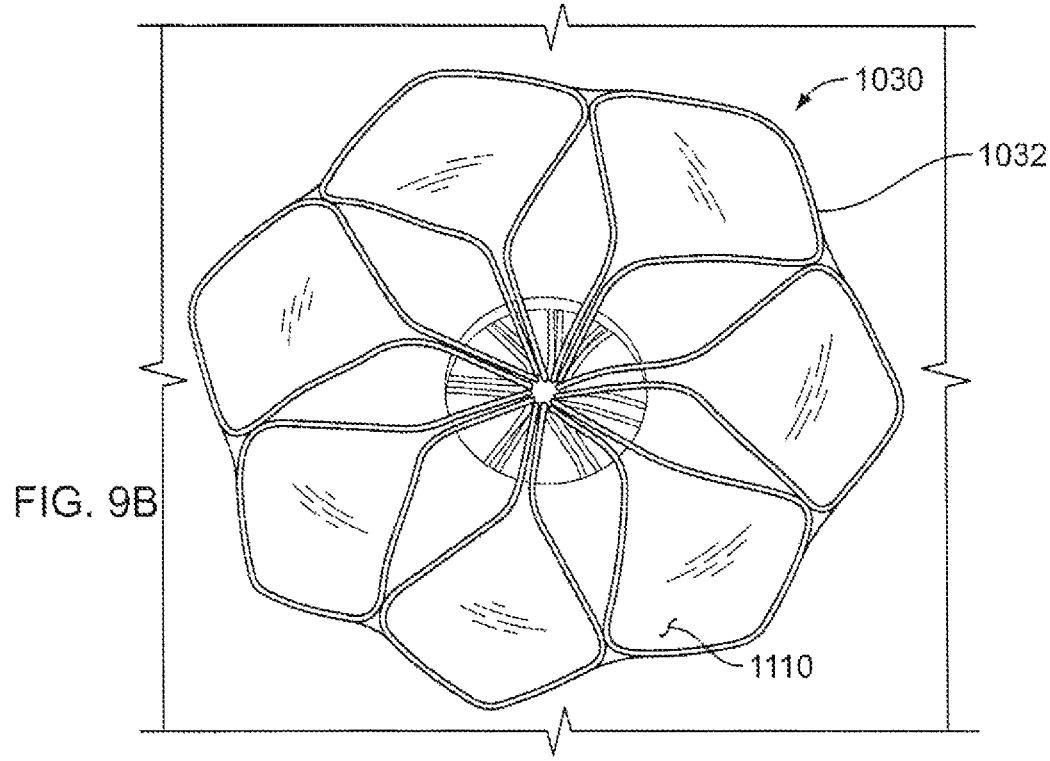
FIG. 9B is another plan view of the sealing device of FIG. 8A engaged in the exemplary tissue defect.
Figure 9C:
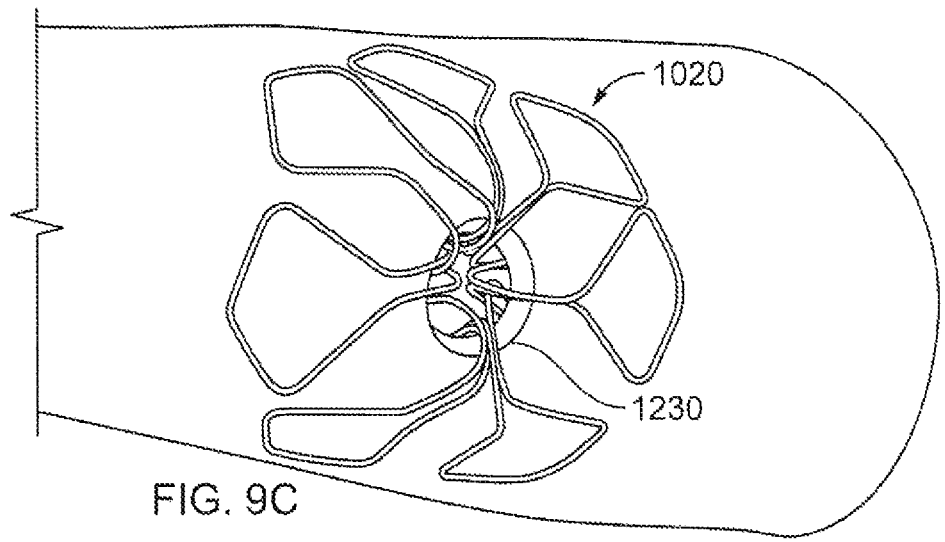
FIG. 9C is a perspective view of the sealing device of FIG. 8A engaged in another exemplary tissue defect.
Figure 9D:
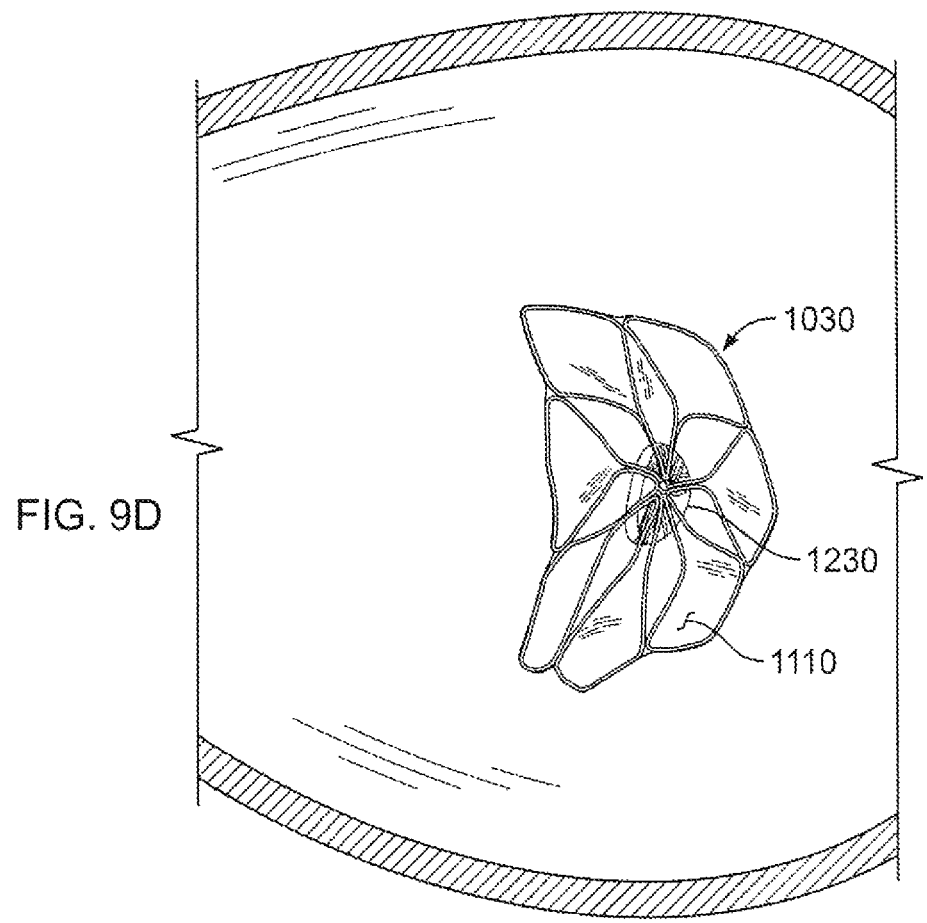
FIG. 9D is another perspective view of the sealing device of FIG. 8A engaged in another exemplary tissue defect.

FIGS. 9C and 9D illustrate the tissue-sealing device 1100 treating a defect in a body lumen wall. The wall of the body lumen naturally has curvature (i.e., it is a non-planar surface). As shown in FIGS. 9C and 9D, the apposition portion 1020 is in contact with the convexly-curved tissue wall (refer to FIG. 9C) and that the sealing portion 1030 is in contact with the concavely-curved tissue wall (refer to FIG. 9D). Accordingly, the tissue-sealing device 1100 is well-suited for sealing defects in body lumen walls, and other tissue surfaces, that are curved or otherwise non-planar.

Referring now to FIG. 9D, it can be seen that covering material 1110 overlays the aperture 1230 and contacts one or more portions of lumen wall tissue surrounding the aperture 1230. In this configuration, the covering material 1110 can provide a scaffold to support tissue that is generated by the body's healing process to repair the aperture 1230. In other words, the covering material 1110 can physically support tissue regrowth that makes the aperture 1230 smaller. In some cases, the aperture 1230 may have been created by a full thickness resection of an intestine. In other cases, other types of body tissues, or other types of defect causes can be treated in the aforementioned fashion.

The elongate member 1010 can be wound into the aforementioned shape to create frame 1000 using an appropriate winding mandrel 1300. After winding the elongate member 1010 on the mandrel, the assembly can be heated to induce a memory shape in the elongate member 1010 corresponding to the shape of the frame 1000 as-wound on the mandrel. Also, the two free ends of the elongate member 1010 can be conjoined as described above.

With reference to FIGS. 10A, 10B, 11A, and 11B, another exemplary tissue-sealing device 1400 that includes a frame 1410 and a covering material 1412 is illustrated. The covering material 1412 is disposed at least on a sealing portion 1430 of the frame 1410. The tissue-sealing device 1400 is shown sealing an exemplary tissue aperture 1530.

The frame 1410 includes an apposition portion 1420, a sealing portion 1430, and a defect-occupying portion 1440. In the depicted embodiment, the apposition portion 1420 and the sealing portion 1430 are configured dissimilarly. That is, the apposition portion 1420 includes one or more narrow wire loops 1422 and the sealing portion 1430 includes one or more wider petals 1432. The defect-occupying portion 1440 is disposed between the apposition portion 1420 and the sealing portion 1430. In addition, the defect-occupying portion 1440 may be configured to traverse the defect or aperture 1530 in one or more layers of tissue. Also, the apposition portion 1420 and the sealing portion 1430 may be configured to be on opposite sides of the layer(s) of tissue.

In some embodiments, the frame 1410 includes a single continuous wire that was bent to form the frame 1410. The frame 1410 defines apposition wire loops 1422 that form the apposition portion 1420, and sealing petals 1432 that form the sealing portion 1430. In the depicted embodiment, the apposition wire loops 1422 are shaped essentially as fingers, and the sealing petals 1432 are shaped essentially as diamonds on the ends of linear portions that extend from the central defect-occupying portion 1440. In some embodiments, different shapes and combinations of different shapes can be used for the wire loops 1422 and petals 1432. The use of dissimilar shapes for the apposition wire loops 1422 and the sealing petals 1432 can beneficially provide the opportunity to individually optimize the configurations of the apposition portion 1420 independently from those of the sealing portion 1430. For example, the apposition portion 1420 may be optimized for crushability or for conformability with irregular tissue topography, and the sealing portion 1430 may be optimized for sealing. In some embodiments, other performance characteristics or combinations of performance characteristics can be selected for optimization in relation to the apposition portion 1420 and the sealing portion 1430, individually.

The frame 1410 can share many of the same features and characteristics as described above in reference to frames 100, 400, 700, and 1000. For example, the wind pattern of the frame 1410 results in defining a peripheral frame for the sealing portion 1430. In addition, the apposition wire loops 1422 of the apposition portion 1420 and the sealing petals 1432 of the sealing portion 1430 are formed to have overlap (crisscross) for enhanced apposition force capability. The covering material 1412 may be a material as described above in reference to covering material 210. The covering material 1412 can be attached to the frame 1410 as described above in reference to the attachment of covering material 210 to elongate member 110.

While the exemplary tissue aperture 1530 is depicted as generally circular, it should be understood that the design of the tissue-sealing device 1400 (and other embodiments described herein) advantageously lends itself to sealing a wide variety of differently-sized and shaped apertures 1530. This is accomplished in part because the defect-occupying portion 1440 is configured to exert a low level of radial force to the tissue aperture 1530. Additionally, the appositional force for sealing and migration resistance is substantially provided by the apposition portion 1420 and the sealing portion 1430, rather than the defect-occupying portion 1440. In fact, in some embodiments the appositional forces provided by the apposition portion 1420 and the sealing portion 1430 are substantially independent of the in situ device shape or diameter, thus providing reliable sealing across a wide variety of anatomies, and for dynamic anatomies (e.g., such as the GI tract).

The tissue-sealing device 1400 may be configured to be implanted in a patient such that the covering material 1412 fully overlays and seals the tissue aperture 1530. In the embodiments shown in FIGS. 10A and 10B, the covering material 1412 is disposed on the sealing portion 1430, but not on the apposition portion 1420, nor the defect-occupying portion 1440. However, in some embodiments the covering material 1412 may be disposed on all or portions of the apposition portion 1420 and/or the defect-occupying portion 1440 in addition to the sealing portion 1430.

Figure 12:
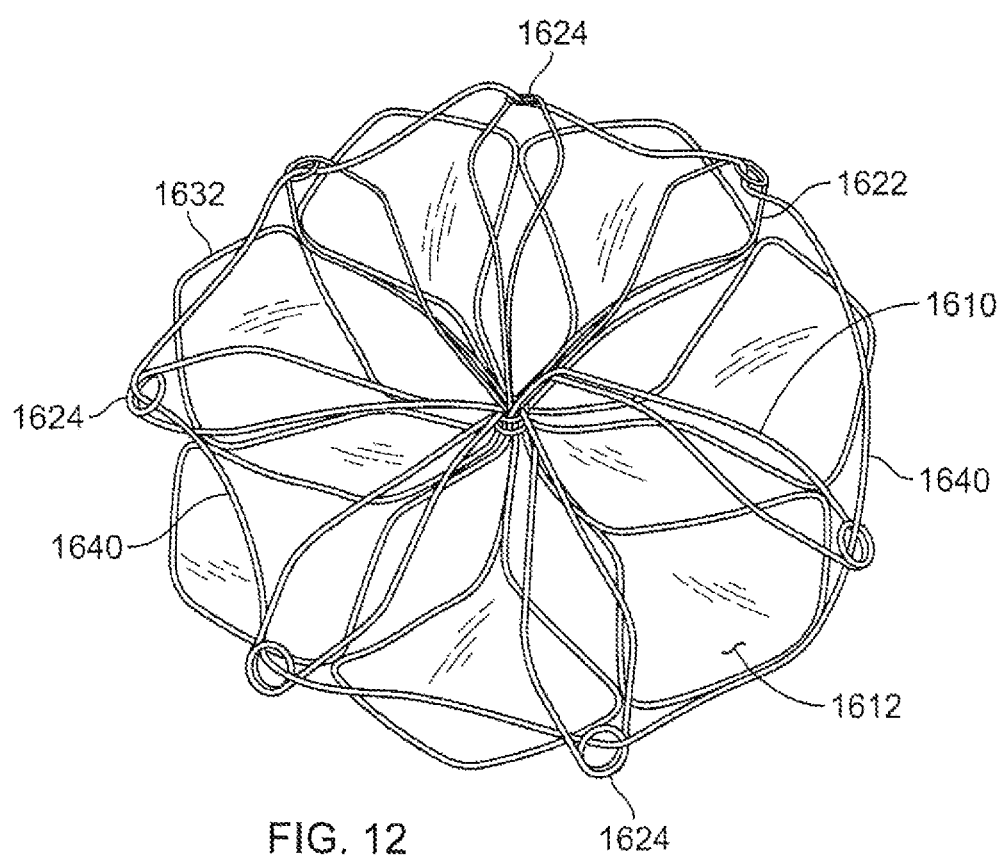
FIG. 12 is a perspective view of another exemplary sealing device in accordance with some embodiments.

With reference to FIG. 12, another exemplary tissue-sealing device 1600 is shown that includes a frame 1610 that defines one or more apposition wire loops 1622 and one or more sealing petals 1632. In some embodiments, a covering material 1612 is disposed on at least portions of the sealing petals 1632.

In some embodiments, the tissue-sealing device 1600 includes all of the characteristics and features of the tissue-sealing device 1400. In addition, the apposition wire loops 1622 of the tissue-sealing device 1600 include rings 1624 near the free ends of the apposition wire loops 1622. In some embodiments, the rings 1624 are integrally formed as part of the winding process of the frame 1610. In some embodiments, the rings 1624 are formed as separate components that are subsequently attached to the frame 1610. It should be understood that the rings 1624 can be combined with all embodiments of tissue-sealing device embodiments and anastomosis device embodiments provided herein. In some embodiments, the rings 1624 may be positioned on other locations of the frame 1610, and more or fewer rings 1624 may be included. For example, in some embodiments, the rings 1624 may be positioned on the sealing petals 1632 instead of, or in addition to, having the rings 1624 positioned on the apposition wire loops 1622.

In some embodiments, a flexible member 1640 is threaded through each of the rings 1624, so that the flexible member 1640 forms a closed and/or tensionable loop. The flexible member 1640 may be a cord, wire, strap, suture, and the like. In some embodiments, the flexible member 1640 can be made of a polymer material including, but not limited to, nylon, polypropylene, polytetrafluoroethylene (PTFE), silk, and the like. In some embodiments, the flexible member 1640 may be made of a metallic material including, but not limited to, nitinol, aluminum, stainless steel, and the like. In additional embodiments, the flexible member 1640 can be made of a combination of materials. The flexible member 1640 may be made of monofilament, twisted strands, braided strands, and the like. In some embodiments, the flexible member 1640 may be attached to one or more rings 1624, and slidably engaged with the other rings 1624. In some embodiments, the flexible member 1640 is slidably engaged with all of the rings 1624.

Pulling on (tensioning) the flexible member 1640 can cause a purse string effect. That is, pulling on the flexible member 1640 can draw the apposition wire loops 1622 towards each other. Such an action can be performed beneficially as a part of the process of crushing the tissue-sealing device 1600 to a low-profile configuration for the purpose of installing the device 1600 into a lumen of a sheath. That action can be performed when initially installing the device 1600 into a delivery sheath, or when recovering the device 1600 in situ so that the device 1600 can be retrieved and removed from a body using a transcatheter removal technique. For example, applying tension to the flexible member 1640 using a grasping tool can cause the tissue-sealing device 1600 to collapse to a lower-profile configuration for insertion in a retrieval sheath.

For example, when retrieval of the tissue-sealing device 1600 from the body is desired, a retrieval sheath containing a grasping tool can be routed to the location of the tissue-sealing device 1600 in the patient's body. The grasping tool can be used to temporarily couple with the flexible member 1640. As the grasping tool is thereafter retracted away from the tissue-sealing device 1600, tension is applied to the flexible member 1640. The tensioning and displacement of the flexible member 1640 caused by the grasping tool will cause the apposition wire loops 1622 to collapse to a lower-profile configuration. As the grasping tool is retracted further, including to within the retrieval sheath, the apposition wire loops 1622 will be drawn into the distal end of the retrieval sheath. A funnel can be included on the distal end portion of the retrieval sheath. The funnel will provide a wider initial opening at the distal tip of the retrieval sheath to facilitate the capture of all portions of the apposition wire loops 1622. As the grasping tool is further retracted, the entire tissue-sealing device 1600 can be pulled into the lumen of the retrieval sheath. Then the retrieval sheath, containing the tissue-sealing device 1600, can be removed from the patient. Retrieval features of various types and configurations, such as the flexible member 1640, may be included with any of the tissue-sealing device embodiments provided herein, if so desired.

Figure 13A:
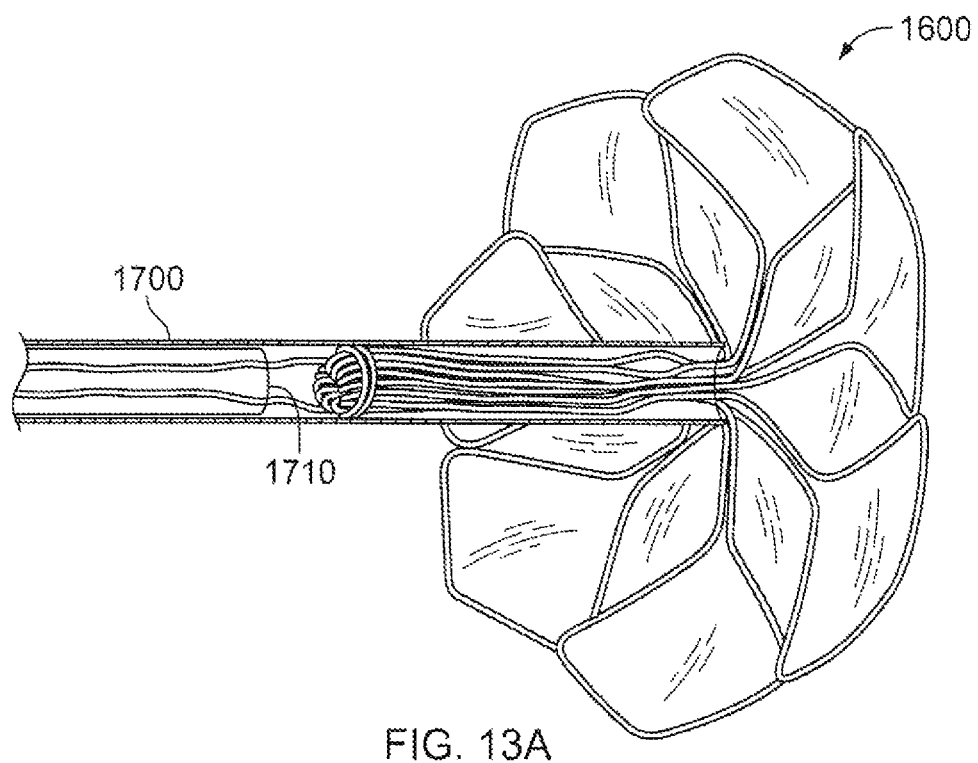
FIG. 13A is a perspective view showing the sealing device of FIG. 12 partially contained within an exemplary delivery sheath.
Figure 13B:
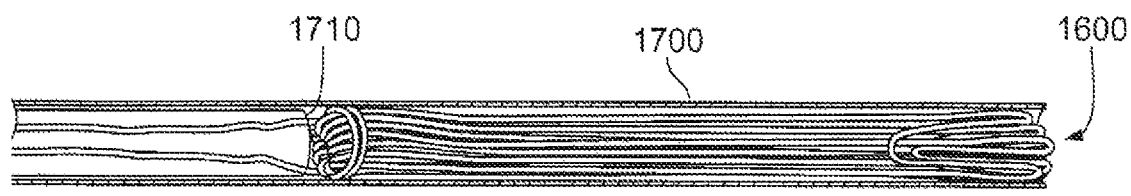
FIG. 13B is a side view showing the sealing device of FIG. 12 fully contained within the delivery sheath of FIG. 13A.

With reference to FIGS. 13A and 13B, the tissue-sealing device 1600 (as well as some embodiments of the other tissue-sealing device embodiments and anastomosis device embodiments provided herein) can be configured in a low-profile configuration for containment within a lumen of a sheath 1700. The sheath 1700 may be used for the initial installation of the tissue-sealing device 1600 in a body, or the sheath 1700 may be used for in situ retrieval of the tissue-sealing device 1600 from the body. The tissue-sealing device 1600 can be configured for self-expansion upon removal of the constraining forces resulting from containment within the lumen of the sheath 1700. That is, the tissue-sealing device 1600 can self-expand once liberated from the sheath 1700. To arrive at a low-profile (crushed) configuration such that the tissue-sealing device 1600 can fit within the sheath 1700, in some embodiments, portions of the tissue-sealing device 1600 may be folded one or more times.

In some embodiments, a sheath 1700 having about a 15 Fr. (5 mm) outer diameter can be used. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments.

In some embodiments, a pusher catheter 1710 is slidably disposed within the lumen of the sheath 1700. The pusher catheter 1710 can be, for example, manually used by a clinician operator to force the tissue-sealing device 1600 out of the lumen of the sheath 1700 when the distal tip of the sheath 1700 is positioned as desired at a target implantation site within a body, thereby deploying the tissue-sealing device 1600.

In the configuration shown in FIGS. 13A and 13B, the apposition portion is contained within the lumen of the sheath 1700 proximally of the sealing portion. In other words, deployment of the tissue-sealing device 1600 from the sheath 1700 will result in the emergence of the sealing portion of the tissue-sealing device 1600 prior to the emergence of the apposition portion. In some situations, it may be important to approach the target tissue defect from a direction with the orientation of the tissue-sealing device 1600 in relation to the sheath 1700 in mind. For example, when a defect in a body lumen wall is to be treated using the tissue-sealing device 1600, generally the sealing portion should be positioned within the body lumen (to seal the body lumen contents within the body lumen). Therefore, when the orientation of the tissue-sealing device 1600 in relation to the sheath 1700 is as shown in FIGS. 13A and 13B, the approach to the body lumen should be from the outside of the body lumen (e.g., laproscopically). That way, the sealing portion can be deployed through the defect so that the sealing portion is positioned inside of the body lumen. Then, by pulling back the sheath 1700, the apposition portion can be appropriately positioned on the outside surface of the body lumen.

In other configurations, the tissue-sealing device 1600 may be contained within the sheath 1700 such that the sealing portion is proximal of the apposition portion. In that configuration, the approach to the body lumen defect can be from within the lumen (e.g., using an endoscopic technique). That way, the apposition portion can be deployed through the defect so that the apposition portion is positioned outside of the body lumen. Then, by pulling back the sheath 1700, the sealing portion can be appropriately positioned on the inside surface of the body lumen.

In some medical procedures for deploying the tissue-sealing device 1600, the deployment process is performed using radiographic visualization or another imaging modality. As described above, some embodiments of the tissue-sealing device 1600 and other device embodiments provided herein are retrievable after deployment. Therefore, if the initial deployment position is deemed dissatisfactory, the tissue-sealing device 1600 can be fully or partially retrieved into the sheath 1700 and redeployed to a more desirable position.

Figure 14A:
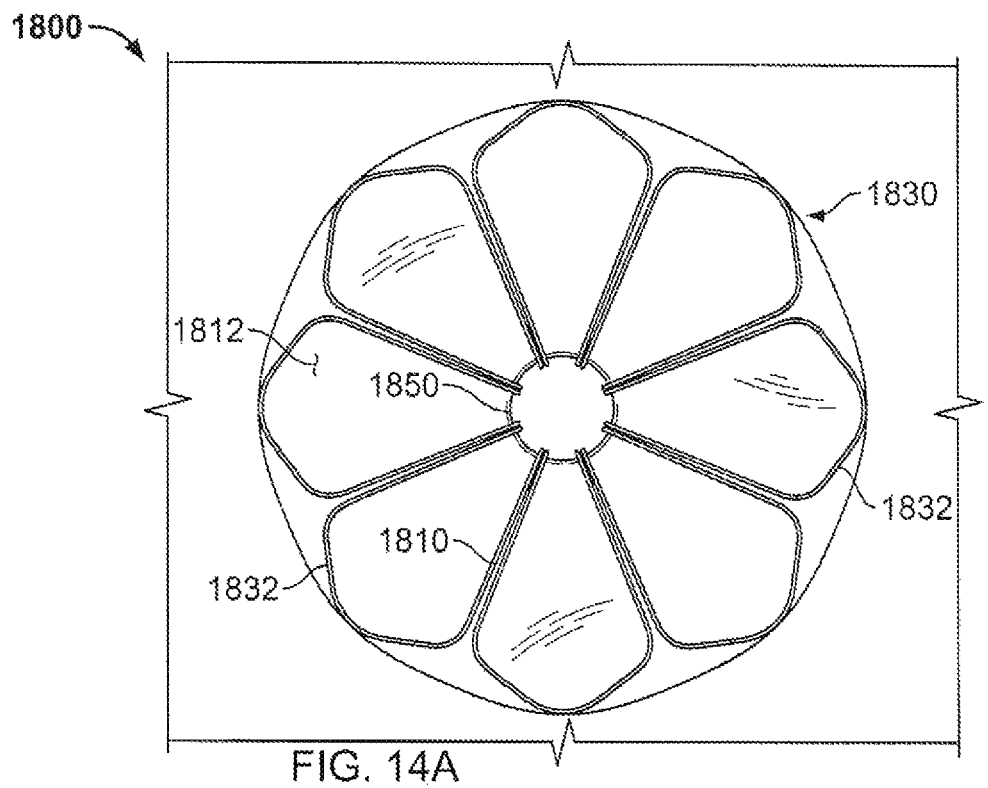
FIG. 14A is a plan view of a sealing portion of another sealing device engaged in an exemplary tissue defect.
Figure 14B:
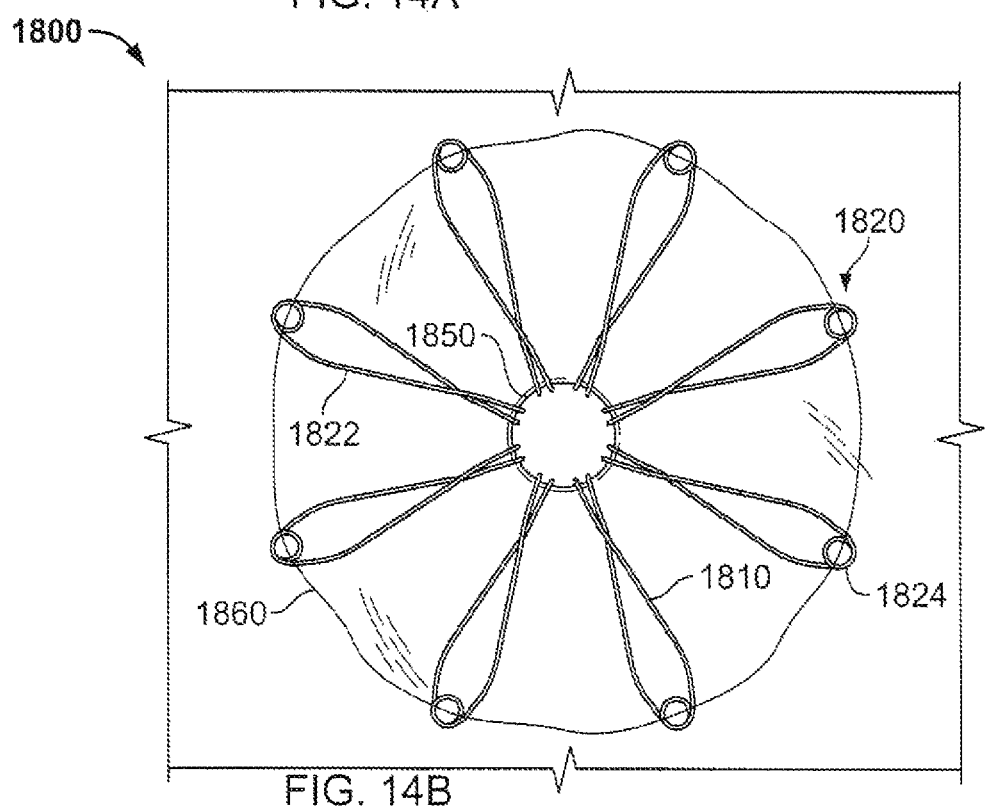
FIG. 14B is a plan view of an apposition portion of the sealing device of FIG. 14A.

With reference to FIGS. 14A and 14B, another exemplary tissue-sealing device 1800 includes a frame 1810 and a covering material 1812 is shown. The covering material 1812 is disposed on at least on a sealing portion 1830 of the frame 1810. The tissue-sealing device 1800 is shown sealing an exemplary tissue aperture 1850.

The frame 1810 includes an apposition portion 1820, a sealing portion 1830, and a defect-occupying portion positioned therebetween. In the embodiment depicted in FIGS. 14A and 14B, the apposition portion 1820 and the sealing portion 1830 are configured dissimilarly. That is, the apposition portion 1820 includes one or more narrow wire loops 1822, and the sealing portion 1830 includes one or more wider petals 1832. The apposition portion 1820 and the sealing portion 1830 may be configured to be on opposite sides of the layer(s) of tissue.

In some embodiments, the frame 1810 includes a single continuous wire that has been bent to form the frame 1810. The frame 1810 defines apposition wire loops 1822 that form the apposition portion 1820, and sealing petals 1832 that form the sealing portion 1830. In the depicted embodiment, the apposition wire loops 1822 are shaped essentially as fingers, and the sealing petals 1832 are shaped essentially as sectors of a circle. In some embodiments, each petal 1832 of the one or more petals 1832 is configured to generally abut at least portions of adjacent petals 1832, while not overlapping adjacent petals 1832. In some embodiments, one or more of the petals 1832 may be configured to be separated from adjacent petals 1832. In some embodiments, one or more of the petals 1832 may be configured to at least partially overlap adjacent petals 1832.

In some embodiments, different shapes and combinations of different shapes can be used for the wire loops 1822 and petals 1832. The use of dissimilar shapes for the apposition wire loops 1822 and the sealing petals 1832 can beneficially provide the opportunity to individually optimize the configurations of the apposition portion 1820 independently from those of the sealing portion 1830. For example, in some embodiments the apposition portion 1820 may be optimized for crushability or for conformability with irregular tissue topography, and the sealing portion 1830 may be optimized for sealing. In some embodiments, other performance characteristics or combinations of performance characteristics can be selected for optimization in relation to the apposition portion 1820 and the sealing portion 1830, individually.

The frame 1810 can share many of the same features and characteristics as described above in reference to frames 100, 400, 700, 1000, 1400, and 1600. For example, the wind pattern of the frame 1810 results in defining a peripheral frame for the sealing portion 1830. The covering material 1812 can be a material as described above in reference to covering material 210. The covering material 1812 can be attached to the frame 1810 as described above in reference to the attachment of covering material 210 to elongate member 110.

While the tissue aperture 1850 is depicted as generally circular, it should be understood that the design of the tissue-sealing device 1800 (and other embodiments described herein) advantageously lends itself to sealing a wide variety of differently-sized and shaped apertures 1850. This is accomplished in part because the appositional force for sealing and migration resistance is substantially provided by the apposition portion 1820 and the sealing portion 1830, rather than the defect-occupying portion. In fact, in some embodiments the appositional forces provided by the apposition portion 1820 and the sealing portion 1830 are substantially independent of the in situ device shape or diameter, thus providing reliable sealing across a wide variety of anatomies, and for dynamic anatomies (e.g., such as the GI tract).

The tissue-sealing device 1800 may be configured to be implanted in a patient such that the covering material 1812 fully overlays and seals the tissue aperture 1850. In the depicted embodiment, the covering material 1812 is disposed on the sealing portion 1830, but not on the apposition portion 1820, nor the defect-occupying portion. However, in some embodiments the covering material 1812 may be disposed on all or portions of the apposition portion 1820 and/or the defect-occupying portion in addition to the sealing portion 1830.

The apposition wire loops 1822 of the tissue-sealing device 1800 include rings 1824 near the free ends of the apposition wire loops 1822. In some embodiments, the rings 1824 are integrally formed as part of the winding process of the frame 1810. In some embodiments, the rings 1824 are formed as separate components that are subsequently attached to the frame 1810. It is to be appreciated that the rings 1824 can be combined with all embodiments of tissue-sealing devices provided herein. In some embodiments, the rings 1824 may be positioned on other locations of the frame 1810, and more or fewer rings 1824 may be included. For example, in some embodiments the rings 1824 may be positioned on the sealing petals 1832 instead of, or in addition to, having the rings 1824 positioned on the apposition wire loops 1822.

In some embodiments, a flexible member 1860 is threaded through each of the rings 1824 so that the flexible member 1860 forms a closed and/or tensionable loop. The flexible member 1860 may be a cord, wire, strap, suture, and the like, and can be constructed of the materials as described above in reference to the flexible member 1640. In some embodiments, the flexible member 1860 may be attached to one or more rings 1824, and slidably engaged with the other rings 1824. In some embodiments, the flexible member 1860 is slidably engaged with all of the rings 1824.

Pulling on (tensioning) the flexible member 1860 can cause a purse string effect. That is, pulling on the flexible member 1860 can draw the apposition wire loops 1824 towards each other. Such an action can be performed to crush the tissue-sealing device 1800 to a low-profile configuration for installing the device 1800 into a lumen of a sheath. The crushing action can be useful when initially installing the device 1800 into a delivery sheath, or when recovering the device 1800 in situ so that the device 1800 can be retrieved and removed from a body using a transcatheter removal technique.

Figure 15A:
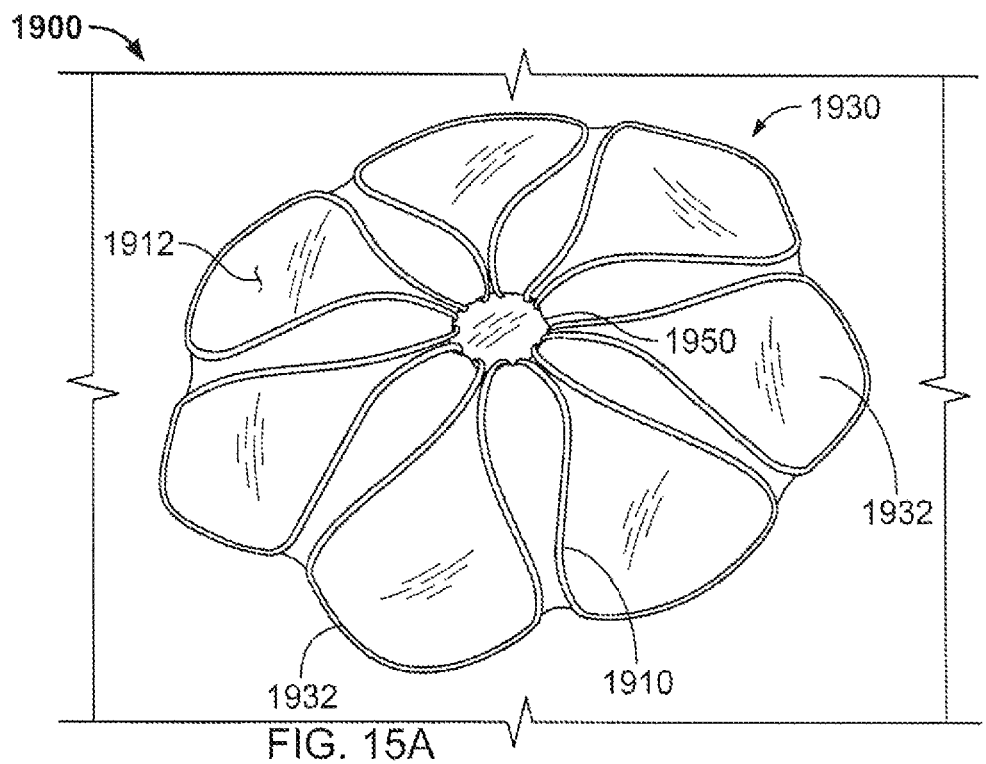
FIG. 15A is a perspective view of a sealing portion of another sealing device engaged in an exemplary tissue defect.
Figure 15B:
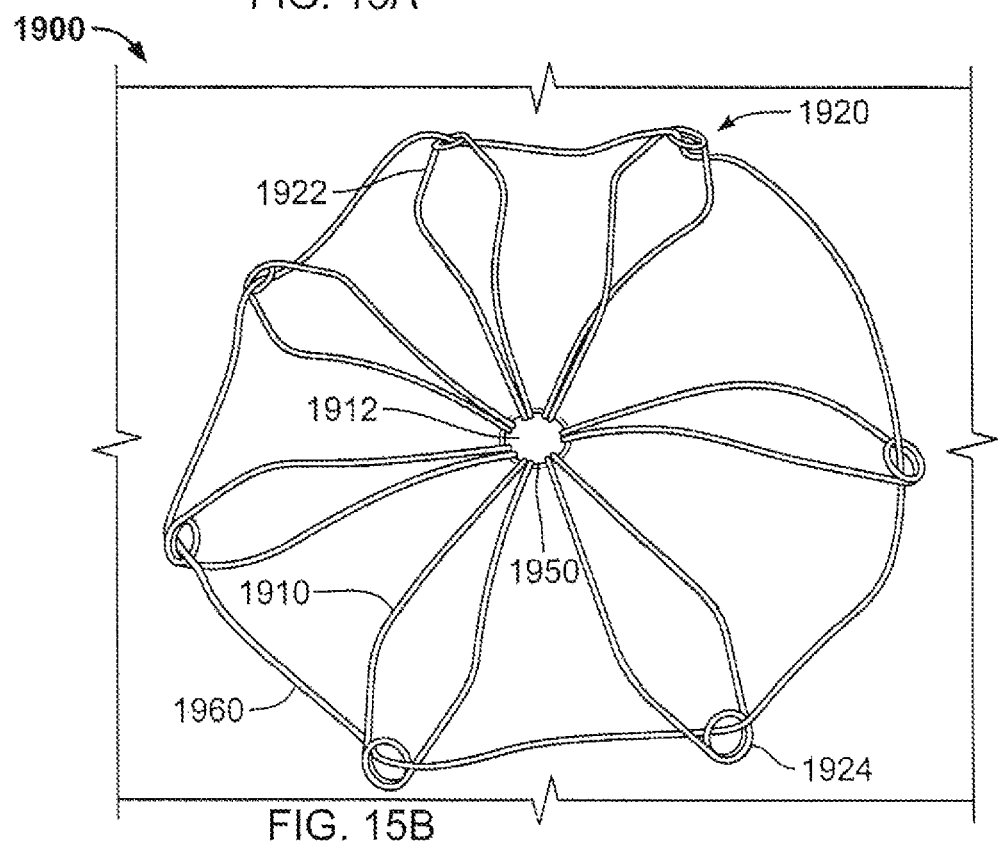
FIG. 15B is a perspective view of an apposition portion of the sealing device of FIG. 15A.

With reference to FIGS. 15A and 15B, another exemplary tissue-sealing device 1900 includes a frame 1910 and a covering material 1912 is illustrated. The covering material 1912 is disposed at least on a sealing portion 1930 of the frame 1910. The tissue-sealing device 1900 is shown sealing an exemplary tissue aperture 1950.

The frame 1910 includes an apposition portion 1920, a sealing portion 1930, and a defect-occupying portion positioned therebetween. In the depicted embodiment, the apposition portion 1920 and the sealing portion 1930 are configured dissimilarly. That is, the apposition portion 1920 includes one or more narrow wire loops 1922, and the sealing portion 1930 includes one or more wider petals 1932. The apposition portion 1920 and the sealing portion 1930 may be configured to be on opposite sides of the layer(s) of tissue.

In some embodiments, the frame 1910 includes a single continuous wire that has been bent to form the frame 1910. The frame 1910 defines apposition wire loops 1922 that form the apposition portion 1920, and sealing petals 1932 that form the sealing portion 1930. In the depicted embodiment, the apposition wire loops 1922 are shaped essentially as elongate wire loops, and the sealing petals 1932 are shaped essentially as teardrops. In some embodiments, each petal 1932 of the one or more petals 1932 is configured to generally abut at least portions of adjacent petals 1932, while not overlapping adjacent petals 1932. In additional embodiments, one or more of the petals 1932 are configured to be separated from adjacent petals 1932. In some embodiments, one or more of the petals 1932 are configured to at least partially overlap adjacent petals 1932.

In some embodiments, different shapes and combinations of different shapes can be used for the wire loops 1922 and petals 1932. The use of dissimilar shapes for the apposition wire loops 1922 and the sealing petals 1932 can beneficially provide the opportunity to individually optimize the configurations of the apposition portion 1920 independently from those of the sealing portion 1930.

The frame 1910 can share many of the same features and characteristics as described above in reference to frames 100, 400, 700, 1000, 1400, 1600, and 1800. For example, the wind pattern of the frame 1910 results in defining a peripheral frame for the sealing portion 1930. The covering material 1912 can be a material as described above in reference to covering material 210. The covering material 1912 can be attached to the frame 1910 as described above in reference to the attachment of covering material 210 to elongate member 110.

While the exemplary tissue aperture 1950 is depicted as generally circular, it should be understood that the design of the tissue-sealing device 1900 (and other embodiments described herein) advantageously lends itself to sealing a wide variety of differently-sized and shaped apertures 1950.

The tissue-sealing device 1900 may be configured to be implanted in a patient such that the covering material 1912 fully overlays and seals the tissue aperture 1950. In the embodiment shown in FIGS. 15A and 15B, the covering material 1912 is disposed on the sealing portion 1930, but not on the apposition portion 1920, nor the defect-occupying portion. However, in some embodiments the covering material 1912 may be disposed on all or portions of the apposition portion 1920 and/or the defect-occupying portion in addition to the sealing portion 1930.

The apposition wire loops 1922 of the tissue-sealing device 1900 include rings 1924 near the free ends of the apposition wire loops 1922. In some embodiments, the rings 1924 are integrally formed as part of the winding process of the frame 1910. In some embodiments, the rings 1924 are formed as separate components that are subsequently attached to the frame 1910. It should be understood that the rings 1924 can be combined with all embodiments of tissue-sealing devices provided herein. In some embodiments, the rings 1924 are positioned on other locations of the frame 1910, and more or fewer rings 1924 may be included. For example, in some embodiments the rings 1924 can be positioned on the sealing petals 1932 instead of, or in addition to, having the rings 1924 positioned on the apposition wire loops 1922.

In some embodiments, a flexible member 1960 is threaded through each of the rings 1924, so that the flexible member 1960 forms a closed and/or tensionable loop. The flexible member 1960 may be a cord, wire, strap, suture, and the like, and can be constructed of the materials as described above in reference to the flexible member 1640. In some embodiments, the flexible member 1960 may be attached to one or more rings 1924, and slidably engaged with the other rings 1924. In some embodiments, the flexible member 1960 is slidably engaged with all of the rings 1924.

Pulling on (tensioning) the flexible member 1960 can cause a purse string effect. That is, pulling on the flexible member 1960 can draw the apposition wire loops 1924 towards each other. Such an action can be performed to crush the tissue-sealing device 1900 to a low-profile configuration for installing the device 1900 into a lumen of a delivery sheath or when recovering the device 1900 in situ so that the device 1900 can be retrieved and removed from a body using a transcatheter removal technique.

A wire winding mandrel may be used in some embodiments to create the frame 1810 of tissue-sealing device 1800. That is, an elongate member can be wound to create frame 1810 using a suitable winding mandrel. After forming the frame 1810 on the mandrel, the assembly can be heated to induce a memory shape in the frame 1810 corresponding to the shape of the mandrel. Also, the two free ends of the elongate member can be conjoined as described above. In some embodiments, the two free ends of the elongate member are not conjoined. Similarly, a wire winding mandrel 2100 can also be used to create the frame 1910 of tissue-sealing device 1900. That is, an elongate member can be wound to create frame 1910 using a suitable winding mandrel.

The use of occlusive devices in the environment of the GI tract, for example, calls for occlusive devices that provide substantially continuous lumen wall contact with apposition force for effective sealing performance during peristaltic motion. Peristaltic motion can result in the application of large dynamic, asymmetric, and non-planar displacements to the occlusive devices in some circumstances, as well as normal and shear stresses from material transport. In some embodiments, the occlusive devices provided herein provide substantially continuous lumen wall contact with conformability and apposition force for effective occlusion and sealing performance during such conditions caused by peristaltic motion. For example, in some embodiments the occlusion device's provision of apposition force without the use of barbs or prongs allows the device to resist migration, seal, and be safely removed.

Referring now to FIGS. 16A-16C, an exemplary anastomosis device 2200 can be constructed using many of the same design features, characteristics, concepts, and methods of construction that also pertain to the tissue-sealing devices described above. However, the anastomosis device 2200 (and the other anastomosis device embodiments provided herein) is distinct from the tissue-sealing devices at least because of a central aperture 2250 that can facilitate material (e.g., biological materials) transfer therethrough. That is, while some portions of the anastomosis device 2200 are configured to substantially seal against surrounding tissue surfaces, the central aperture 2250 of the anastomosis device 2200 is configured to not seal, but rather to facilitate the transfer of materials (e.g., fluids, solids, mixtures) through the central aperture 2250 generally along a central axis 2216.

The anastomosis device 2200 includes a frame 2210 formed by an elongate member 2212. In some embodiments, the elongate member 2212 is a single element that is wound or otherwise formed to construct the frame 2210 of the anastomosis device 2200 (e.g., as described above in reference to the tissue-sealing devices). In some embodiments, the elongate member 2212 can include two or more elements that are cooperatively configured to define the frame 2210. The elongate member 2212 may be constructed using the techniques, and can be made of the types of materials, that are described above in reference to elongate member 110, for example.

In some embodiments, the elongate member 2212 forms a first flange 2220, a second flange 2230, and a connecting region 2240. The flanges 2220 and 2230 may also be referred to herein as "apposition portions." The connecting region 2240 may also be referred to herein as a "central portion." The connecting region 2240 is disposed between and interconnects the first flange 2220 and the second flange 2230. The connecting region 2240 is configured to traverse an opening or aperture 2244 in one or more layers of tissue. The first flange 2220 and the second flange 2230 are configured to be on opposite sides of the layer(s) of tissue and to apply apposition forces against the tissue surfaces.

The elongate member 2212 defines one or more apposition petals 2222 that form the first flange 2220. The elongate member 2212 also forms one more apposition petals 2232 that form the second flange 2230. In the depicted embodiment, the first flange 2220 includes five apposition petals 2222 and the second flange 2230 also includes five apposition petals 2232. The apposition petals 2222 and 2232 may also be referred to herein as "arms," "fins," "loops," "apposition members," or "fingers," for example.

While the depicted embodiment includes five apposition petals 2222 and 2232, it should be understood that some embodiments include other quantities of apposition petals 2222 and 2232. That is, the first flange 2220 and/or the second flange 2230 may include more than or less than five apposition petals 2222 and 2232. Further, in some embodiments the quantity of apposition petals 2222 may be different than the quantity of apposition petals 2232. Still further, the sizes and shapes (also referred to herein as the geometry) of the apposition petals 2222 may be different than the sizes and shapes of the apposition petals 2232. In some embodiments, the axes of one or more of the individual apposition petals 2222 may be offset (e.g., skew) from the axes of one or more of the individual apposition petals 2232. In some embodiments, the axes of one or more of the apposition petals 2222 may be parallel with the axes of one or more of the apposition petals 2232.

In the embodiment depicted in FIGS. 16A-16C, the apposition petals 2222 and 2232 are shaped essentially as segments of an annulus (e.g., approximately trapezoidal). In some embodiments, a variety of different petal geometries and/or combinations of different petal geometries can be used for the apposition petals 2222 and 2232. In the depicted embodiment, the apposition petals 2222 and 2232 abut each other. In some embodiments, some or all of the apposition petals 2222 and 2232 may partially overlap adjacent apposition petals 2222 and 2232, or some or all of the apposition petals 2222 and 2232 may be spaced apart from adjacent apposition petals 2222 and 2232. Again, such configurations may be used either uniformly or differently for the first flange 2220 in comparison to the second flange 2230.

In the depicted embodiment, the apposition petals 2222 are generally parallel to the apposition petals 2232 (as best seen in FIG. 22C), and the apposition petals 2222 and 2232 are distanced apart from each other. However, in some embodiments the apposition petals 2222 and 2232 may be formed to make at least partial contact with each other when no materials are therebetween. This and other such configurations of the apposition petals 2222 and 2232 may also be referred to herein as a pre-strained geometry of the apposition petals 2222 and 2232. Such a configuration may increase the amount of apposition force applied by the apposition petals 2222 and 2232 in comparison to the embodiment having parallelism between the apposition petals 2222 and 2232. Further, in some embodiments that have the apposition petals 2222 and/or 2232 that are spaced apart from adjacent apposition petals 2222 and/or 2232, and that have an axially offset between the individual petals of the first flange 2220 and the second flange 2230, some or all of the apposition petals 2222 and 2232 may be formed to crisscross each other when no materials are therebetween. Such a configuration may further increase the amount of apposition force applied by the apposition petals 2222 and 2232 in comparison to the embodiment having contact between the apposition petals 2222 and 2232. Combinations of all such configurations are also envisioned and are considered to be within the scope of this disclosure.

Still referring to FIGS. 16A, 16B, and 16C, the exemplary anastomosis device 2200 also includes a covering material 2214. The covering material 2214 can be disposed on and/or attached to at least portions of the elongate member 2212. In the depicted embodiment, the covering material 2214 is attached to the apposition petals 2222 and 2232 and to the connecting region 2240, while leaving the aperture 2250 uncovered. The covering material 2214 can be a material as described above in reference to covering material 210. The covering material 2214 can be attached to the elongate member 2212 as described above in reference to the attachment of covering material 210 to elongate member 110. In some embodiments, the covering material 2214 cooperates with the framework 2210 to provide a circumferential seal at the outer peripheral edge of the first flange 2220 and/or the second flange 2230.

Referring to FIG. 16B in particular, the exemplary anastomosis device 2200 is depicted as being deployed in one or more layers of tissue that have the opening 2244. While the exemplary tissue opening 2244 is depicted as generally circular, it should be understood that the design of the anastomosis device 2200 (and other anastomosis device embodiments described herein) advantageously lends itself to conforming to a wide variety of differently-sized and shaped tissue openings 2244. That is accomplished, at least in part, because the connecting region 2240 is configured to exert a low level of radial force to the tissue opening 2244. Additionally, the appositional force for sealing and migration resistance is substantially delivered by the first and second flanges 2220 and 2230, rather than the connecting region 2240. In fact, in some embodiments the appositional forces delivered by the first and second flanges 2220 and 2230 are substantially independent of the in situ device shape or diameter, thus providing reliable sealing, migration resistance, and anastomosis performance across a wide variety of anatomic topographies, and for dynamic anatomies (e.g., such as the GI tract).

The exemplary anastomosis device 2200 (and other anastomosis device embodiments described herein) can be deployed using the devices and techniques described above in reference to FIGS. 13A and 13B, for example.

In some embodiments, the exemplary anastomosis device 2200 (and other anastomosis device embodiments described herein) substantially do not interfere with the healing response of the body, such as when two tissues that are anastomosed using the devices provided herein grow together to form a tissue-anastomosis. In some embodiments, the anastomosis devices described herein are configured to be removable after deployment (such as after the anastomosed tissues have grown together). Therefore, in some such embodiments the anastomosis devices described herein are configured to prevent or inhibit tissue ingrowth, and are designed for atraumatic withdrawal. For example, in some embodiments the anastomosis devices described herein are configured to adequately seal and resist migration by exerting apposition forces without the use of barbs or prongs (thereby facilitating removal of the devices in a substantially atraumatic manner). In some such embodiments, the anastomosis devices described herein may include features to facilitate efficient repositioning and/or retrieval such as, but not limited to, rings on one or more of the apposition petals 2222 and 2232 and a flexible member that is threaded through such rings (e.g., refer to tissue-sealing devices 1800 and 1900 described above).

Figure 17B:
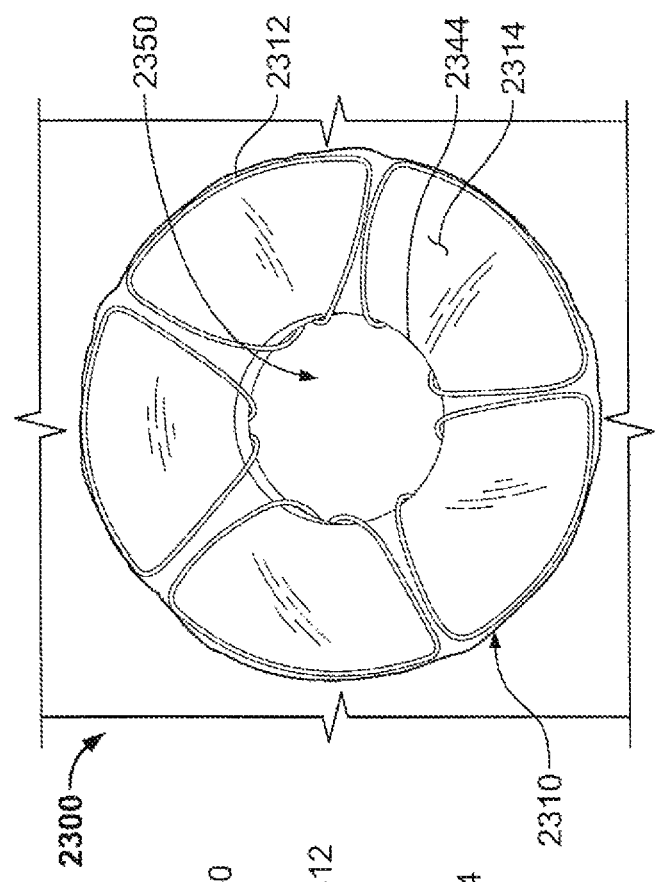
FIG. 17B is a plan view showing the exemplary anastomosis device of FIG. 17A engaged with tissues to create an anastomosis.
Figure 17A:
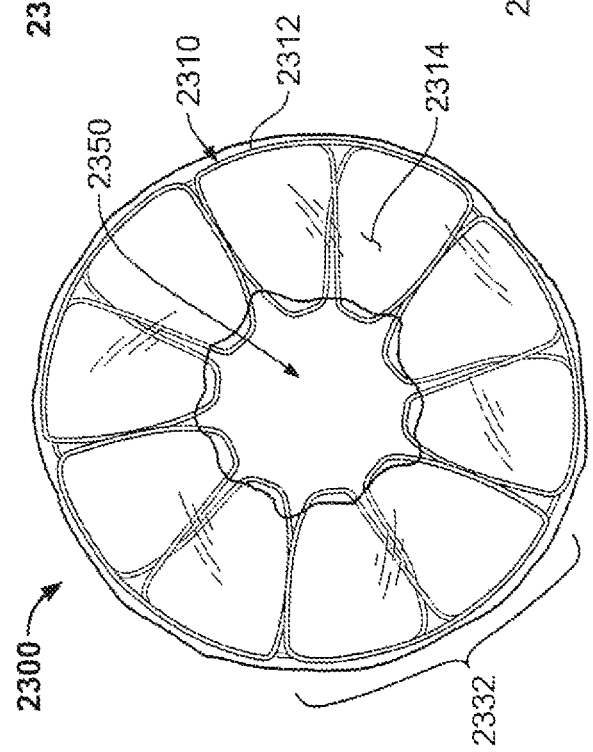
FIG. 17A is a plan view of another exemplary anastomosis device in accordance with some embodiments.

In reference to FIGS. 17A-17C, another exemplary anastomosis device 2300 is shown that may be constructed using many of the same design features, characteristics, concepts, and methods of construction that pertain to the anastomosis device 2200 described above, as well as to the tissue-sealing devices described above. As with the anastomosis device 2200, the anastomosis device 2300 (and the other anastomosis device embodiments provided herein) is distinct from the tissue-sealing devices at least because of a central aperture 2350 that can facilitate material transfer therethrough. That is, while some portions of the anastomosis device 2300 are configured to substantially seal against surrounding tissue surfaces, the central aperture 2350 of the anastomosis device 2300 is configured to not seal, but rather to facilitate the transfer of materials (e.g., fluids, solids, mixtures) through the central aperture 2350 along a central axis 2316.

The anastomosis device 2300 includes a frame 2310 formed by an elongate member 2312. In some embodiments, the elongate member 2312 is a single element that is wound or otherwise formed to construct the frame 2310 of the anastomosis device 2300 (e.g., like described above in reference to the tissue-sealing devices). In some embodiments, the elongate member 2312 can include two or more elements that are cooperatively configured to define the frame 2310. The elongate member 2312 may be constructed using the techniques, and may be made of the types of materials that are described above in reference to elongate member 110, for example.

In some embodiments, the elongate member 2312 forms a first flange 2320, a second flange 2330, and a connecting region 2340. The connecting region 2340 is disposed between and interconnects the first flange 2320 and the second flange 2330. The connecting region 2340 is configured to traverse an opening or aperture 2344 in one or more layers of tissue. The first flange 2320 and the second flange 2330 may be configured to be on opposite sides of the layer(s) of tissue and to apply apposition forces against the tissue surfaces.

The elongate member 2312 defines one or more apposition petals 2322 that form the first flange 2320. The elongate member 2312 also forms one more apposition petals 2332 that form the second flange 2330. In the embodiment depicted in FIGS. 17A-17C, the first flange 2320 includes five apposition petals 2322 and the second flange 2330 includes five apposition petals 2332. In other embodiments, fewer or more than five petals 2322 and/or 2332 may be included, and the flanges 2320 and 2330 may have unequal numbers of petals 2322 and 2332. The geometry of the apposition petals 2322 may also be different than the geometry of the apposition petals 2332. In some embodiments, the axes of one or more of the individual apposition petals 2322 may be offset (e.g., skew) from the axes of one or more of the individual apposition petals 2332. In some embodiments, the axes of one or more of the apposition petals 2322 may be parallel with the axes of one or more of the apposition petals 2332.

While the frame 2310 can share many of the same features and characteristics as described above in reference to frame 2210, one difference is that the apposition petals 2322 and 2332 may be configured with concave shapes (as best seen in FIG. 17C). Such concavity can allow the flanges 2320 and 2330 to apply an increased level of appositional forces to the surfaces of the tissue surrounding the aperture 2344, as compared to the appositional force caused by generally planar petals. In addition, the concave shape of the flanges 2320 and 2330 concentrates the apposition force at the outer perimeter the frame 2310, creating greater pressure on the tissue in comparison to planar flanges that distribute apposition force over a larger area. Additionally, the concave shape of the flanges 2320 and 2330 enables the accommodation of a broad range of tissue thickness. Further, in some embodiments the apposition petals 2322 and 2332 may be configured to partially contact each other or to crisscross each other (as described above), thereby providing increased apposition force capabilities. Accordingly, in some embodiments the anastomosis device 2300 may exhibit enhanced conformability, sealing, and migration resistance. Further, the concavity of the apposition petals 2322 and 2332 can allow the anastomosis device 2300 to be used effectively in conjunction with a broad range of tissue thicknesses. In some embodiments, one or the other of the flanges 2320 and 2330 may include concaved petals while the other of the flanges 2320 and 2330 may include petals of another contour (e.g., planar petals).

The exemplary anastomosis device 2300 also includes a covering material 2314. The covering material 2314 can be disposed on or around and/or attached to at least portions of the elongate member 2312. In the embodiment shown in FIGS. 17A-17C, the covering material 2314 is attached to the apposition petals 2322 and 2332 and to the connecting region 2340, leaving the aperture 2350 uncovered. The covering material 2314 can be a material as described above in reference to covering material 210. Additionally, the covering material 2314 can be attached to the elongate member 2312 as described above in reference to the attachment of covering material 210 to elongate member 110. In some embodiments, the covering material 2314 cooperates with the framework 2310 to provide a circumferential seal at the outer peripheral edge of the first flange 2320 and/or the second flange 2330.

Referring to FIG. 17B in particular, the exemplary anastomosis device 2300 is depicted as being deployed in one or more layers of tissue that have an opening 2344. While the exemplary tissue opening 2344 is depicted as generally circular, it should be understood that the design of the anastomosis device 2300 (and other anastomosis device embodiments described herein) advantageously lends itself to conforming to a wide variety of differently-sized and shaped tissue openings 2344. That is accomplished, at least in part, because the connecting region 2340 is configured to exert a low level of radial force to the tissue opening 2344. Additionally, the appositional force for sealing and migration resistance is substantially delivered by the first and second flanges 2320 and 2330, rather than the connecting region 2340. In fact, in some embodiments the appositional forces delivered by the first and second flanges 2320 and 2330 are substantially independent of the in situ device shape or diameter, thus providing reliable sealing, migration resistance, and anastomosis performance across a wide variety of anatomic topographies, and for dynamic anatomies (e.g., such as the GI tract).

In some embodiments, when the covering material 2314 is attached to first and second flanges 2320 and 2330, some or all of the apposition petals 2322 and 2332 (which were formed with a concaved shape as described above) may become partially or fully flattened. In other words, the first and second flanges 2320 and 2330 may become more planar in some embodiments after the application of the covering material 2314 to the apposition petals 2322 and 2332. However, in other embodiments, the first and second flanges 2320 and 2330 may remain concave after the application of the covering material 2314 to the apposition petals 2322 and 2332.

Figure 21:
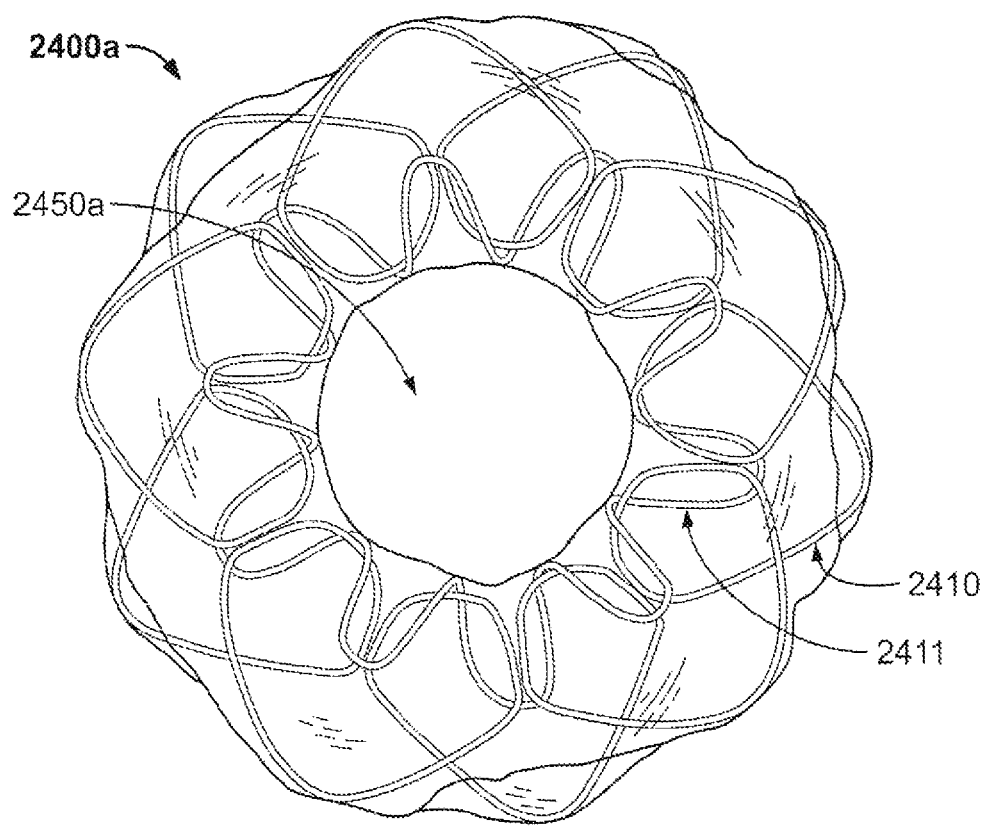
FIG. 21 is a plan view of another exemplary anastomosis device including a first arrangement of the apposition member frame of FIG. 18 and the support frame of FIG. 19.
Figure 22:
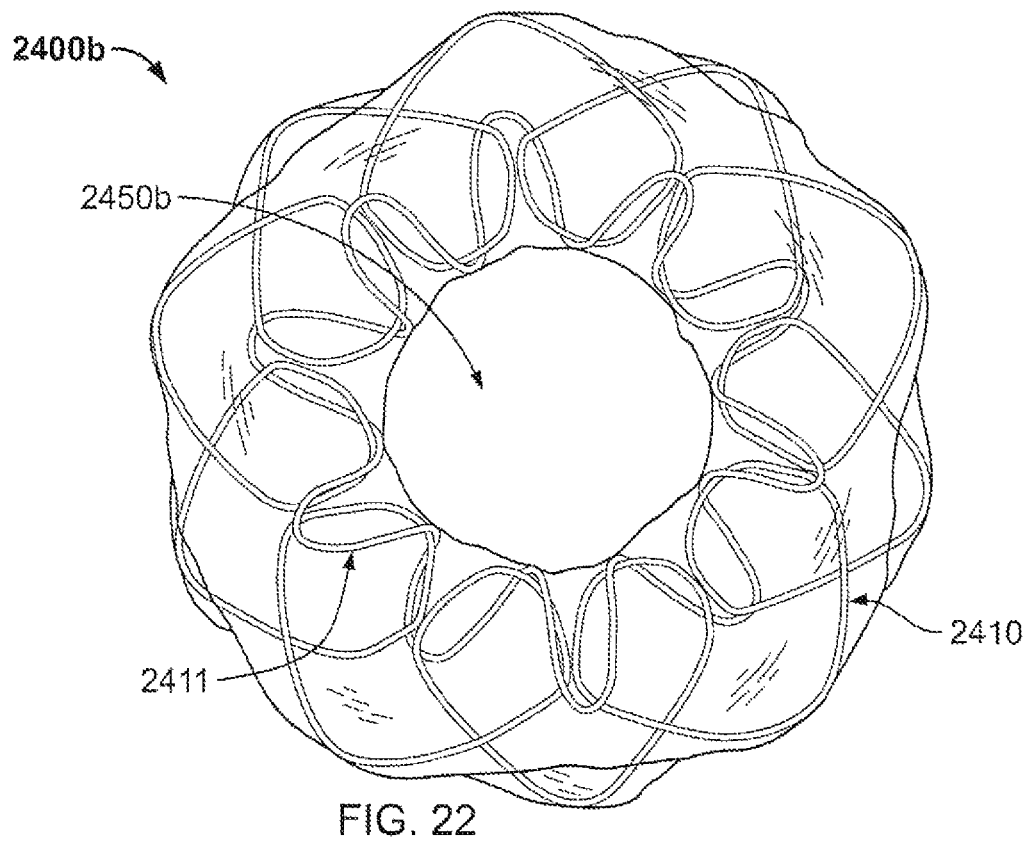
FIG. 22 is a plan view of another exemplary anastomosis device including a second arrangement of the apposition member frame of FIG. 18 and the support frame of FIG. 19.

Referring to FIGS. 21-22, additional exemplary anastomosis devices 2400a and 2400b are shown which may be constructed using many of the same design features, characteristics, concepts, and methods of construction that pertain to the anastomosis device 2200 and others described above, as well as to the tissue-sealing devices described above. As with the anastomosis device 2200, the anastomosis devices 2400a and 2400b (and the other anastomosis device embodiments provided herein) are distinct from the tissue-sealing devices at least because of the central apertures 2450a and 2450b that can facilitate material transfer therethrough. That is, while some portions of the anastomosis devices 2400a and 2400b are configured to substantially seal against surrounding tissue surfaces, the central apertures 2450a and 2450b of the anastomosis devices 2400a and 2400b are configured to not seal, but rather to facilitate the transfer of materials (e.g., fluids, solids, mixtures) through the central apertures 2450a and 2450b. The central apertures 2450a and 2450b define longitudinal axes of the anastomosis devices 2400a and 2400b respectively. One of skill in the art will appreciate that the anastomosis devices 2400a and 2400b can also be configured as tissue-sealing devices.

Figure 18:
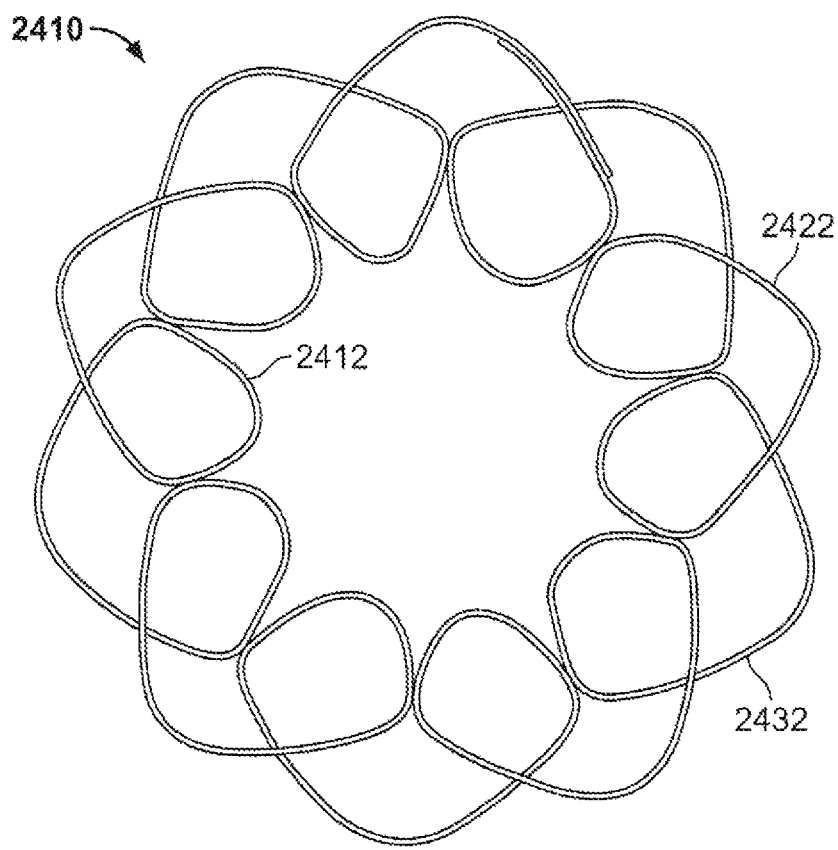
FIG. 18 is a plan view of an exemplary apposition member frame in accordance with some embodiments.
Figure 19:
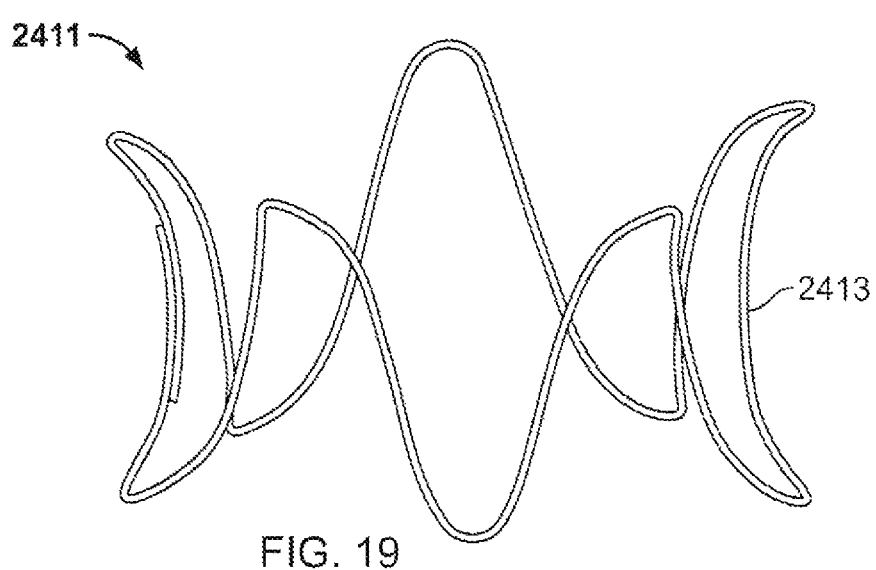
FIG. 19 is an elevation view of an exemplary support frame that may be used in conjunction with the apposition member frame of FIG. 18.
Figure 20:
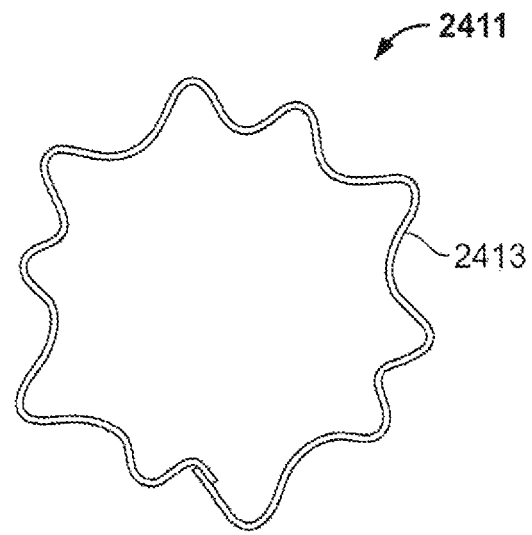
FIG. 20 is a plan view of the support frame of FIG. 19.

In some embodiments, the frames of the anastomosis devices 2400a and 2400b are constructed from two distinct frame portions. That is, the frames of the anastomosis devices 2400a and 2400b include an apposition member frame 2410 (refer to FIG. 18) that is used in conjunction with a support frame 2411 (refer to FIG. 19). As shown in FIGS. 21 and 22, in some embodiments the support frame 2411 may be concentrically nested within the apposition member frame 2410 to construct the two-part frames of the anastomosis devices 2400a and 2400b respectively. In some embodiments, the frames of the anastomosis devices 2400a and 2400b can be formed unitarily from a single wire, or formed by cutting a precursor material such as a tubular or sheet material.

In some two-part frame embodiments of anastomosis devices 2400a and/or 2400b, the support frame 2411 is affixed to the apposition member frame 2410. In some such embodiments, the support frame 2411 is affixed to the apposition member frame 2410 using ties, crimp collars, welding (e.g., laser welding), adhesives, and the like. In some such embodiments, the support frame 2411 is not directly affixed to the apposition member frame 2410, but the two are held together by virtue of a covering material that is disposed on at least portions of the support frame 2411 and the apposition member frame 2410.

Figure 27:
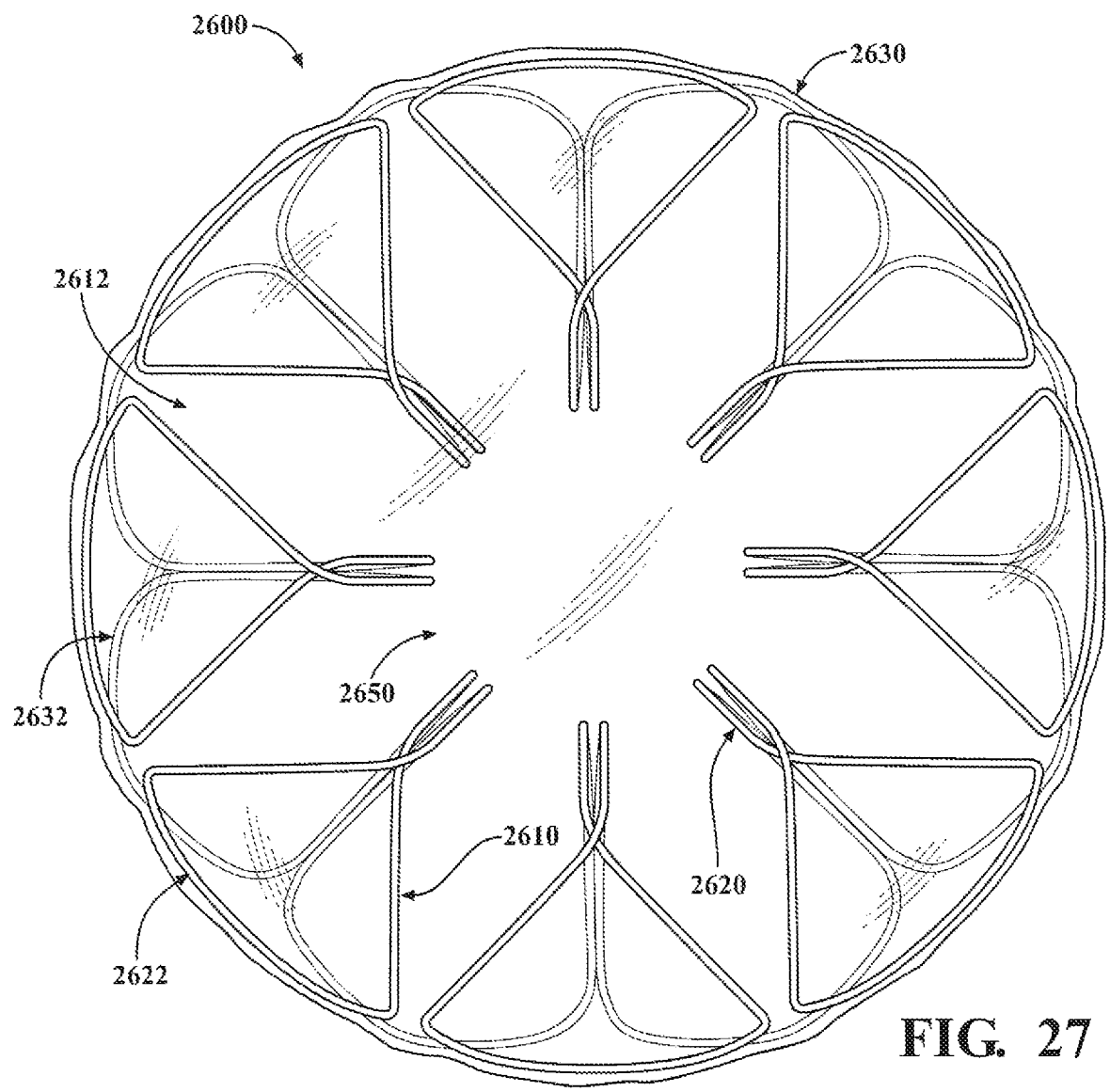
FIG. 27 is a plan view of an exemplary tissue-sealing device including a frame and covering material where the apposition petals and sealing petals are dissimilar.

The two anastomosis devices 2400a and 2400b are different from each other in regard to the position of the support frame 2411 in relation to the apposition member frame 2410. The anastomosis device 2400a is arranged such that aligned support is provided by the support frame 2411 in relation to the apposition member frame 2410. That is, contact by the support frame 2411 with the elongate element 2412 of the apposition petals 2422 and 2432 provides additional rigidity to the apposition petals 2422 and 2432 of the apposition member frame 2410. In contrast, the anastomosis device 2400b is arranged such that offset support is provided by the support frame 2411 in relation to the apposition member frame 2410. That is, the support frame 2411 does not make contact with the elongate element 2412 of the apposition petals 2422 and 2432, and therefore does not support the apposition petals 2422 and 2432 directly. However, in some embodiments the support frame 2411 itself provides additional apposition petals within the apposition petals 2422 and 2432 (as best seen in FIG. 27). It should be understood that, as with the other anastomosis device embodiments described herein, a connecting region (not shown) extends between the apposition petals 2422 and 2432.

In some embodiments, the two-part frame construct of the anastomosis devices 2400a and 2400b facilitates the provision of additional radial force from the anastomosis devices 2400a and 2400b in comparison to some single-part frame constructs. That is the case at least because both frame portions, the support frame 2411 and the apposition member frame 2410, can be configured to exert radial force. Because of the concentric relationship between the support frame 2411 and the apposition member frame 2410, the radial forces from them are generally additive.

In additional embodiments, one or more elongate element 2412 may be used to construct the apposition member frame 2410, and one or more elongate element 2413 may be used to construct the support frame 2411. In some embodiments, the elongate element(s) 2412 is the same type of elongate element as the elongate element(s) 2413. In other embodiments, the elongate element(s) 2412 is a different type of elongate element as the elongate element(s) 2413. In some such embodiments, the radial force and the apposition force provided by the anastomosis devices 2400a and 2400b can be individually and independently tailored as desired, because the elongate element(s) 2412 is a different type of elongate element as the elongate element(s) 2413. For example, in some embodiments, the elongate element(s) 2413 may have a greater stiffness than the elongate element(s) 2412. That may be the case, for example, because the selected elongate element(s) 2413 may have a larger diameter than the selected elongate element(s) 2412. Or, the selected elongate element(s) 2413 may be made of a stiffer material than the selected elongate element(s) 2412. By selecting such an arrangement, the radial force provided by the anastomosis devices 2400a and 2400b can be tailored to a higher amount of force while the apposition force provided by the anastomosis devices 2400a and 2400b can be at a relatively lower amount of force. Further, by selecting the relative orientation of the apposition member frame 2410 in relation to the support frame 2411 (i.e., whether to configure the two-part frame like anastomosis device 2400a or 2400b), the characteristics of the anastomosis devices 2400a and/or 2400b can be tailored as desired.

In some embodiments, the one or more elongate element 2412 used to construct the apposition member frame 2410 is a different material than the one or more elongate element 2413 used to construct the support frame 2411. For example, in some embodiments the one or more elongate element 2412 is nitinol, while the one or more elongate element 2413 is stainless steel. Moreover, in some such embodiments the apposition member frame 2410 may be self-expanding, while the support frame 2411 may be balloon-expandable.

Figure 23:
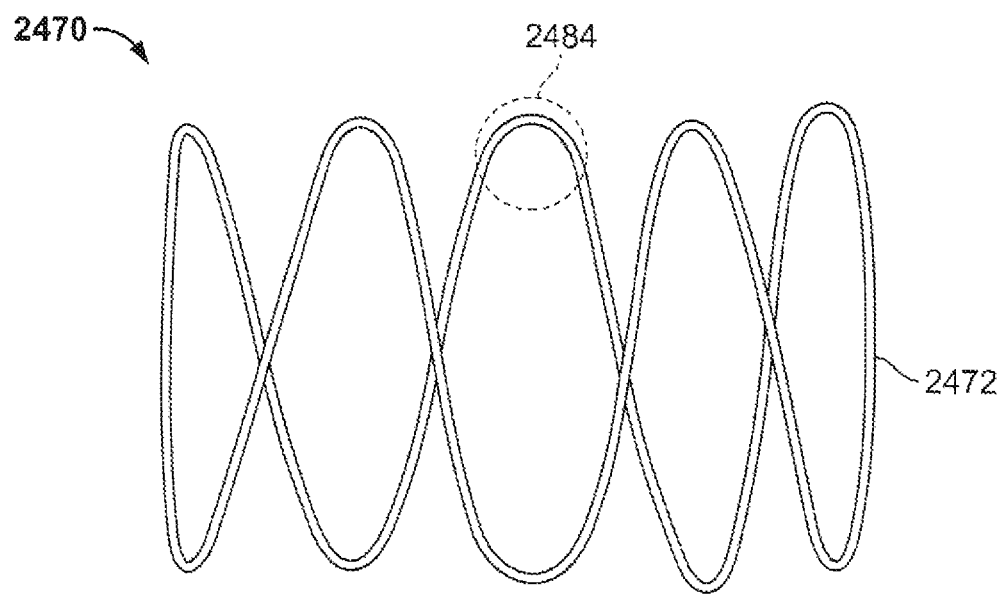
FIG. 23 is an elevation view of another exemplary support frame that can be used in conjunction with the apposition member frame of FIG. 18.
Figure 24:
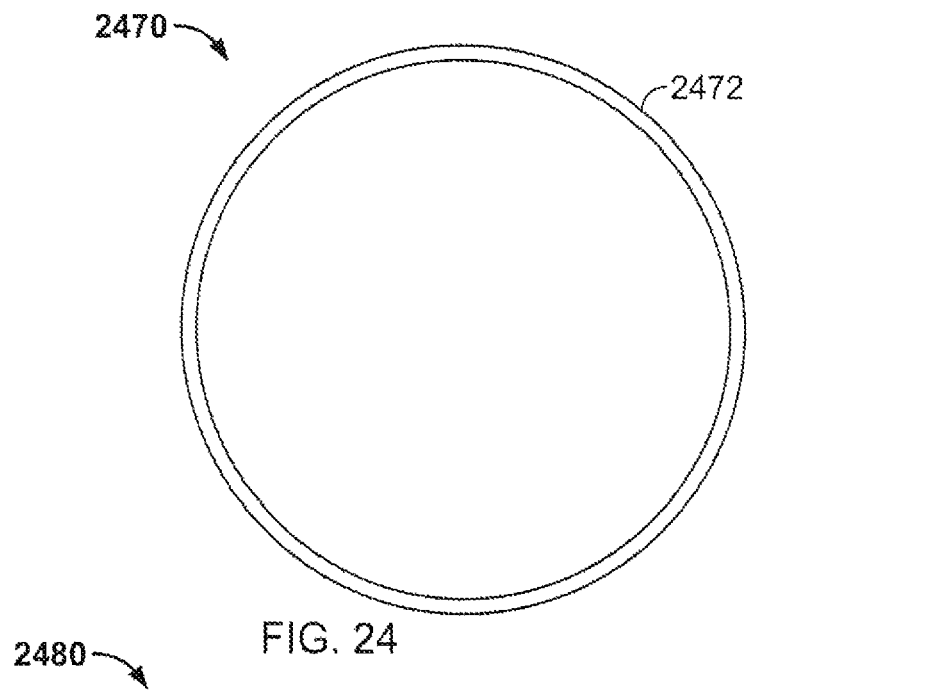
FIG. 24 is a plan view of the support frame of FIG. 23.

Referring to FIGS. 23 and 24, an alternative support frame 2470 is depicted. The support frame 2470 can be used in conjunction with an apposition member frame, such as, but not limited to, the apposition member frame 2410. Accordingly, the advantages of the concentrically nested two-part frame construct, as described above, can be achieved using the apposition member frame 2500 as well.

The support frame 2470 may be formed from one or more elongate members 2472. The one or more elongate members 2472 may be made from any of the materials and may be made using any of the techniques described above in reference to the other elongate members provided herein. In some embodiments, the support frame 2470 is formed as a wound-wire construct. In some embodiments, the support frame 2470 is formed by cutting a precursor material as described above.

Figure 25:
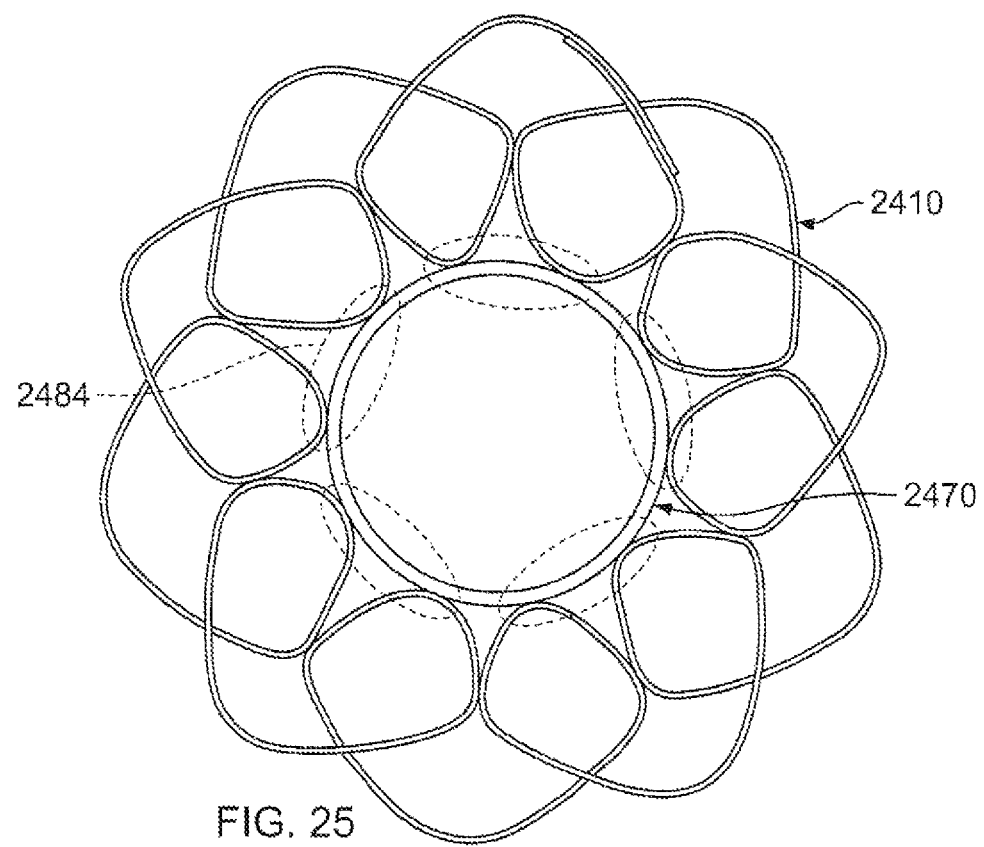
FIG. 25 is a plan view of another exemplary anastomosis device including a first arrangement of the apposition member frame of FIG. 18 and the support frame of FIG. 19.

The support frame 2470 includes a plurality of apices 2484. In some embodiments, the apices 2484 are positioned in relation to an apposition member frame in a desired arrangement Referring to FIG. 25, the support frame 2470 can be concentrically nested within the apposition member frame 2410 to construct an anastomosis device 2480. In this view it can be seen that, in some embodiments, the apices 2484 can be in alignment with the apposition member frame 2410 such that the support frame 2470 and the apposition member frame 2410 support each other.

Figure 26:
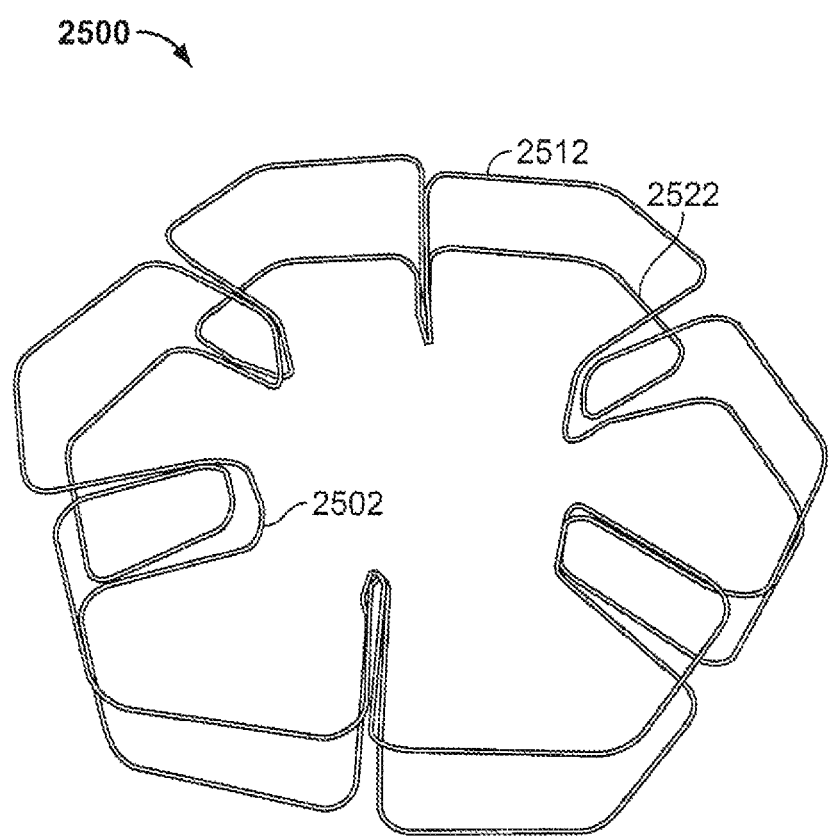
FIG. 26 is a plan view of another exemplary apposition member frame.

Referring to FIG. 26, an alternate apposition member frame 2500 is depicted. The apposition member frame 2500 may be used in conjunction with a support frame, such as, but not limited to, support frame 2411 or support frame 2470. Accordingly, the advantages of the concentrically nested two-part frame construct, as described above, may be achieved using the apposition member frame 2500 as well.

The apposition member frame 2500 may constructed of one or more elongate elements 2502. The one or more elongate members 2502 can be made from any of the materials and may be made using any of the techniques described above in reference to the other elongate members provided herein. The apposition member frame 2500 includes apposition petals 2512 and 2522. In some embodiments, the apposition member frame 2500 is formed as a wound-wire construct. In other embodiments, the apposition member frame 2500 is formed by cutting a precursor material as described above.

Figure 27A:
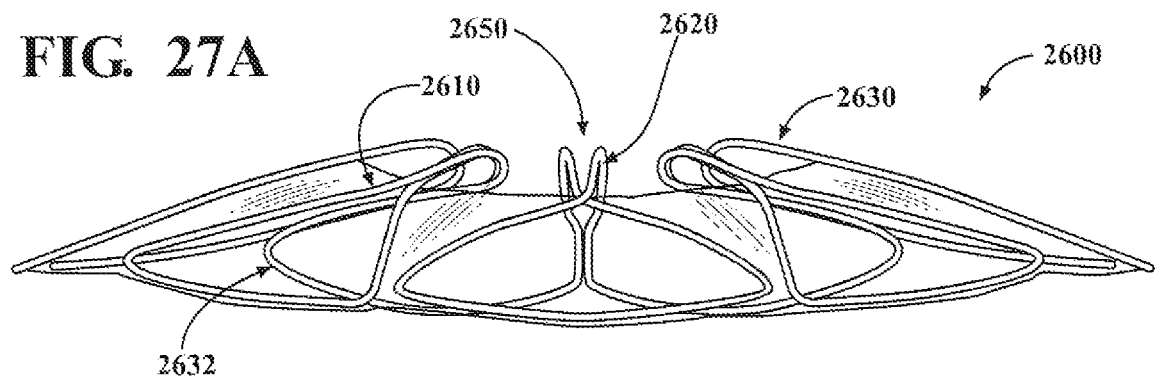
FIG. 27A is a side view of the tissue-sealing device of FIG. 27.

Referring to FIGS. 27 and 27A, another exemplary tissue-sealing device 2600 including a frame 2610 and covering material 2612 is illustrated. The covering material 2612 is disposed on at least a sealing portion 2630 of the frame 2610. The frame 2610 may be formed of one or more elongate element.

The frame 2610 includes an apposition portion 2620, a sealing portion 2630, and a defect-occupying portion 2650. In the depicted embodiment, the apposition portion 2620 and the sealing portion 2630 are configured dissimilarly. The defect-occupying portion 2650 is disposed between the apposition portion 2620 and the sealing portion 2630. In addition, the defect-occupying portion 2650 is configured to traverse the defect or aperture in one or more layers of tissue. The apposition portion 2620 and the sealing portion 2630 may be configured to be on opposite sides of the layer(s) of tissue.

In some embodiments, the frame 2610 includes a single continuous wire that has been bent to form the frame 2610. In the depicted embodiment, the frame 2610 defines diamond-shaped petals 2632 that form the sealing portion 2630 and triangularly-shaped petals 2622 that form the apposition portion 2620. As seen in FIG. 27, the edges of the diamond-shaped petals 2632 in the sealing portion 2630 are substantially parallel to each other, which creates a line of physical contact and a sealing edge and reduces the presence of leakage channels between the sealing petals 2632. In contrast, the triangularly-shaped petals 2622 in the apposition portion 2620 are discrete and may tangentially contact each other. Additionally, the sealing petals 2632 and the apposition petals 2622 have a pre-strained geometry such that an apposition force exists in the absence of any tissue layer(s) (e.g., prior to implantation or in a resting state). The defect-occupying portion does not provide substantial apposition force against tissue surrounding an aperture of the defect.

The use of dissimilar shapes for the apposition petals 2622 and sealing petals 2632 beneficially provide the opportunity to individually optimize the configurations of the apposition portion 2620 independently from those of the sealing portion 2630. It is to be appreciated that in some embodiments, the axes of one or more of the individual apposition petals 2622 may be offset (e.g., skewed) from the axes of one or more of the individual sealing petals 2632. In other embodiments, the axes of one or more of the apposition petals 2622 may be parallel with the axes of one or more of the sealing petals 2632.

The covering material 2612 may be a material as described above in reference to covering material 210. The covering material 2612 may be attached to or disposed on the frame 2610 as described above with respect to the attachment of covering material 210 to elongate member 110.

While the exemplary defect-occupying portion 2650 is depicted as generally circular, it should be understood that the design of the tissue-sealing device 2600 (and other embodiments described herein) advantageously lends itself to sealing a wide variety of differently-sized and shaped apertures. In addition, the appositional force for sealing and migration resistance is substantially provided by the apposition portion 2620 and the sealing portion 2630, rather than the defect-occupying portion 2650. In fact, in some embodiments the appositional forces provided by the apposition portion 2620 and the sealing portion 2630 are substantially independent of the in situ device shape or diameter, thus providing reliable sealing across a wide variety of anatomies, and for dynamic anatomies (e.g., such as the GI tract).

The tissue-sealing device 2600 may be configured to be implanted in a patient such that the covering material 2612 fully overlays and seals the tissue aperture.

Figure 28:
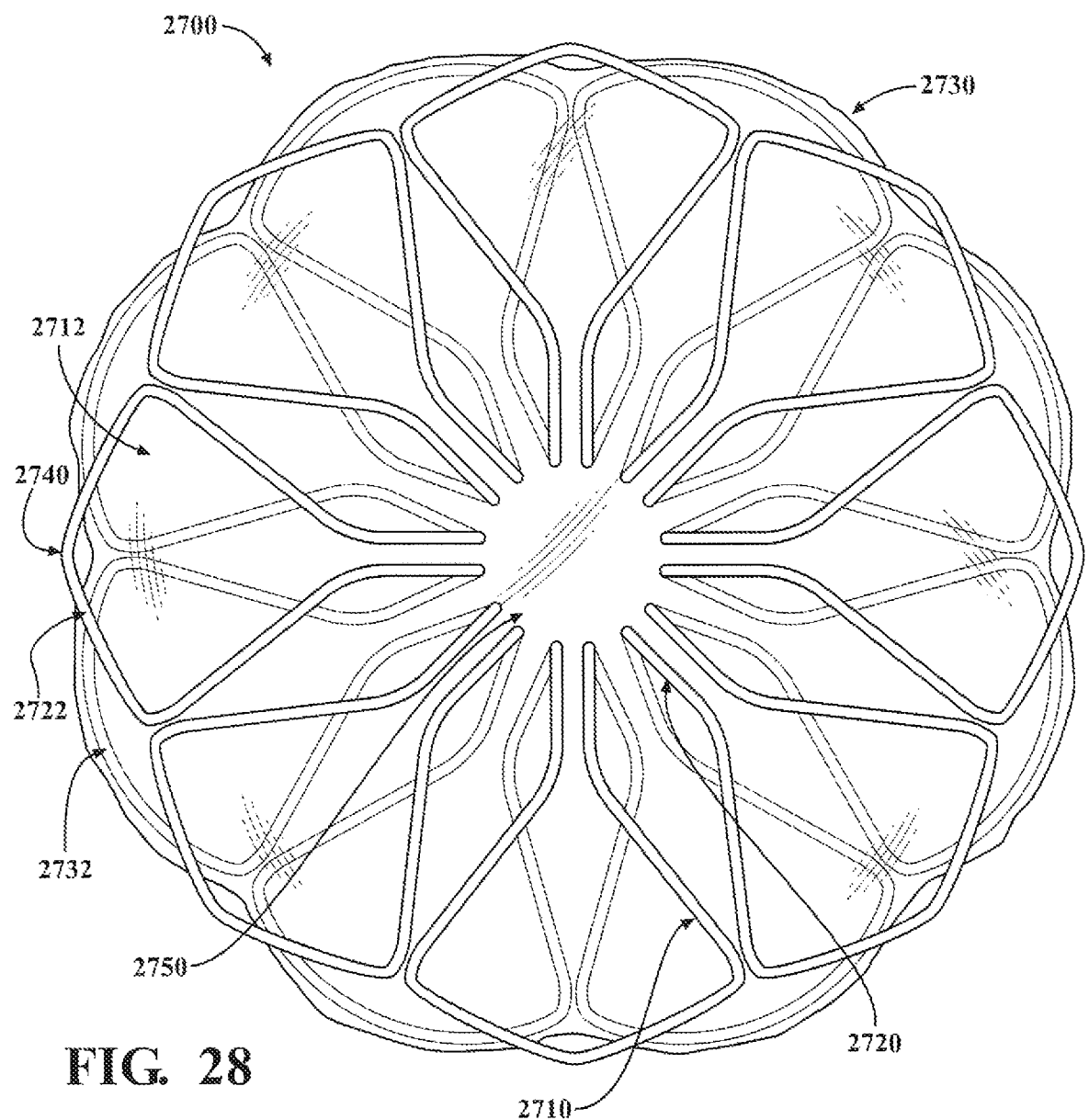
FIG. 28 is a plan view of another exemplary tissue-sealing device including a frame and covering material where the apposition petals and sealing petals are dissimilar.
Figure 28A:
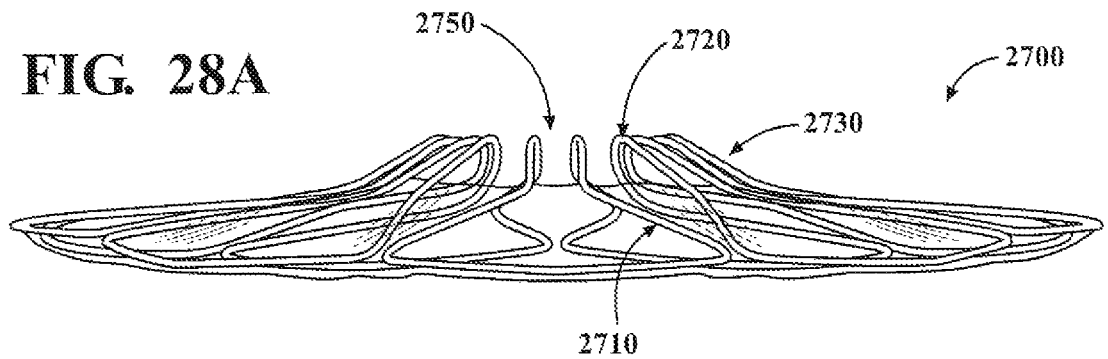
FIG. 28A is a side view of the tissue-sealing device of FIG. 28.

Turning to FIGS. 28 and 28A, another exemplary tissue-sealing device 2700 including a frame 2710 and a covering material 2712 is illustrated. The covering material 2712 is disposed on at least a sealing portion 2730 of the frame 2710. The frame 2710 may be formed of one or more elongate element.

The frame 2710 includes an apposition portion 2720, a sealing portion 2730, and a defect-occupying portion 2750. In the depicted embodiment, the apposition portion 2720 and the sealing portion 2730 are configured dissimilarly. The defect-occupying portion 2750 is disposed between the apposition portion 2720 and the sealing portion 2730. In addition, the defect-occupying portion 2750 is configured to traverse the defect or aperture in one or more layers of tissue. The apposition portion 2720 and the sealing portion 2730 may be configured to be on opposite sides of the layer(s) of tissue.

In some embodiments, the frame 2710 includes a single continuous wire that has been bent to form the frame 2710. The frame 2710 defines one or more apposition petals 2722 that form the apposition portion 2720, and one or more sealing petals 2732 that form the sealing portion 2730. In some embodiments, the axes of one or more of the individual apposition petals 2722 may be offset (e.g., skewed) from the axes of one or more of the individual sealing petals 2732. In some embodiments, the axes of one or more of the apposition petals 2722 may be parallel with the axes of one or more of the sealing petals 2732.

In the depicted embodiment, the apposition petals 2722 include a linear portion extending radially from the defect-occupying portion 2750 and an essentially diamond-shaped outer portion extending from the linear portion at the free ends of the petals 2722. The sealing petals 2732 also include a linear portion extending radially from the defect-occupying portion 2750 and an essentially diamond-shaped portion extending from the linear portion at the free ends of the petals 2732. In the depicted embodiment, the sealing petals 2732 and the apposition petals 2722 are substantially similar, with the exception that the sealing petals 2732 have a more rounded outermost edge than the apposition petals 2722. Additionally, the sealing petals 2732 and the apposition petals 2722 have a pre-strained geometry such that an apposition force exists in the absence of any tissue layer(s) (e.g., prior to implantation or in a resting state). The defect-occupying portion does not provide substantial apposition force against tissue surrounding an aperture of the defect. The use of dissimilar shapes for the apposition petals 2722 and sealing petals 2732 beneficially provide the opportunity to individually optimize the configurations of the apposition portion 2620 independently from those of the sealing portion 2730.

As seen in FIG. 28, the outermost edges of the sealing petals 2732 tangentially touch each other. The abutment of the edges of the sealing petals 2732 creates a line of physical contact and a sealing edge and reduces the presence of leakage channels between the sealing petals 2732. In the depicted embodiment, the sealing petals 2732 are forced into contact by the covering material 2712. In contrast, the apposition petals 2722 in the apposition portion 2720 are discrete (not covered with a covering material) and may move relative to each other. Alternatively, the apposition petals 2722 may tangentially touch each other at the outer edges thereof. The more rounded ends of the sealing petals 2732 (opposed to the less rounded ends of the apposition petals 2722) creates a substantially uniform pressure distribution at the exterior circumference, and in the apposition portion 2720, to facilitate loading into a delivery device.

In addition, the shape of the apposition petals 2722 enables the tissue-sealing device 2700 to be easily inserted into a delivery sheath and/or into or on a delivery catheter. A flexible member may be threaded through at least one apposition petal 2722. In at least one embodiment, the flexible member is threaded through each of the apposition petals 2722. The flexible member may be a cord, wire, strap, or suture. The flexible member can be made of a polymer material including, but not limited to, nylon, polypropylene, polytetrafluoroethylene (PTFE), silk, or a metallic material (e.g., nitinol, aluminum, and stainless steel). The flexible member may also be made of monofilament, twisted strands, or braided strands.

In placing the tissue-sealing device 2700 into a delivery sheath or catheter, the flexible member is tensioned (e.g., pulled), which causes the flexible member to be drawn to the apices 2740 of the apposition petals 2722. As a result of the tensioning and the substantially even distribution of tension on the apices 2740, the apposition petals 2722 are drawn towards each other and into a low-profile configuration. The tissue-sealing device 2700 may then be inserted into the delivery sheath or catheter without entangling the petals 2722, 2732 of the tissue-sealing device 2700.

The covering material 2712 may be a material as described above in reference to covering material 210. The covering material 2712 may be attached to or disposed on the frame 2710 as described above with respect to the attachment of covering material 210 to elongate member 110.

While the exemplary defect-occupying portion 2750 is depicted as generally circular, it should be understood that the design of the tissue-sealing device 2700 (and other embodiments described herein) advantageously lends itself to sealing a wide variety of differently-sized and shaped apertures. In addition, the appositional force for sealing and migration resistance is substantially provided by the apposition portion 2720 and the sealing portion 2730, rather than the defect-occupying portion 2750. In fact, in some embodiments the appositional forces provided by the apposition portion 2720 and the sealing portion 2730 are substantially independent of the in situ device shape or diameter, thus providing reliable sealing across a wide variety of anatomies, and for dynamic anatomies (e.g., such as the GI tract).

The tissue-sealing device 2700 may be configured to be implanted in a patient such that the covering material 2712 fully overlays and seals the tissue aperture.

The tissue-sealing and anastomosis devices provided herein are deployable to a target site within a patient using one or more catheters, delivery sheaths, and other suitable devices and techniques. In some implementations, the devices provided herein are deployable using an endoscopic or laparoscopic approach.

It should be understood from the description herein that, all combinations of shapes, sizes, patterns, components, features, etc. of one tissue-sealing device embodiment and/or one occluder embodiment can be combined with any other shapes, sizes, patterns, components, features, etc. of all other tissue-sealing device embodiments or occluder embodiments, to create an extensive scope of hybrid tissue-sealing devices and occluder devices in addition to the individual embodiments described herein, and such embodiments are considered to be in the scope of the disclosure.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical device for sealing a defect or structure in tissue, said medical device comprising:
   a frame comprising an elongate member, said frame defining:
      an apposition portion;
      a sealing portion; and
      a defect-occupying portion disposed between said apposition portion and said sealing portion, and
   a covering material disposed on at least a portion of said sealing portion,
      wherein said apposition portion contains a plurality of apposition petals,
      wherein said sealing portion contains a plurality of sealing petals, and
      wherein at least some of said apposition petals and at least some of said sealing petals make at least partial contact with each other in the absence of a tissue layer, and have a pre-strained geometry such that an apposition force exists in the absence of a tissue layer such that the apposition petals and the sealing petals that are in at least partial contact are under strain in the absence of a tissue layer in a resting, delivery configuration of the medical device.

2. The medical device of claim 1, wherein a geometry of said apposition petals is substantially the same as a geometry of said sealing petals.

3. The medical device of claim 1, wherein the apposition force facilitates sealing and migration resistance of said medical device and is substantially provided by said apposition portion and said sealing portion.

4. The medical device of claim 1, wherein said apposition petals are configured to move independently of each other.

5. The medical device of claim 1, wherein said apposition petals are configured to be separated from or to abut at least portions of adjacent apposition petals.

6. The medical device of claim 1, wherein said elongate member is a nitinol wire.

7. The medical device of claim 1, further comprising one or more radiopaque markers disposed on said medical device.

8. The medical device of claim 1, wherein said covering material is configured to promote tissue ingrowth or endothelialization into said covering material.

9. The medical device of claim 1, wherein said covering material is configured to inhibit tissue ingrowth or endothelialization into said covering material.

10. The medical device of claim 1, wherein said frame comprises one or more tissue anchorage features.

11. The medical device of claim 1, wherein said apposition portion is free of said covering material.

12. The medical device of claim 1, wherein said apposition portion is configured to conform to a geometry of a first tissue surface and to provide an apposition force against the first tissue surface, and
   wherein said sealing petals are configured to bear a load associated with said first tissue surface without imparting a substantial force on any other sealing petal.

13. The medical device of claim 1, wherein said sealing petals are offset from said apposition petals.

14. The medical device of claim 1, wherein the apposition petals at least partially overlap each other.

15. The medical device of claim 1, wherein the plurality of apposition petals are independent from one another such that they are operable to independently deflect in accordance with topography of the tissue layer.

16. The medical device of claim 1, wherein at least some of the apposition petals are not adjacent to one or more of the plurality of sealing petals, and are positioned in a neutral configuration that is different from a pre-strained configuration.

17. The medical device of claim 1, wherein the apposition petals and the sealing petals that are in at least partial contact cross over each other.

18. A medical device for sealing a defect or structure in tissue, said medical device comprising:
   a frame comprising an elongate member, said frame defining:
      an apposition portion;
      a sealing portion; and
      a defect-occupying portion disposed between said apposition portion and said sealing portion, and
   a covering material disposed on at least a portion of said sealing portion,
      wherein said apposition portion contains a plurality of apposition petals,
      wherein said sealing portion contains a plurality of sealing petals,
      wherein said apposition petals are configured to move independently of each other,
      wherein said sealing petals abut each other and create a sealing edge, and
      wherein at least some of said apposition petals and at least some of said sealing petals make at least partial contact with each other in the absence of a tissue layer and have a pre-strained geometry such that an apposition force exists in the absence of a tissue layer such that the apposition petals and the sealing petals that are in at least partial contact are under strain in the absence of the tissue layer in a resting, delivery configuration of the medical device.

19. The medical device of claim 18, wherein a geometry of said apposition petals is substantially the same as a geometry of said sealing petals.

20. The medical device of claim 18, wherein said apposition petals and said sealing petals have a linear portion extending radially from said defect-occupying portion and a substantially diamond-shaped outer portion extending from said linear portion.

21. The medical device of claim 18, wherein the apposition force facilitates sealing and migration resistance of said medical device and is substantially provided by said apposition portion and said sealing portion.

22. The medical device of claim 18, wherein the apposition petals are configured to be separated from or to abut at least portions of adjacent apposition petals.

23. The medical device of claim 18, wherein said elongate member is a nitinol wire.

24. The medical device of claim 18, further comprising one or more radiopaque markers disposed on said medical device.

25. The medical device of claim 18, wherein said covering material is configured to promote tissue ingrowth or endothelialization into said covering material.

26. The medical device of claim 18, wherein said frame comprises one or more tissue anchorage features.

27. The medical device of claim 18, wherein said apposition portion is configured to conform to a geometry of a first tissue surface and to provide an apposition force against the first tissue surface, and wherein said sealing petals are configured to bear a load associated with said first tissue surface without imparting a substantial force on any other sealing petal.

28. An implantable medical device having an expanded, deployed state and a compacted, delivery state, the occluder comprising:

a cover; and a frame including one or more elongate members defining an apposition portion including a plurality of apposition petals, a sealing portion including a plurality of sealing petals, and a defect-occupying portion associated with the cover and defined between the apposition portion and the sealing portion, at least one of the apposition petals and at least one of the sealing petals being in contact with each other in the absence of a tissue layer interposed therebetween and under strain due to that contact when the medical device is in a resting, delivery configuration of the medical device.

* * * * *